(12) United States Patent
DiPersio et al.

(10) Patent No.: US 12,350,349 B2
(45) Date of Patent: Jul. 8, 2025

(54) GENE EDITING OF CAR-T CELLS FOR THE TREATMENT OF T CELL MALIGNANCIES WITH CHIMERIC ANTIGEN RECEPTORS

(71) Applicants: John F. DiPersio, St. Louis, MO (US); Matthew Cooper, St. Louis, MO (US)

(72) Inventors: John F. DiPersio, St. Louis, MO (US); Matthew Cooper, St. Louis, MO (US)

(73) Assignee: Washington University, St. Louis, MO (US)

( * ) Notice: Subject to any disclaimer, the term of this patent is extended or adjusted under 35 U.S.C. 154(b) by 179 days.

(21) Appl. No.: 16/322,803

(22) PCT Filed: Aug. 3, 2017

(86) PCT No.: PCT/US2017/045304
§ 371 (c)(1),
(2) Date: Feb. 1, 2019

(87) PCT Pub. No.: WO2018/027036
PCT Pub. Date: Feb. 8, 2018

(65) Prior Publication Data
US 2020/0000937 A1    Jan. 2, 2020

Related U.S. Application Data

(60) Provisional application No. 62/505,614, filed on May 12, 2017, provisional application No. 62/482,570, filed on Apr. 6, 2017, provisional application No. 62/370,485, filed on Aug. 3, 2016.

(51) Int. Cl.
| | |
|---|---|
| *A61K 40/31* | (2025.01) |
| *A61K 40/11* | (2025.01) |
| *A61K 40/22* | (2025.01) |
| *A61K 40/41* | (2025.01) |
| *A61K 40/42* | (2025.01) |
| *A61K 48/00* | (2006.01) |
| *A61P 35/02* | (2006.01) |
| *A61P 37/06* | (2006.01) |
| *C12N 5/0783* | (2010.01) |
| *C12N 15/00* | (2006.01) |
| *C12N 15/11* | (2006.01) |

(52) U.S. Cl.
CPC .......... *A61K 48/0066* (2013.01); *A61K 40/11* (2025.01); *A61K 40/22* (2025.01); *A61K 40/31* (2025.01); *A61K 40/418* (2025.01); *A61K 40/421* (2025.01); *A61K 40/4211* (2025.01); *A61K 48/0008* (2013.01); *A61K 48/0058* (2013.01); *A61K 48/0091* (2013.01); *A61P 35/02* (2018.01); *A61P 37/06* (2018.01); *C12N 5/0636* (2013.01); *A61K 2239/31* (2023.05); *A61K 2239/38* (2023.05); *A61K 2239/48* (2023.05)

(58) Field of Classification Search
None
See application file for complete search history.

(56) References Cited

U.S. PATENT DOCUMENTS

| | | | |
|---|---|---|---|
| 5,795,572 A | 8/1998 | Diegel et al. | |
| 7,446,190 B2 | 11/2008 | Sadelain et al. | |
| 10,201,606 B2 | 2/2019 | Lutteropp et al. | |
| 11,390,658 B2* | 7/2022 | Bari ................... | C07K 14/7051 |
| 2003/0161809 A1 | 8/2003 | Houston et al. | |
| 2012/0321667 A1 | 12/2012 | Sentman | |
| 2013/0280220 A1 | 10/2013 | Ahmed et al. | |
| 2015/0299317 A1 | 10/2015 | Orentas et al. | |
| 2015/0342993 A1 | 12/2015 | Kloss et al. | |
| 2016/0009813 A1 | 1/2016 | Themeli et al. | |
| 2016/0144026 A1 | 5/2016 | Lutteropp et al. | |
| 2016/0319367 A1* | 11/2016 | Bernards ............. | C12Q 1/6886 |
| 2017/0029777 A1 | 2/2017 | Pillai | |
| 2017/0175128 A1* | 6/2017 | Welstead ........... | C12N 15/1135 |
| 2017/0290858 A1 | 10/2017 | Zhao et al. | |
| 2018/0008638 A1* | 1/2018 | Campana ............... | A61P 35/00 |
| 2018/0066034 A1* | 3/2018 | Ma ..................... | C07K 16/2806 |
| 2018/0104308 A1 | 4/2018 | Mamonkin et al. | |
| 2018/0119123 A1* | 5/2018 | Gori ......................... | C12N 9/22 |
| 2018/0148506 A1 | 5/2018 | Png et al. | |
| 2018/0311269 A1 | 11/2018 | Lobb et al. | |
| 2020/0000937 A1 | 1/2020 | DiPersio et al. | |
| 2020/0040056 A1 | 2/2020 | DiPersio et al. | |
| 2020/0071397 A1 | 3/2020 | DiPersio et al. | |

FOREIGN PATENT DOCUMENTS

| | | |
|---|---|---|
| IL | 254141 B | 7/2022 |
| JP | 2015513394 A | 5/2015 |
| JP | 2017535261 A | 11/2017 |
| WO | 2003051926 | 6/2003 |
| WO | 2003051926 A2 | 6/2003 |

(Continued)

OTHER PUBLICATIONS

Vandermeulen et al. New Generation of Plasmid Backbones Devoid of Antibiotic Resistance Marker for Gene Therapy Trials. (Mol Ther, 2011, 19:1942-1949) (Year: 2011).*

Lee et al. Immunologic Characterization of CD7-Deficient Mice1, (Journal of Immunology, 1998, 160:5749-5736). (Year: 1998).*

"Use of Immunophenotyping/Genetic Testing in Differential Diagnosis of Mature B-Cell and NK/T-Cell Neoplasms," NCCN Clinical Practice Guidelines in Oncology, Non-Hodgkin's Lymphomas, Mar. 3, 2015, 11 pgs., Version 2.2015.

Cooper, M. et al., "An 'off-the-shelf' fratricide-resistant CAR-T for the treatment of T cell hematologic malignancies," HHS Public Access Author Manuscript, Aug. 20, 2018, pp. 1-23, published in final edited form as: Leukemia, Sep. 2018, pp. 1970-1983, vol. 32, No. 9.

(Continued)

*Primary Examiner* — Arthur S Leonard
(74) *Attorney, Agent, or Firm* — Polsinelli PC

(57) ABSTRACT

The present disclosure provides the use of fratricide-resistant chimeric antigen receptor T (CAR-T) cells targeting antigens expressed by T cell malignancies.

31 Claims, 25 Drawing Sheets
(19 of 25 Drawing Sheet(s) Filed in Color)
Specification includes a Sequence Listing.

(56) References Cited

FOREIGN PATENT DOCUMENTS

| | | |
|---|---|---|
| WO | 2011059836 A2 | 5/2011 |
| WO | 2013074916 A1 | 5/2013 |
| WO | 2013123061 A1 | 8/2013 |
| WO | 2013126729 A1 | 8/2013 |
| WO | 2013153391 A1 | 10/2013 |
| WO | 2013176915 A1 | 11/2013 |
| WO | 2014055668 A1 | 4/2014 |
| WO | 2014165707 A2 | 10/2014 |
| WO | 2014191128 A1 | 12/2014 |
| WO | 2015075175 A1 | 5/2015 |
| WO | 2015090229 A1 | 6/2015 |
| WO | 2015121454 | 8/2015 |
| WO | 2015121454 A1 | 8/2015 |
| WO | 2015162211 A1 | 10/2015 |
| WO | 2016011210 A2 | 1/2016 |
| WO | 2016069282 A1 | 5/2016 |
| WO | 2016069283 A1 | 5/2016 |
| WO | 2016081518 A2 | 5/2016 |
| WO | 2016100236 A2 | 6/2016 |
| WO | 2016126608 A1 | 8/2016 |
| WO | 2016127257 A1 | 8/2016 |
| WO | 2016138491 A1 | 9/2016 |
| WO | 2016210293 A1 | 12/2016 |
| WO | 2017023803 A1 | 2/2017 |
| WO | 2017062451 A1 | 4/2017 |
| WO | 2017070429 | 4/2017 |
| WO | 2017088012 A1 | 6/2017 |
| WO | 2017112877 A1 | 6/2017 |
| WO | 2017127729 A1 | 7/2017 |
| WO | 2017147538 A1 | 8/2017 |
| WO | 2017149515 A1 | 9/2017 |
| WO | 2017193059 A1 | 11/2017 |
| WO | 2017197347 A1 | 11/2017 |
| WO | 2017213979 A1 | 12/2017 |
| WO | 2017222593 A1 | 12/2017 |
| WO | 2018007263 A1 | 1/2018 |
| WO | 2018026953 A1 | 2/2018 |
| WO | 2018027036 A1 | 2/2018 |
| WO | 2018098306 A1 | 5/2018 |
| WO | 2018195339 A1 | 10/2018 |
| WO | 2019232409 A1 | 12/2019 |
| WO | 2019232425 A1 | 12/2019 |
| WO | 2019232444 A1 | 12/2019 |
| WO | 2019232477 A2 | 12/2019 |
| WO | 2020232427 A2 | 11/2020 |

OTHER PUBLICATIONS

Heczey, A. et al., "Invariant NKT cells with chimeric antigen receptor provide a novel platform for safe and effective cancer immunotherapy," Blood, 2014, pp. 2824-2833, vol. 124, No. 18.
International Search Report and Written Opinion dated Dec. 19, 2019 from related Patent Application No. PCT/ US2019/035052; 14 pgs.
Extended European Search Report dated Feb. 18, 2020 from related European Patent Application No. 17837687.7; 6 pgs.
Savoldo, B. et al., "Epstein Barr virus-specific cytotoxic T lymphocytes expressing the anti-CD30zeta artificial chimeric T-cell receptor for immunotherapy of Hodgkin disease," Blood, Oct. 1, 2007, pp. 2620-2630, vol. 110, No. 7.
Fehse, B. et al., "CD34 Splice Variant: an Attractive Marker for Selection of Gene-Modified Cells," Mol. Ther., 2000, pp. 448-456, vol. 1, No. 5.
Norell, H. et al., "CD34-Based Enrichment of Genetically-Engineered Human T Cells for Clinical Use Results in Dramatically Enhanced Tumor Targeting," NIH Public Access Author Manuscript, Aug. 7, 2013, pp. 1-22, published in final edited form as: Cancer Immunol. Immunother., 2010, pp. 851-862, vol. 59, No. 6.
Office Action dated Jul. 6, 2021 from related U.S. Appl. No. 16/428,624; 14 pgs.
Kleinstiver, B. et al., "High-fidelity CRISPR-Cas9 nucleases with no detectable genome-wide off-target effects," Nat., Jan. 28, 2016, pp. 490-495, vol. 529.
International Search Report and Written Opinion dated Nov. 12, 2019 from related Patent Application No. PCT/US2019/035010; 14 pgs.
NCBI Reference Sequence NP_001139345.1; Sep. 16, 2019; 4 pgs.
Zheng, W. et al., "Modulation of PI3K signaling to improve CAR T cell function," Oncotarget, 2018, pp. 35807-35808, vol. 9, No. 88.
Office Action dated May 11, 2021 from related European Patent Application No. 17837687.7; 5 pgs.
Bonilla, F. et al., "Targeted gene disruption of murine CD7," International Immunol., 1997, pp. 1875-1883, vol. 9, No. 12.
Bonini, C. et al., "Adoptive T-cell therapy for cancer: the era of engineered T-cells," Eur. J. Immunol., 2015, pp. 2457-2469, vol. 45, Wiley-VCH Verlag Gmbh & Co. KGaA, Weinheim.
Campana, D. et al., "Immunophenotyping of leukemia," J. Immunol. Methods, Sep. 21, 2000, pp. 59-75, vol. 243, Nos. 1-2.
Cooke, K. et al., "An Experimental Model of Idiopathic Pneumonia Syndrome After Bone Marrow Transplantation: I. The Roles of Minor H Antigens and Endotoxin," Blood, Oct. 15, 1996, pp. 3230-3239, vol. 8, No. 8.
Eissenberg, L. et al., "Suicide genes: monitoring cells in patients with a safety switch," Frontiers Pharmacol., Nov. 2014, pp. 1-4, vol. 5, No. 241.
Eissenberg, L. et al., "[18F]FHBG PET/CT Imaging of CD34-TK75 Transduced Donor T Cells in Relapsed Allogeneic Stem Cell Transplant Patients: Safety and Feasibility," Mol. Ther., Jun. 2015, pp. 1110-1122, vol. 23, No. 6.
Eyquem, J. et al., "Targeting a CAR to the TRAC locus with CRISPR/Cas9 enhances tumour rejection," HHS Public Access Author Manuscript, Sept. 2, 2017, pp. 1-28, published in final edited form as: Nat., Mar. 2, 2017, pp. 113-117, vol. 543, No. 7643.
Galetto, R. et al., "Pre-TCRalpha supports CD3-dependent reactivation and expansion of TCRalpha-deficient primary human T-cells," Mol. Ther. Methods Clin. Dev., 2014, pp. 1-9, vol. 14021.
Gerby, B. et al., "Expression of CD34 and CD7 on human T-cell acute lymphoblastic leukemia discriminates functionally heterogeneous cell populations," Leukemia, 2011, pp. 1249-1258, vol. 25. Macmillan Publishers Limited.
Gokbuget, N. et al., "Treatment of Adult ALL According to Protocols of the German Multicenter Study Group for Adult ALL (GMALL)," Acute Leukemias, 2008, pp. 167-176, Chapter 13.
Gokbuget, N. et al., "High single-drug activity of nelarabine in relapsed T-lymphoblastic leukemia/lymphoma offers curative option with subsequent stem cell transplantation," Blood, Sep. 29, 2011, pp. 3504-3511, vol. 118, No. 13.
Goldberg, J. et al., "Childhood T-Cell Acute Lymphoblastic Leukemia: the Dana-Farber Cancer Institute Acute Lymphoblastic Leukemia Consortium Experience," J. Clin. Oncol., Oct. 1, 2003, pp. 3616-3622, vol. 21, No. 19.
Gomes-Silva, D. et al., "CD7-edited T cells expressing a CD7-specific CAR for the therapy of T-cell malignancies," Blood, Jul. 20, 2017, pp. 285-296, vol. 130, No. 3.
Hendel, A. et al., "Chemically modified guide RNAs enhance CRISPR-Cas genome editing in human primary cells," Nat. Biotechnol., 2015, pp. 985-989, vol. 33.
International Search Report and Written Opinion dated Oct. 18, 2017 from related Patent Application No. PCT/US2017/045304; 12 pgs.
Karrman, K. et al., "Pediatric T-cell acute lymphoblastic leukemia," Genes, Chromosomes and Cancer, Feb. 2017, pp. 89-116, vol. 56, No. 2.
Khalidi, H. et al., "Acute Lymphoblastic Leukemia: Survey of Immunophenotype, French-American-British Classification, Frequency of Myeloid Antigen Expression, and Karyotypic Abnormalities in 210 Pediatric and Adult Cases," Am. J. Clin. Pathol., 1999, pp. 467-476, vol. 111.
Kochenderfer, J. et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," J. Clin. Oncol., Feb. 20, 2015, pp. 540-549, vol. 33, No. 6.
Lee, D. et al., "The Future Is Now: Chimeric Antigen Receptors as Net Targeted Therapies for Childhood Cancer," Clin. Cancer Res., May 15, 2012, pp. 2780-2790, vol. 18, No. 10.

(56) References Cited

OTHER PUBLICATIONS

Litzow, M. et al., "How I treat T-cell acute lymphoblastic leukemia in adults," Blood, Aug. 13, 2015, pp. 833-841, vol. 126, No. 7.
Ma, H. et al., "T-cell lymphomas, a challenging disease: types, treatments, and future," Int. J. Clin. Oncol., Feb. 2017, pp. 18-51, vol. 22, No. 1.
MacLeod, D. et al., "Integration of a CD19 CAR into the TCR Alpha Chain Locus Streamlines Production of Allogeneic Gene-Edited CAR T Cells," Mol. Ther., Apr. 2017, pp. 949-961, vol. 25, No. 4.
Mamonkin, M. et al., "A T-cell-directed chimeric antigen receptor for the selective treatment of T-cell malignancies," Blood, Aug. 20, 2015, pp. 983-992, vol. 126, No. 8.
Marks, D. et al., "T-cell acute lymphoblastic leukemia in adults: clinical features, immunophenotype, cytogenetics, and outcome from the large randomized prospective trial (UKALL XII/ECOG 2993)," Blood, Dec. 10, 2009, pp. 5136-5145, vol. 114, No. 25.
Milush, J. et al., "Functionally distinct subsets of human NK cells and monocyte/DC-like cells identified by coexpression of CD56, CD7, and CD4," Blood, Nov. 26, 2009, pp. 4823-4831, vol. 114, No. 23.
Miwa, H. et al., "Biological Characteristics of CD7(+) Acute Leukemia," Leuk. Lymphoma, Apr. 1996, pp. 239-244, vol. 21, Harwood Academic Publishers GmbH, The Netherlands.
Osborn, M. et al., "Evaluation of TCR Gene Editing Achieved by TALENs, CRISPR/Cas9, and megaTAL Nucleases," Mol. Ther., Mar. 2016, pp. 570-581, vol. 24, No. 3.
Park, J. et al., "CD19-targeted CAR T-cell therapeutics for hematologic malignancies: interpreting clinical outcomes to date," Blood, Jun. 30, 2016, pp. 3312-3320, vol. 127, No. 26.
Patel, J. et al.. "The immunophenotype of T-lymphoblastic lymphoma in children and adolescents: a Children's Oncology Group report," British J. Haematol., 2012, pp. 454-461, vol. 159, Blackwell Publishing Ltd.
Pinz, K. et al., "Preclinical targeting of human T-cell malignancies using CD4-specific chimeric antigen receptor (CAR)-engineered T cells," Leukemia, 2016, pp. 701-707, vol. 30.
Porter, D. et al., "Chimeric antigen receptor T cells persist and induce sustained remissions in relapsed refractory chronic lymphocytic leukemia," Sci. Transl. Med., Sept. 2, 2015, pp. 1-12, vol. 7, No. 303, 303ra139.
Qasim, W. et al., "Molecular remission of infant B-ALL after infusion of universal TALEN gene-edited CAR T cells," Sci. Transl. Med., Jan. 25, 2017, pp. 1-8, vol. 9, No. 374.
Reinhold, U. et al., "CD7-negative T cells represent a separate differentiation pathway in a subset of post-thymic helper T cells," Immunology, 1996, pp. 391-396, vol. 89.
Stock, W. et al., "Alemtuzumab can be Incorporated Into Front-Line Therapy of Adult Acute Lymphoblastic Leukemia (ALL): Final Phase I Results of a Cancer and Leukemia Group B Study (CALGB 10102)," Blood, 51st ASH Annual Meeting Abstracts, Nov. 20, 2009, vol. 114, No. 22, Abstract 838.
Tiftik, N. et al., "The importance of CD7 and CD56 antigens in acute leukaemias," Int. J. Clin. Practice, Feb. 2004, pp. 149-152, vol. 58, No. 2.
Tsai, S. et al., "GUIDE-Seq enables genome-wide profiling of off-target cleavage by CRISPR-Cas nucleases," HHS Public Access Author Manuscript, Aug. 1, 2015, pp. 1-23, published in final edited form as: Nat. Biotech., Feb. 2015, pp. 187-197, vol. 33, No. 2.
Kirberg, Peripheral T Cell Survival Required Continual Ligation of the T Cell Receptor to Major Histocompatibility Complex-Encoded Molecules, J. Exp. Med., Oct. 20, 1997, vol. 186, No. 8, pp. 12699-1275.
Rappl, The CD7-subset of CD4+ memory T cells is prone to accelerated apoptosis that is prevented by Interleukin-15 (IL-15), Cell Death and Differentiation, 2001, vol. 8, pp. 395-402.
Deyev, S. et al., "Multivalency: the hallmark of antibodies used for optimization of tumor targeting by design," BioEssays, 2008, pp. 904-918, vol. 30, Wiley Periodicals, Inc.

Harrer, D. et al., "Chimeric Antigen Receptors in Different Cell Types: New Vehicles Join the Race," Human Gene Ther., Jan. 2018, pp. 547-558, vol. 29, No. 5.
Mack, M. et al., "A small bispecific antibody construct expressed as a functional single-chain molecule with high tumor cell cytotoxicity," PNAS, Jul. 1995, pp. 7021-7025, vol. 92.
Office Action dated Apr. 15, 2022 from related U.S. Appl. No. 16/428,789; 28 pgs.
Carpenito, C. et al., "Control of large, established tumor xenografts with genetically retargeted human T cells containing CD28 and CD137 domains," PNAS, Mar. 3, 2009, pp. 3360-3365, vol. 106, No. 9.
Extended European Search Report dated Apr. 8, 2022 from related European Patent Application No. 19811980.2; 10 pgs.
Karpanen, T. et al., "T-cell receptor gene therapy—ready to go viral?," Mol. Oncol., Oct. 2015, pp. 2019-2042, vol. 9.
Office Action dated Mar. 8, 2022 from related Japanese Patent Application No. 2019-527775; 7 pgs., with English translation.
Orentas, R. et al., "Bioinformatic description of immunotherapy targets for pediatric T-cell leukemia and the impact of normal gene sets used for comparison," Front. Oncol., Jun. 2014, pp. 1-11, vol. 4, No. 134.
Written Opinion and Search Report dated Mar. 15, 2022 from related Singaporean Patent Application No. 11201900772Y; 11 pgs.
Extended European Search Report dated Feb. 16, 2022 from related European Patent Application No. 19810294.9; 9 pgs.
Office Action dated Feb. 22, 2022 from related U.S. Appl. No. 16/428,624; 16 pgs.
Rotolo, A., "CAR-iNKT cells as a novel immunotherapy for B cells malignancies," Author Thesis, Imperial College London, Apr. 2018, 209 pgs.; https://doi.org/10.25560/82147.
Office Action dated May 25, 2021 from related Japanese Patent Application No. 2019-527775; 10 pgs., with English translation.
The Journal of the Japanese Society of Internal Medicine, 2008, pp. 1553-1560, vol. 97, No. 7.
Chinese Application No. 201780061572.2; First Office Action issued Jun. 22, 2022, 6 pgs.
Chinese Application No. 201780061572.2; Second Office Action issued Jan. 12, 2023, 4 pgs.
South Korean Application No. 10-2019-7006314, Office Action issued Sep. 29, 2022, 5 pgs.
Gerby, et al., Expression of CD34 and CD7 on human T-cell acute lymphoblastic leukemia discriminates functionally heterogeneous cell populations; Leukemia, 2011, vol. 25, Nature, pp. 1249-1258.
Mamonkin, et al., A T-cell-directed chimeric antigen receptor for the selective traetment of T-cell malignancies; Blood, Aug. 20, 2015, vol. 126, No. 8, pp. 983-992.
Rettig, Transduction and Selection of Human T Cells with Novel CD34/Thymidine Kinase Chimeric Suicide Genes for the Treatment of Graft versus-Host Disease; Molecular Therapy., Jul. 2003, vol. 8, No. 1, pp. 29-41.
Austrialian Application No. 2017306557; Examination Report issued Jul. 19, 2022, 4 pages.
Doronin I.I., et al., "Ganglioside GD2 in Reception and Transduction of Cell Death Signal in Tumor Cells," BMC Cancer 2014, vol. 14, No. 295, 17 pages.
International Preliminary Report on Patentability for International Application No. PCT/US2017/045304, mailed Feb. 14, 2019, 9 pages.
International Preliminary Report on Patentability for International Application No. PCT/US2019/035010, mailed Dec. 10, 2020, 10 Pages.
International Preliminary Report on Patentability for International Application No. PCT/US2019/035052, mailed Dec. 10, 2020, 10 Pages.
Marrero I., et al., "Type II NKT Cells in Inflammation, Autoimmunity, Microbial Immunity, and Cancer," Frontiers in Immunology, Jun. 17, 2015, vol. 6, No. 316, 6 Pages.
Oh S.J., et al., "Role of Type II NKT Cells in the Suppression of Graft-Versus-Host Disease," Critical Reviews in Immunology, 2008, vol. 28, No. 3, pp. 249-267.

(56) References Cited

OTHER PUBLICATIONS

Ren J., et al., "Multiplex Genome Editing to Generate Universal CAR T Cells Resistant to PD1 Inhibition," Clinical Cancer Research, May 1, 2017, vol. 23, No. 9, pp. 2255-2266, doi:10.1158/1078-0432.CCR-16-1300.
Shearer R.F., et al., "Experimental Design for Stable Genetic Manipulation in Mammalian Cell Lines: Lentivirus and Alternatives," Genes to Cells, 2015, vol. 20, pp. 1-10.
Singh A.K., et al., "Type II NKT Cells: an Elusive Population With Immunoregulatory Properties," Frontiers in Immunology, Aug. 28, 2018, vol. 9, Article 1969, 8 Pages.
Ku X., et al., "The basics of CAR T Design and Challenges in Immunotherapy of Solid Tumors—Ovarian Cancer as a Model," Human Vaccines Immunotherapeutics, 2017, vol. 13, No. 7, 1548-1555, doi: 10.1080/21645515.2017.1291473.
ATCC Catalog, CCRF-CEM (CCL-119™), available at www.atcc.org/products/ccl-119.
ATCC Catalog, MOLT-4 (CRL-1582™), available at www.atcc.org/products/crl-1582.
ATCC Catalog, NK-92® (CRL-2407™), available at www.atcc.org/products/crl-2407.
Fabian, et al., "The emerging role of off-the-shelf engineered natural killer cells in targeted cancer immunotherapy," Mal Ther Oncol, vol. 23, pp. 266-276 (2021).
You, et al., "A novel CD7 chimeric antigen receptor-modified NK-92MI cell line targeting T-cell acute lymphoblastic leukemia," Am J Cancer Res, vol. 9(1), pp. 64-78 (Jan. 1, 2019).
Data Robustness and Reproducibility in Gene Editing Applications: Today's Limits and Tomorrow's Potential, GEN: Gen Eng and Biotech News 40(S4):S9-S13 (2020).
Examination Report No. 2 for Australian Application No. 2017306557, mailed on Jun. 27, 2023, 3 pages.
Office Action for Canadian Patent Application No. 3032429, mailed on Jul. 5, 2023, 6 pages.
Office Action for Russian Patent Application No. 2020143576, dated Dec. 7, 2022, 14 pages.
Costa, et al., Genome Editing Using Engineered Nucleases and Their Use in Genomic Screening, the Assay Guidance Manual, Nov. 20, 2017, pp. 1-24.
Faure, et al., Comparative genomics and evolution of trans-activating RNAs in Class 2 CRISPR-Cas systems, RNA Biology, 2019, vol. 16, No. 4, pp. 435-448.
Jinek, et al., A Programmable Dual-RNA-Guided DNA Endonuclease in Adaptive Bacterial immunity, Science, 2012, vol. 333, pp. 816-821.
Ran, et al., Genome engineering using the CRISPR-Cas9 system, Nature Protocols, 2013, vol. 8, No. 11, pp. 2281-2308.
Scott, et al., Targeted genome regulation and modification using transcription activator-like effectors, FEBS Journal, 2014, vol. 281, pp. 4583-4597.
Schanberg, et al., Isolation and characterization of the demonic human CD7 gene: structural similarity with the murine Thy-1 gene, PNAS, 1991, vol. 88.2, pp. 603-607.
Varshney, et al., A high-throughput functional genomics workflow based on CRISPR/Cas9-mediated targeted mutagenesis in zebrafish, Nature Protocols, 2016, vol. 11(12), pp. 2357-2375.
Ghobadi, et al., Anti-CD7 allogeneic WU-CART-007 in patients with replased/refractory T-cell acute lymphoblastic leukemia/lymphoma: a phase ½ trial, Research Square, 2024, 1 pg.
Thorsen, et al., Tumor-specific usage of alternative transcription start sites in colorectal cancer identified by genome-wide exon array analysis, BMC Genomics, 2011, vol. 12, pp. 1-14.
Badri H., et al., "Optimization of Radiation Dosing Schedules for Proneural Glioblastoma," Journal of Mathematical Biology, Jun. 21, 2015, vol. 72, 36 pages.
Baylot V., et al., "TCTP Has a Crucial Role in the Different Stages of Prostate Cancer Malignant Progression," TCTP/tpt1-Remodeling Signaling from Stem Cell to Disease, 2017, vol. 64, pp. 255-261.
Dai Q., et al., "4-1BB Signaling Boosts the Anti-Tumor Activity of CD28-Incorporated 2nd Generation Chimeric Antigen Receptor-Modified T Cells," Frontiers in Immunology, Nov. 13, 2020, vol. 11, Article No. 539654, pp. 1-11.
Decision on Rejection for Chinese Patent Application No. 201780061572.2, mailed on Nov. 21, 2023, 10 pages.
Final Office Action for U.S. Appl. No. 16/428,624 mailed on Feb. 2, 2022, 24 Pages.
Final Office Action for U.S. Appl. No. 16/428,624 mailed on May 30, 2023, 25 Pages.
First Office Action and Search Report for Chinese Patent Application No. 201980050879.1, dated Oct. 10, 2022, 16 pages.
Jahn E.M., et al., "How to Systematically Evaluate Immunogenicity of Therapeutic Proteins—Regulatory Considerations," New Biotechnology, Jun. 2009, vol. 25, No. 5, pp. 280-286.
Jinek M., et al., "A Programmable Dual-RNA-Guided DNA Endonuclease in Adaptive Bacterial Immunity," Science, Aug. 17, 2012, vol. 337, pp. 816-821.
Kontermann R.E., et al., "Bispecific Antibodies," Drug Discovery Today, Jul. 2015, vol. 20, No. 7, pp. 838-847.
Kulemzin S.V., et al., "Fundamentals of the Design of Chimeric Antigenic Receptors," Acta Naturae (Russian version), 2017, vol. 9, No. 1, pp. 6-15.
Non Final Office Action for U.S. Appl. No. 16/428,624 mailed on Sep. 13, 2022, 31 Pages.
Office Action and Search Report for Russian Patent Application No. 2020143576, dated May 4, 2023, 21 pages.
Office Action for Japanese Patent Application No. 2020-566909, mailed on Jun. 13, 2023, 10 Pages.
Office Action for Japanese Patent Application No. 2020-566909, mailed on Nov. 28, 2023, 4 Pages.
Ran F.A., et al., "Genome Engineering Using the CRISPR-Cas9 System," Nature Protocols, Oct. 24, 2013, vol. 08, No. 11, pp. 2281-2308.
Rappl G., et al., "The CD3-Zeta Chimeric Antigen Receptor Overcomes TCR Hypo-Responsiveness of Human Terminal Late-Stage T Cells," PLoS One, Jan. 2012, vol. 7, No. 1, pp. 1-10.
Sadelain, et al., The Basic Principles of Chimeric Antigen Receptor Design, Cancer Discovery, Apr. 2013, vol. 3, Issue 4, pp. 388-398.
Scott N.F.J., et al., "Targeted Genome Regulation and Modification Using Transcription Activator-like Effectors," FEBS Journal, 2014, vol. 281, No. 20, pp. 4583-4597, doi:10.1111/febs.12973.
Second Office Action for Chinese Patent Application No. 201980050879.1, dated Sep. 16, 2023, 12 pages.
Tang X.Y., et al., "Third-Generation CD28/4-1BB Chimeric Antigen Receptor T Cells for Chemotherapy Relapsed or Refractory Acute Lymphoblastic Leukaemia: a Non-Randomised, Open-Label Phase I Trial Protocol," BMJ Open, 2016, vol. 6, No. 12, pp. 1-7.
Textor A., et al., "CD28 Co-Stimulus Achieves Superior CAR T Cell Effector Function against Solid Tumors Than 4-1BB Co-Stimulus," Cancers, Mar. 2, 2021, vol. 13, No. 5, pp. 1-17.
Third Office Action for Chinese Patent Application No. 201780061572.2, mailed on Jul. 18, 2023, 12 pages.
Weinkove R., et al., "Selecting Costimulatory Domains for Chimeric Antigen Receptors: Functional and Clinical Considerations," Clinical Translational Immunology, May 11, 2019, vol. 8, No. 5, 14 pages.
Zhao X., et al., "Efficacy and Safety of CD28- or 4-1BB-Based CD19 CAR-T Cells in B Cell Acute Lymphoblastic Leukemia," Molecular Therapy: Oncolytics, 2020, vol. 18, 18 pages.

\* cited by examiner

| Marker | WT<br>% (+/- SD) | WT CART19<br>% (+/- SD) | WT CART7<br>% (+/- SD) |
|---|---|---|---|
| CD4 | 57.2 (0.4) | 58.2 (0.5) | 84.8 (1.4) |
| CD8 | 42.4 (0.7) | 36.1 (1.8) | 13.0 (2.5) |
| CXCR3 | 58.9 (1.9) | 39.2 (2.9) | 16.4 (6) |
| CCR6 | 37.5 (0.6) | 33.5 (1.9) | 24.6 (4.0) |
| CCR4 | 33.6 (0.5) | 38.3 (2.0) | 34 (6.7) |
| CCR7 | 3.7 (0.2) | 1.51 (0.2) | 1.1 (0.05) |
| CCR10 | 3.41 (0.2) | 3.50 (0.37) | 0.56 (0.2) |
| CD45RA | 0.54 (0.01) | 0.51 (0.02) | 0.87 (0.2) |
| CD185 | 0.41 (0.03) | 0.51 (0.1) | 1.6 (0.2) |

GENE EDITING OF CAR-T CELLS FOR THE TREATMENT OF T CELL MALIGNANCIES WITH CHIMERIC ANTIGEN RECEPTORS

CROSS REFERENCE TO RELATED APPLICATIONS

This application claims the benefit of International Application No. PCT/US2017/045304, filed on Aug. 3, 2017, and U.S. Provisional Application Ser. No. 62/370,485 filed on Aug. 3, 2016, U.S. Provisional Application Ser. No. 62/482,570 filed on Apr. 6, 2017, and U.S. Provisional Application Ser. No. 62/505,614 filed on May 12, 2017, which are hereby incorporated by reference in their entirety.

FIELD OF THE INVENTION

This application generally relates to T cell therapy. In particular, the disclosure relates to engineered chimeric antigen receptor (CAR)-T cells and methods of using the same. The disclosed compositions and methods are particularly useful for the treatment of myeloid and lymphoid malignancies.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

T cells can be genetically modified to express chimeric antigen receptors (CARs), which are fusion proteins comprised of an antigen recognition moiety and T cell activation domains. Chimeric antigen receptor T cells demonstrate exceptional clinical efficacy against B cell malignancies. However, the development of CAR-T cell therapy against T cell malignancies has proven problematic, in part due to the shared expression of target antigens between malignant T cells and effector T cells. Expression of target antigens on CAR-T cells may induce fratricide of CAR-T cells and loss of efficacy, and also reduce clinical benefit. Therefore CAR-T cells that do not induce fratricide but are effective in the treatment of T cell malignancies are needed.

SUMMARY OF THE INVENTION

In an aspect, the disclosure provides a T cell comprising a chimeric antigen receptor (CAR-T cell), wherein the CAR-T cell is deficient in an antigen to which the chimeric antigen receptor specifically binds, and wherein the chimeric antigen receptor specifically binds a surface-expressed antigen on a malignant tumor or cancer. In various aspects the antigen may be expressed on a malignant T cell. For example, the antigen may be CD7, CD5, CD2, CD30, or CD4. The CAR-T cell may also comprise a suicide gene. Alternatively or in addition, the CAR-T cell may comprise a modification to the endogenous T-cell Receptor Alpha Chain (TRAC) such that T cell receptor (TCR) mediated signaling is blocked in the CAR-T cell.

In another aspect, the disclosure provides a method of treating a mammal having a malignancy, the method comprises administering to the mammal a plurality of chimeric antigen receptor T (CAR-T) cells, each CAR-T cell comprising the same chimeric antigen receptor, wherein the CAR-T cells are deficient in an antigen to which the chimeric antigen receptor specifically binds, and wherein the chimeric antigen receptor specifically binds an antigen expressed on the malignant tumor or cancer of the subject. In various aspects the antigen may be expressed on a malignant T cell. For example, the antigen may be CD7, CD5, CD2, CD30, or CD4. The plurality of CAR-T cells may also comprise a suicide gene. Alternatively or in addition, the plurality of CAR-T cells may comprise a modification to the endogenous T-cell Receptor Alpha Chain (TRAC) such that T cell receptor (TCR) mediated signaling is blocked in the CAR-T cells.

In another aspect, the disclosure provides a method of preventing or reducing graft versus host disease in a subject in need of CAR-T cell therapy, the method comprises administering to the mammal a plurality of chimeric antigen receptor T (CAR-T) cells, each CAR-T cell comprising (a) the same chimeric antigen receptor and (b) a suicide gene and/or a modification such that T cell receptor (TCR) mediated signaling is blocked in the CAR-T cells; wherein the CAR-T cells are deficient in an antigen to which the chimeric antigen receptor specifically binds, and wherein the chimeric antigen receptor specifically binds an antigen expressed on the malignant tumor or cancer of the subject. In various aspects the antigen may be expressed on a malignant T cell. For example, the antigen may be CD7, CD5, CD2, CD30, or CD4. In further aspects, the subject may be in need of allogenic CAR-T cell therapy.

In another aspect, the disclosure provides a method of preventing or reducing alloreactivity in a subject in need of allogenic CAR-T cell therapy, the method comprises administering to the mammal a plurality of chimeric antigen receptor T (CAR-T) cells, each CAR-T cell comprising (a) the same chimeric antigen receptor and (b) a suicide gene and/or a modification of the endogenous T-cell Receptor Alpha Chain (TRAC) such that T cell receptor (TCR) mediated signaling is blocked in the CAR-T cells; wherein the CAR-T cells are deficient in an antigen to which the chimeric antigen receptor specifically binds, and wherein the chimeric antigen receptor specifically binds an antigen expressed on the malignant tumor or cancer of the subject. In various aspects the antigen may be expressed on a malignant T cell. For example, the antigen may be CD7, CD5, CD2, CD30, or CD4.

Further aspects and iterations of the present disclosure are included below.

BRIEF DESCRIPTION OF THE FIGURES

The application file contains at least one drawing executed in color. Copies of this patent application publication with color drawing(s) will be provided by the Office upon request and payment of the necessary fee.

FIG. 4A illustrates the treatment schedule, FIG. 4B illustrates the reduction of tumor in CD7-CAR mice compared to controls, FIG. 4C illustrates that the total photon out from mice decrease in CD7 CAR mice compared to controls, and FIG. 4D illustrates that mice receiving CD7 CAR-T cells survived significantly longer than mice treated with CD19 CAR-T cells.

FIG. 5A shows schematics of anti-CD7-CAR and anti-CD19-CAR constructs, FIG. 5B illustrates T cells cultured in Xcyte media supplemented with 50 U/mL IL-2 and 1 Ong/ml IL15 in the presence of anti-CD3/CD28 beads, FIG. 5C illustrates that in contrast to CART19, CART7 undergo fratricide and fail to demonstrate robust expansion in the days following transduction, FIG. 5D illustrates that CART7 cells are skewed towards a CD4 phenotype, FIG. 5E illustrates editing efficiencies of gRNA targeting CD7 as a percentage of sequencing reads with indels relative to WT cells, FIG. 5F illustrates the experimental design to determine gene editing efficiencies by flow cytometry, FIG. 5G illustrates flow cytometry data analyzed using FlowJo V10, FIG. 5H illustrates the percentage of cells that were CD7+ following gene editing with CD7g4, FIG. 5I illustrates targeted deep-sequencing of CD7 locus following CRISPR/Cas9 gene editing with CD7g4 to detect non-homologous end joining, and FIG. 5J illustrates viability of primary T cells following CRISPR/Cas9 gene editing with CD7g4.

FIG. 6A illustrates the schema of gene edited CAR-T generation, FIG. 6B illustrates cell counts as determined using a Nexcelom Cellometer with ViaStain™, FIG. 6C illustrates that WT Tcells transduced with lenti-GFP (GFP+ T cells) were effectively eliminated by CD7ΔCART7 compared to CD7ΔCART19, FIG. 6D illustrates that CD7ΔCART7 effectively kill CD7+ T-ALL cell lines relative to CD7ΔCART19 in MOLT-4, MOLT-3, and HSB-2 cells, FIG. 6E depicts an experimental design of treating NSG mice injected with CCRF-CEMCBR-GFP with CD7ΔCART7 or CD7ΔCART19, FIG. 6F illustrates that CD7ΔCART7-treated mice have significantly prolonged survival relative to CD7ΔCART19-treated mice, and FIG. 6G illustrates that CD7ΔCART7-treated mice have significantly reduced tumor burden relative to CD7ΔCART19-treated mice, by BLI imaging.

FIG. 7A illustrates the schematic of T cells were cultured in Xcyte media supplemented with 50 U/mL IL-2 and 10ng/ml IL15 in presence of anti-CD3/CD28 beads (bead to cell ratio, 3:1). On day +2 post activation, beads were removed and 4×106 T cells were electroporated using the Lonza nuceleofector4DTM,15 μg spCas9 mRNA, 20 μg of CD7gRNA, and 20 μg of TRACgRNA. CD3+ CAR-T were depleted on day +7 using Miltenyi anti-CD3 microbeads, according to the manufacturer's instructions, and cultured for an additional two days, FIG. 7B -FIG. 7C illustrates Multiplex gene editing results in high efficiency double deletion of TRAC and CD7 as determined by FACS and targeted deep-sequencing of the FIG. 7D. CD7 and FIG. 7E. TRAC loci, FIG. 7F illustrates CD7ΔCART7 and UCART7 exhibit robust expansion, but yield fewer cells likely due to fratricide of both the residual non-gene edited T cells and persistent CD7 surface expression on gene edited cells, and FIG. 7G illustrates that UCART7 was equal to CD7ΔCART7 in efficiency of killing the CD7+ T-ALL cell line in vitro, even at low effector to target ratios.

FIG. 8A illustrates representative FACS plots, and FIG. 8B illustrates that CD7ΔCAR7 and UCART7 effectively killed T-ALL blasts relative to CD7ΔCAR19 and UCART19.

FIG. 9A illustrates the experimental design, FIG. 9B illustrates representative flow cytometry plots of blood analysis presented to show both tumor and T cells, FIG. 9C shows the percentage of tumor cells out of total mouse and human CD45 cells in the blood, FIG. 9D shows the percentage of tumor cells out of total mouse and human CD45 cells in the spleen, FIG. 9E shows clinical GvHD scores, graded according to Cooke, and FIG. 9F shows representative images of mice following infusion of WT T cells, TRACΔ T cells, UCART7, and UCART19.

DETAILED DESCRIPTION OF THE INVENTION

Figure 1:
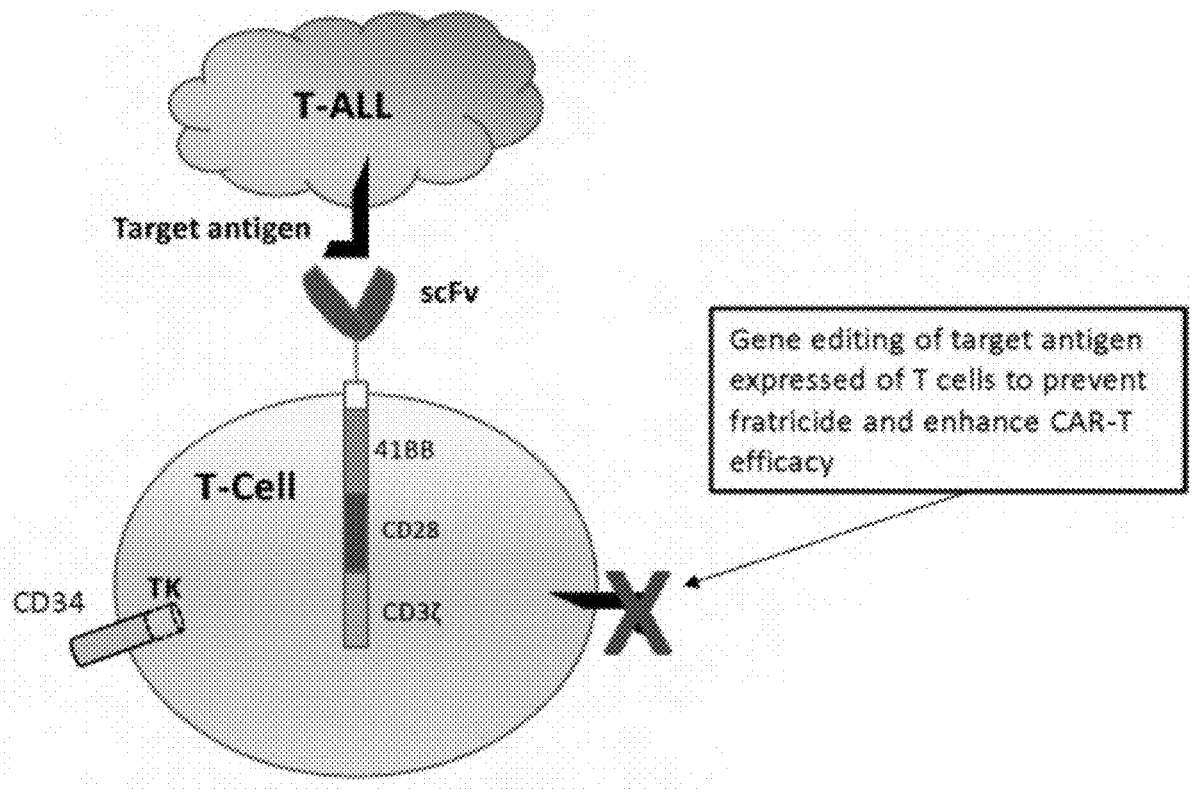
FIG. 1 illustrates the schematic of engineered CAR-T cells.

In the context of the present disclosure, fratricide occurs when a CAR-T cell becomes the target of, and is killed by, another CAR-T cell comprising the same chimeric antigen receptor as the targeted CAR-T cell because the targeted CAR-T cell expresses the antigen specifically recognized by the chimeric antigen receptor on both T cells. To overcome this problem known in the art, the present disclosure provides T cells comprising a chimeric antigen receptor, wherein the T cells are deficient in an antigen to which the chimeric antigen receptor specifically binds. Because a CAR-T cell of the present disclosure is deficient in an antigen that is specifically bound by the chimeric antigen receptor of the T cell, the T cell is referred to as "fratricide-resistant." The present disclosure also encompasses methods of engineering said T cells and use thereof.

Various aspects of the invention are described in further detail in the following sections.

I. CAR-T Cells

One aspect of the present disclosure encompasses T cells comprising a chimeric antigen receptor, wherein the T cells are deficient in an antigen to which the chimeric antigen receptor specifically binds, i.e., fratricide-resistant CAR-T cells.

A CAR-T cell is a T cell that expresses a chimeric antigen receptor. The phrase "chimeric antigen receptor (CAR)," as used herein and generally used in the art, refers to a recombinant fusion protein that has an antigen-specific extracellular domain coupled to an intracellular domain that directs the cell to perform a specialized function upon binding of an antigen to the extracellular domain. The terms "artificial T-cell receptor," "chimeric T-cell receptor," and "chimeric immunoreceptor" may each be used interchangeably herein with the term "chimeric antigen receptor." Chimeric antigen receptors are distinguished from other antigen binding agents by their ability to both bind MHC-independent antigen and transduce activation signals via their intracellular domain. The extracellular and intracellular portions of a CAR are discussed in more detail below.

The antigen-specific extracellular domain of a chimeric antigen receptor recognizes and specifically binds an antigen, typically a surface-expressed antigen of a malignancy. An antigen-specific extracellular domain specifically binds an antigen when, for example, it binds the antigen with an affinity constant or affinity of interaction (KD) between about 0.1 pM to about 10 µM, preferably about 0.1 pM to about 1 µM, more preferably about 0.1 pM to about 100 nM. Methods for determining the affinity of interaction are known in the art. An antigen-specific extracellular domain suitable for use in a CAR of the present disclosure may be any antigen-binding polypeptide, a wide variety of which are known in the art. In some instances, the antigen-binding domain is a single chain Fv (scFv). Other antibody based recognition domains (cAb VHH (camelid antibody variable domains) and humanized versions thereof, IgNAR VH (shark antibody variable domains) and humanized versions thereof, sdAb VH (single domain antibody variable domains) and "camelized" antibody variable domains are suitable for use. In some instances, T-cell receptor (TCR) based recognition domains such as single chain TCR (scTv, single chain two-domain TCR containing V.alpha.V.beta.) are also suitable for use.

Suitable antigens may include T cell-specific antigens and/or antigens that are not specific to T cells. In a preferred embodiment, an antigen specifically bound by the chimeric antigen receptor of a CAR-T cell, and the antigen for which the CAR-T cell is deficient, is an antigen expressed on a malignant T cell, more preferably an antigen that is overexpressed on malignant T cell in comparison to a non-malignant T cell. A "malignant T cell" is a T cell derived from a T-cell malignancy. The term "T-cell malignancy" refers to a broad, highly heterogeneous grouping of malignancies derived from T-cell precursors, mature T cells, or natural killer cells. Non-limiting examples of T-cell malignancies include T-cell acute lymphoblastic leukemia/lymphoma (T-ALL), T-cell large granular lymphocyte (LGL) leukemia, human T-cell leukemia virus type 1-positive (HTLV-1+) adult T-cell leukemia/lymphoma (ATL), T-cell prolymphocytic leukemia (T-PLL), and various peripheral T-cell lymphomas (PTCLs), including but not limited to angioimmunoblastic T-cell lymphoma (AITL), ALK-positive anaplastic large cell lymophoma, and ALK-negative anaplastic large cell lymophoma. For instance, by way of non-limiting example, CD7, CD5, CD2, CD30, and CD4 may be suitable antigens expressed on a malignant T cell. In one embodiment, a CAR-T cell of the present disclosure comprises an extracellular domain of a chimeric antigen receptor that specifically binds to CD7. In another embodiment, a CAR-T cell of the present disclosure comprises an extracellular domain of a chimeric antigen receptor that specifically binds to CD5. In yet another embodiment, a CAR-T cell of the present disclosure comprises an extracellular domain of a chimeric antigen receptor that specifically binds to CD2. In still another embodiment, a CAR-T cell of the present disclosure comprises an extracellular domain of a chimeric antigen receptor that specifically binds to CD30. In still yet another embodiment, a CAR-T cell of the present disclosure comprises an extracellular domain of a chimeric antigen receptor that specifically binds to CD4.

As described above, in one embodiment the antigen is CD7. CD7 is a T-cell surface membrane-associated glycoprotein. CD7 may be overexpressed in T cell malignancies including T-cell acute lymphoblastic leukemia (T-ALL) and non-Hodgkin's T cell lymphoma (NHL). CAR-T cells of the present disclosure may be used to target malignant T-cells that overexpress CD7.

A chimeric antigen receptor of the present disclosure also comprises an intracellular domain that provides an intracellular signal to the T cell upon antigen binding to the antigen-specific extracellular domain. The intracellular signaling domain of a chimeric antigen receptor of the present disclosure is responsible for activation of at least one of the effector functions of the T cell in which the chimeric receptor is expressed. The term "effector function" refers to a specialized function of a differentiated cell. An effector function of a T cell, for example, may be cytolytic activity or helper activity including the secretion of cytokines. An effector function in a naive, memory, or memory-type T cell may also include antigen-dependent proliferation. Thus the term "intracellular domain" refers to the portion of a CAR that transduces the effector function signal upon binding of an antigen to the extracellular domain and directs the T cell to perform a specialized function. Non-limiting examples of suitable intracellular domains include the zeta chain of the T-cell receptor or any of its homologs (e.g., eta, delta, gamma, or epsilon), MB 1 chain, B29, Fc RIII, Fc RI, and combinations of signaling molecules, such as CD3.zeta. and CD28, CD27, 4-1 BB, DAP-10, OX40, and combinations thereof, as well as other similar molecules and fragments. Intracellular signaling portions of other members of the families of activating proteins may be used, such as Fc.gamma.RIII and Fc.epsilon.RI. While usually the entire intracellular domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular domain is thus meant to include any truncated portion of the intracellular domain sufficient to transduce the effector function signal.

Typically, the antigen-specific extracellular domain is linked to the intracellular domain of the chimeric antigen receptor by a transmembrane domain. A transmembrane domain traverses the cell membrane, anchors the CAR to the T cell surface, and connects the extracellular domain to the intracellular signaling domain, thus impacting expression of the CAR on the T cell surface. Chimeric antigen receptors may also further comprise one or more costimulatory domain and/or one or more spacer. A costimulatory domain is derived from the intracellular signaling domains of costimulatory proteins that enhance cytokine production, proliferation, cytotoxicity, and/or persistence in vivo. A spacer connects (i) the antigen-specific extracellular domain to the transmembrane domain, (ii) the transmembrane domain to a costimulatory domain, (Hi) a costimulatory domain to the intracellular domain, and/or (iv) the transmembrane domain to the intracellular domain. For example, inclusion of a spacer domain between the antigen-specific extracellular domain and the transmembrane domain may affect flexibility of the antigen-binding domain and thereby CAR function. Suitable transmembrane domains, costimulatory domains, and spacers are known in the art.

CAR-T cells encompassed by the present disclosure are deficient in an antigen to which the chimeric antigen receptor specifically binds and are therefore fratricide-resistant. In some embodiments, the antigen of the T cell is modified such that the chimeric antigen receptor no longer specifically binds the modified antigen. For example, the epitope of the antigen recognized by the chimeric antigen receptor may be modified by one or more amino acid changes (e.g., substitutions or deletions) or the epitope may be deleted from the antigen. In other embodiments, expression of the antigen is reduced in the T cell by at least 50%, at least 60%, at least 70%, at least 80%, at least 90% or more. Methods for decreasing the expression of a protein are known in the art and include, but are not limited to, modifying or replacing the promoter operably linked to the nucleic acid sequence encoding the protein. In still other embodiments, the T cell is modified such that the antigen is not expressed, e.g., by deletion or disruption of the gene encoding the antigen. In each of the above embodiments, the CAR-T cell may be deficient in one or preferably all the antigens to which the chimeric antigen receptor specifically binds. Methods for genetically modifying a T cell to be deficient in an antigen are well known in art, and non-limiting examples are provided above. In an exemplary embodiment, CRISPR/cas9 gene editing can be used to modify a T cell to be deficient in an antigen, for example as described in the Methods for Examples 4-8.

CAR-T cells encompassed by the present disclosure may further be deficient in endogenous T cell receptor (TCR) signaling. In various embodiments it may be desirable to decrease or eliminate endogenous TCR signaling in CAR-T cells disclosed herein. For example, decreasing or eliminating endogenous TCR signaling in CAR-T cells may prevent or reduce graft versus host disease (GvHD) when allogenic T cells are used to produce the CAR-T cells. Methods for decreasing or eliminating endogenous TCR signaling are known in the art and include, but are not limited, to modifying a part of the TCR receptor (e.g., the TCR receptor alpha chain (TRAC), etc.). TRAC modification may block TCR mediated signaling. TRAC modification may thus permit the safe use of allogeneic T cells as the source of CAR-T cells without inducing life-threatening GvHD.

Alternatively, or in addition, CAR-T cells encompassed by the present disclosure may further comprise one or more suicide genes. As used herein, "suicide gene" refers to a nucleic acid sequence introduced to a CAR-T cell by standard methods known in the art that, when activated, results in the death of the CAR-T cell. Suicide genes may facilitate effective tracking and elimination of the CAR-T cells in vivo if required. Facilitated killing by activating the suicide gene may occur by methods known in the art. Suitable suicide gene therapy systems known in the art include, but are not limited to, various the herpes simplex virus thymidine kinase (HSV-tk)/ganciclovir (GCV) suicide gene therapy systems or inducible caspase 9 protein. In an exemplary embodiment, a suicide gene is a CD34/thymidine kinase chimeric suicide gene.

In an exemplary embodiment, the disclosure provides a T cell comprising a chimeric antigen receptor that specifically binds CD7, wherein the T cell is deficient in CD7 (e.g., CD7ΔCART7 cell). In non-limiting examples the deficiency in CD7 resulted from (a) modification of CD7 expressed by the T cell such that the chimeric antigen receptor no longer specifically binds the modified CD7, (b) modification of the T cell such that expression of the antigen is reduced in the T cell by at least 50%, at least 60%, at least 70%, at least 80%, at least 90% or more, or (c) modification of the T cell such that CD7 is not expressed (e.g., by deletion or disruption of the gene encoding CD7). In further embodiments, the T cell comprises a suicide gene and/or a modification such that endogenous T cell receptor (TCR) mediated signaling is blocked in the T cell. In non-limiting examples the suicide gene expressed in the CD7ΔCART7 cells encodes a modified Human-Herpes Simplex Virus-1-thymidine kinase (TK) gene fused in-frame to the extracellular and transmembrane domains of the human CD34 cDNA and the modification resulting in blocked TCR is a modification to endogenous T-cell Receptor Alpha Chain (TRAC).

In another exemplary embodiment, the disclosure provides a T cell comprising a chimeric antigen receptor that specifically binds CD5, wherein the T cell is deficient in CD5 (e.g., CD5ΔCART5 cell). In non-limiting examples the deficiency in CD5 resulted from (a) modification of CD5 expressed by the T cell such that the chimeric antigen receptor no longer specifically binds the modified CD5, (b) modification of the T cell such that expression of the antigen is reduced in the T cell by at least 50%, at least 60%, at least 70%, at least 80%, at least 90% or more, or (c) modification of the T cell such that CD5 is not expressed (e.g., by deletion or disruption of the gene encoding CD5). In further embodiments, the T cell comprises a suicide gene and/or a modification such that endogenous T cell receptor (TCR) mediated signaling is blocked in the T cell. In non-limiting examples the suicide gene expressed in the CD5ΔCART5 cells encodes a modified Human-Herpes Simplex Virus-1-thymidine kinase (TK) gene fused in-frame to the extracellular and transmembrane domains of the human CD34 cDNA and the modification resulting in blocked TCR is a modification to endogenous T-cell Receptor Alpha Chain (TRAC).

In another exemplary embodiment, the disclosure provides a T cell comprising a chimeric antigen receptor that specifically binds CD2, wherein the T cell is deficient in CD2 (e.g., CD2ΔCART2 cell). In non-limiting examples the deficiency in CD2 resulted from (a) modification of CD2 expressed by the T cell such that the chimeric antigen receptor no longer specifically binds the modified CD2, (b) modification of the T cell such that expression of the antigen is reduced in the T cell by at least 50%, at least 60%, at least 70%, at least 80%, at least 90% or more, or (c) modification of the T cell such that CD2 is not expressed (e.g., by deletion or disruption of the gene encoding CD2). In further embodiments, the T cell comprises a suicide gene and/or a modification such that endogenous T cell receptor (TCR) mediated signaling is blocked in the T cell. In non-limiting examples the suicide gene expressed in the CD2ΔCART2 cells encodes a modified Human-Herpes Simplex Virus-1-thymidine kinase (TK) gene fused in-frame to the extracellular and transmembrane domains of the human CD34 cDNA and the modification resulting in blocked TCR is a modification to endogenous T-cell Receptor Alpha Chain (TRAC).

In another exemplary embodiment, the disclosure provides a T cell comprising a chimeric antigen receptor that specifically binds CD30, wherein the T cell is deficient in CD30 (e.g., CD30ΔCART30 cell). In non-limiting examples the deficiency in CD30 resulted from (a) modification of CD30 expressed by the T cell such that the chimeric antigen receptor no longer specifically binds the modified CD30, (b) modification of the T cell such that expression of the antigen is reduced in the T cell by at least 50%, at least 60%, at least 70%, at least 80%, at least 90% or more, or (c) modification of the T cell such that CD30 is not expressed (e.g., by deletion or disruption of the gene encoding CD30). In further embodiments, the T cell comprises a suicide gene and/or a modification such that endogenous T cell receptor (TCR) mediated signaling is blocked in the T cell. In non-limiting examples the suicide gene expressed in the CD30ΔCART30 cells encodes a modified Human-Herpes Simplex Virus-1-thymidine kinase (TK) gene fused in-frame to the extracellular and transmembrane domains of the human CD34 cDNA and the modification resulting in blocked TCR is a modification to endogenous T-cell Receptor Alpha Chain (TRAC).

In another exemplary embodiment, the disclosure provides a T cell comprising a chimeric antigen receptor that specifically binds CD4, wherein the T cell is deficient in CD4 (e.g., CD4ΔCART4 cell). In non-limiting examples the deficiency in CD4 resulted from (a) modification of CD4 expressed by the T cell such that the chimeric antigen receptor no longer specifically binds the modified CD4, (b) modification of the T cell such that expression of the antigen is reduced in the T cell by at least 50%, at least 60%, at least 70%, at least 80%, at least 90% or more, or (c) modification of the T cell such that CD4 is not expressed (e.g., by deletion or disruption of the gene encoding CD4). In further embodiments, the T cell comprises a suicide gene and/or a modification such that endogenous T cell receptor (TCR) mediated signaling is blocked in the T cell. In non-limiting examples the suicide gene expressed in the CD4ΔCART4 cells encodes a modified Human-Herpes Simplex Virus-1-thymidine kinase (TK) gene fused in-frame to the extracellular and transmembrane domains of the human CD34 cDNA and the modification resulting in blocked TCR is a modification to endogenous T-cell Receptor Alpha Chain (TRAC).

Methods for CAR design, delivery and expression in T cells, and the manufacturing of clinical-grade CAR-T cell populations are known in the art. See, for example, Lee et al., *Clin. Cancer Res.*, 2012, 18(10): 2780-90, hereby incorporated by reference in its entirety. For example, the engineered CARs may be introduced into T cells using retroviruses, which efficiently and stably integrate a nucleic acid sequence encoding the chimeric antigen receptor into the target cell genome. An exemplary method for the viral vector production is described in the Methods to Example 4-8. Other methods known in the art include, but are not limited to, lentiviral transduction, transposon-based systems, direct RNA transfection, and CRISPR/Cas systems (e.g., type I, type II, or type III systems using a suitable Cas protein such Cas3, Cas4, Cas5, Cas5e (or CasD), Cas6, Cas6e, Cas6f, Cas7, Cas8a1, Cas8a2, Cas8b, Cas8c, Cas9, Cas10, Casl Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966, etc.).

CAR-T cells may be generated from any suitable source of T cells known in the art including, but not limited to, T cells collected from a subject. The subject may be a patient with a T cell malignancy in need of CAR-T cell therapy or a subject of the same species as the subject with the T cell malignancy in need of CAR-T cell therapy. The collected T cells may be expanded ex vivo using methods commonly known in the art before transduction with a CAR to generate a CAR-T cell.

The use of autologous T cells for the generation of CAR-T cells, while possible, may present unique challenges. The subjects in need of CAR-T cell therapy may be undergoing treatment for malignancies and this treatment may have affected the number and function of T cells of the host, thereby reducing the number of T cells that may be efficiently engineered into CAR-T cells. Also T-cell hematologic malignancies and normal T effectors may co-express many of the same surface antigens making it very difficult to purify normal T effectors away from the malignant T cells for genetic editing and lentiviral transduction. Also, if the process of purification is not absolute, there may be a risk of deleting the target antigen such as CD7 in the malignant T cells resulting in the generation of a population of contaminating T cell cancers that are potentially resistant to the fratricide CAR-T cell. Thus to avoid contamination risk of normal effector T cells with malignant T cell, the use of patient-derived T cells to generate CAR-T cells for T cell malignancies may not be desirable.

To overcome the contamination risk, T cells from another subject (a donor subject), without T cells malignancies may be used to generate CAR-T cells for allogeneic therapy. The T cells for allogeneic therapy may be collected from a single subject or multiple subjects. Methods of collecting blood cells, isolating and enriching T cells, and expanding them ex vivo may be by methods known in the art.

In an exemplary embodiment, the CAR for a CD7 specific CAR T-cell may be generated by cloning a commercially synthesized anti-CD7 single chain variable fragment (scFv) into a $3^{rd}$ generation CAR backbone with CD28 and 4-1 BB internal signaling domains. An extracellular hCD34 domain may be added after a P2A peptide to enable both detection of CAR following viral transduction and purification using anti-hCD34 magnetic beads. An exemplary method of generating a CAR specific for CD7 is described in the methods for Examples 4-8. A similar method may be followed for making CARs specific for other malignant T cell antigens.

In a further aspect, a CAR-T cell control may be created. The control CAR-T cell may include an extracellular domain that binds to an antigen not expressed on a malignant T-cell. The antigen the control CAR-T cell control binds to may be CD19. CD19 is an antigen expressed on B cells but not on T cells, so a CAR-T cell with an extracellular domain adapted to bind to CD19 will not bind to T cells. These CAR-T cells may be called CART19 cells and may be used as controls to analyze the binding efficiencies and non-specific binding of CART7 cells.

II. Method of Using Car-T Cells

In another aspect, the present disclosure provides a method of killing a malignant T cell, the method comprising contacting the malignant T cell with an effective amount of a T cell comprising a chimeric antigen receptor (CAR-T cell), wherein the CAR-T cell is deficient in an antigen to which the chimeric antigen receptor specifically binds, and wherein the chimeric antigen receptor specifically binds an antigen expressed on a malignant cell. In various embodiments, the malignant cell is a malignant T cell. In further embodiments, the antigen is CD4, CD5, CD7, CD30, or any combination thereof. Suitable CAR-T cells are described in detail in Section I. In exemplary embodiments, the CAR-T cells may be CD7ΔCART7 cells, CD5ΔCART5 cells, CD30ΔCART30 cells, CD4ΔCART4 cells, or any combination thereof.

Contacting a malignant cell with an effective amount of a CAR-T cell generally involves admixing the CAR-T cell and the malignant cell for a period of time sufficient to allow the chimeric antigen receptor of the CAR-T cell to bind its cognate antigen on the surface of the malignant cell. This may occur in vitro or ex vivo. The term "effective amount", as used herein, means an amount that leads to measurable effect, e.g., antigen-dependent cell proliferation, cytokine secretion, cytotoxic killing, etc. The effective amount may be determined by using the methods known in the art and/or described in further detail in the examples.

In another aspect, the present disclosure provides a method for treating a subject having a T cell malignancy. In some embodiments, the T cell malignancy is a hematological malignancy. In some embodiments, the T cell malignancy is T cell acute lymphoblastic leukemia (T-ALL) or T cell non-Hodgkin Lymphomas (T-NHL). The method comprises administering to the subject a therapeutically effective amount of plurality of chimeric antigen receptor T (CAR-T) cells, each CAR-T cell comprising the same chimeric antigen receptor, wherein the CAR-T cells are deficient in an antigen specifically recognized by the chimeric antigen receptor, and wherein the chimeric antigen receptor specifically binds an antigen expressed on a malignant T cell. In various embodiments, the antigen may be CD4, CD5, CD7, CD30, or any combination thereof. Suitable subjects include any mammal, preferably a human. Suitable CAR-T cells are described in detail in Section I. In exemplary embodiments, the CAR-T cells may be CD7ΔCART7 cells, CD5ΔCART5 cells, CD30ΔCART30 cells, CD4ΔCART4 cells, or any combination thereof. The method may comprise allogenic CAR-T cell therapy or autologous CAR-T cell therapy, though allogenic CAR-T cell therapy may be preferred for the reasons discussed in Section I. The CAR-T cell therapy may be accompanied by other therapies, including but not limited to immunotherapy, chemotherapy or radiation therapy.

In another aspect, the present disclosure provides a method for treating a subject having a non-T cell myeloid or lymphoid malignancy. The method comprises administering to the subject a therapeutically effective amount of a plurality of chimeric antigen receptor T (CAR-T) cells, each CAR-T cell comprising the same chimeric antigen receptor, wherein the CAR-T cells are deficient in an antigen specifically recognized by the chimeric antigen receptor, and wherein the chimeric antigen receptor specifically binds an antigen expressed on the non-T cell myeloid or lymphoid malignancy. Suitable subjects include any mammal, preferably a human. Suitable CAR-T cells are described in detail in Section I. In an exemplary embodiment the CAR-T cells are CD7ΔCART7 cells. The method may comprise allogenic CAR-T cell therapy or autologous CAR-T cell therapy, though allogenic CAR-T cell therapy may be preferred for the reasons discussed in Section I. The CAR-T cell therapy may be accompanied by other therapies, including but not limited to immunotherapy, chemotherapy or radiation therapy.

In another aspect, the present disclosure provides a method for preventing or reducing graft versus host disease in subject in need of CAR-T cell therapy. In some embodiment, the subject in need of CAR-T cell therapy is a subject with a T-cell malignancy, a non-T cell myeloid malignancy, or lymphoid malignancy. The method comprises administering to the subject a therapeutically effective amount of a plurality of chimeric antigen receptor T (CAR-T) cells, each CAR-T cell comprising (a) the same chimeric antigen receptor and (b) a suicide gene and/or a modification such that endogenous T cell receptor (TCR) mediated signaling is blocked in the CAR-T cell; wherein the CAR-T cells are deficient in an antigen specifically recognized by the chimeric antigen receptor, and wherein the chimeric antigen receptor specifically binds an antigen expressed on the malignancy. In various embodiments, the malignant cell is a malignant T cell. In further embodiments, the antigen is CD4, CD5, CD7, CD30, or any combination thereof. Suitable subjects include any mammal, preferably a human. The method may comprise allogenic CAR-T cell therapy or autologous CAR-T cell therapy, though allogenic CAR-T cell therapy may be preferred for the reasons discussed in Section I. The CAR-T cell therapy may be accompanied by other therapies, including but not limited to immunotherapy, chemotherapy or radiation therapy.

In another aspect, the present disclosure provides a method for preventing or reducing alloreactivity in a subject in need of allogenic CAR-T cell therapy. In some embodiment, the subject in need of allogenic CAR-T cell therapy is a subject with a T-cell malignancy, a non-T cell myeloid malignancy, or lymphoid malignancy. The method comprises administering to the subject a therapeutically effective amount of a plurality of chimeric antigen receptor T (CAR-T) cells, each CAR-T cell comprising (a) the same chimeric antigen receptor and (b) a suicide gene and/or a modification such that endogenous T cell receptor (TCR) mediated signaling is blocked in the CAR-T cell; wherein the CAR-T cells are deficient in an antigen specifically recognized by the chimeric antigen receptor, and wherein the chimeric antigen receptor specifically binds an antigen expressed on the malignancy. In various embodiments, the malignant cell is a malignant T cell. In further embodiments, the antigen is CD4, CD5, CD7, CD30, or any combination thereof. Suitable subjects include any mammal, preferably a human. The CAR-T cell therapy may be accompanied by other therapies, including but not limited to immunotherapy, chemotherapy or radiation therapy.

In various embodiments of the above aspects, the plurality of CAR-T cells may be a plurality of CD7ΔCART7 cells, a plurality of CD5ΔCART5 cells, a plurality of CD30ΔCART30 cells, a plurality of CD4ΔCART4 cells, or any combination thereof. In further embodiments, the CAR-T cells may comprise a suicide gene and/or a modification such that endogenous T cell receptor (TCR) mediated signaling is blocked in the CAR-T cell.

CAR-T cells may be administered to a subject by an intravenous route, for instance, by an intravenous infusion. The CAR-T cells may be administered in a single dose or in multiple doses. The CAR-T cells may be injected in a pharmaceutical composition suitable for intravenous administration. Suitable pharmaceutical compositions for IV administration are known in the art. A pharmaceutical composition of the present disclosure may further comprise additional components. For instance, such components may be used to sustain the viability and/or activity of injected CAR-T cells. In one embodiment, the CAR-T cell composition may include IL-2 to sustain the CAR-T cells.

The CAR-T cells may be administered in effective doses. The effective dose may be either one or multiple doses, and are sufficient to produce the desired therapeutic effect. A typical dose of CAR-T cells may range from about $1 \times 10^5$-$5 \times 10^7$ cells/Kg body weight of subject receiving therapy. The effective dose may be calculated based on the stage of the malignancy, the health of the subject, and the type of malignancy. In the situation where multiple doses are administered, that dose and the interval between the doses may be determined based on the subject's response to therapy.

An "effective dose" or "therapeutically effective amount" as used herein, means an amount which provides a therapeutic or prophylactic benefit.

The term "therapeutic effect" as used herein, refers to a biological effect which can be manifested by a decrease in the number of malignant cells, an increase in life expectancy, or amelioration of various physiological symptoms associated with the malignant condition, etc.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

T cell malignancies represent a class of devastating hematologic cancers with high rates of relapse and mortality in both children and adults for which there are currently no effective or targeted therapies. Despite intensive multi-agent chemotherapy regimens, fewer than 50% of adults and 75% of children with T cell acute lymphoblastic leukemia (T-ALL) survive beyond five years. For those who relapse after initial therapy, salvage chemotherapy regimens induce remissions in 20-40% of cases. Allogeneic stem cell transplant, with its associated risks and toxicities, is the only curative therapy.

T cells engineered to express a chimeric antigen receptor (CAR) are a promising cancer immunotherapy. Such targeted therapies have shown great potential for inducing both remissions and even long-term relapse free survival in patients with B cell leukemia and lymphoma. Thus, a targeted therapy against T cell malignancies represents a significant unmet medical need. However, several challenges have limited the clinical development of CAR-T cells against T cell malignancies. First, the shared expression of target antigens between T effector cells and T cell malignancies results in fratricide, or self-killing, of CAR-T cells. Second, harvesting adequate numbers of autologous T cells, without contamination by malignant cells is, at best, technically challenging and prohibitively expensive. Third, the use of genetically modified CAR-T cells from allogeneic donors may result in life-threatening graft-vs.-host disease (GvHD) when infused into immune-compromised HLA-matched or mismatched recipients.

Many T cell malignancies overexpress CD7, providing an attractive target for immunotherapy of T cell cancers. However, normal T cells, including those used to engineer CAR-T, also express CD7 (>86%). Thus, CD7-targeted CAR-T cells induce T cell fratricide, limiting therapeutic potential. It was hypothesized that deletion of CD7 and the T cell receptor alpha chain (TRAC) using CRISPR/Cas9 while also transducing these same T cells with a CD7 targeting CAR would result in the efficient targeting and killing of malignant T cells without significant effector T cell fratricide. TRAC deletion blocks TCR mediated signaling, permitting the safe use of allogeneic T cells as the source of CAR-T without inducing life-threatening GvHD and without risk of contamination by CD7-deleted malignant cells, resistant to CART7 therapy. Using high efficiency CRISPR/Cas9 gene-editing, CD7 and TRAC-deleted CAR-T targeting CD7 (UCART7) were generated. These UCART7 cells efficiently kill human T-ALL cell lines and patient-derived primary T-ALL in vitro and in vivo without resulting in xenogeneic GvHD. Accordingly, for the first time, preclinical data for an "off-the-shelf" strategy to effectively treat T cell malignancies using CAR-T therapy is presented.

Example 1: Gene Editing of CAR-T Cells

T-cells can be genetically modified to express chimeric antigen receptors (CARs). which are fusion proteins comprised of an antigen recognition moiety and T-cell activation domains. CAR-T cells demonstrate exceptional clinical efficacy against B cell malignancies. However, the development of CAR-T therapy against T cell malignancies has proven problematic, in part due the expression of target antigens shared between T cell malignancies and effector T cells. Expression of target antigens on CAR-T cells may induce fratricide of CAR-T and loss of efficacy, and also reduce clinical benefit. Through gene editing of CAR-T it was demonstrated that efficient deletion of T cell-specific target antigens that are normally expressed on CAR-T (and T cell malignancies) can result in the effective expansion of CAR-T without significant "fratricide" and effective killing of tumor targets using gene edited CAR-T cells. The development of a T cell product that has CD7 bi-allelically deleted and which overexpresses a CD7-CAR in T cells that have been gene edited to delete CD7 (FIG. 1) is described. This approach can be extended to encompass other T cell antigens such as CD5, CD4, and CD2 that are expressed on various T cell cancers and on normal T cells. In addition, the incorporation of a suicide gene in lentiviral and retroviral constructs expressing CARs will not only be used to protect against both insertional mutagenesis and leukemogeneis but also against long term T cell and NK cell cytopenias.

Example 2: Gene Editing of the CD7 Locus Resulted in Loss of CD7 Expression

Figure 2:
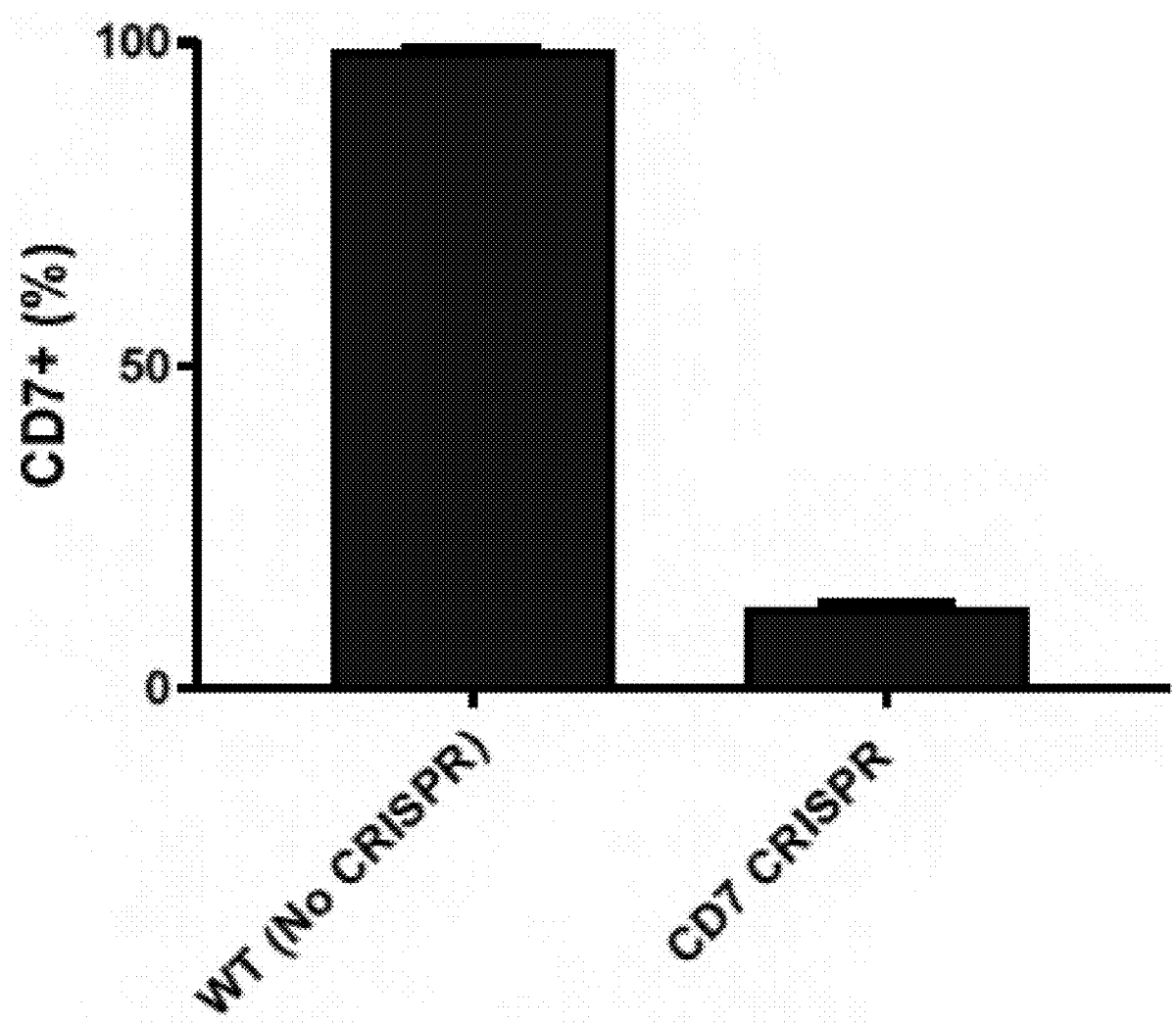
FIG. 2 shows the gene editing of the CD7 locus results in loss of CD7 expression in >90% of T cells compared to wild-type (WT) T cells.

The adhesion molecule CD7 is highly expressed on T-ALL (T acute lymphoblastic leukemia; 98%) and other T cell malignancies and proves to be an attractive target for immunotherapy of T cell cancers. CD7, however, is highly expressed on activated T cells (>86%). CRISPR/Cas9 was used to delete CD7 expression on CAR-T cells. Guide RNAs (gRNA) targeting hCD7 were designed and validated for activity by the Washington University genome engineering core. The gRNA with the greatest activity was commercially synthesized, incorporating modified bases (2'Ome and phosphorothiate) to increase gRNA stability. To generate the CD7 CAR, the anti-CD7 single chain variable fragment (scFv) was created using commercial gene synthesis and cloned into a backbone of a 3rd generation CAR with CD28 and 4-1 BB internal signaling domains (provided by Dr. C. June, University of Pennsylvania). The construct was modified to express a cytoplasmic truncation mutant of human CD34 (or the CD34-TK75 chimeric suicide gene; Eissenberg et al *Molecular Therapy*, 2015) via a P2A peptide to enable detection of CAR following viral transduction. Human primary T cells were activated using anti-CD3/CD28 beads for 48 hours prior to bead removal and electroporation with CD7 gRNA (20 µg) and Cas9 mRNA (15 µg). T cells were then rested for 24hrs. On day three, T cells were transduced with lentivirus particles encoding either CD7-CAR, CD7-CAR-P2A-CD34, CD7-CAR-P2A-CD34-TK75, or control CD19-CAR and allowed to expand for a further 6 days. Transduction efficiency and CD7 ablation was confirmed by flow cytometry. Gene editing of the CD7 locus resulted in loss of CD7 expression in >90% of T cells compared to control T cells (FIG. 2).

Example 3: CD7 CAR-T Cells Effectively Kill CD7 Positive T-ALL Cells In Vitro

Figure 3A:
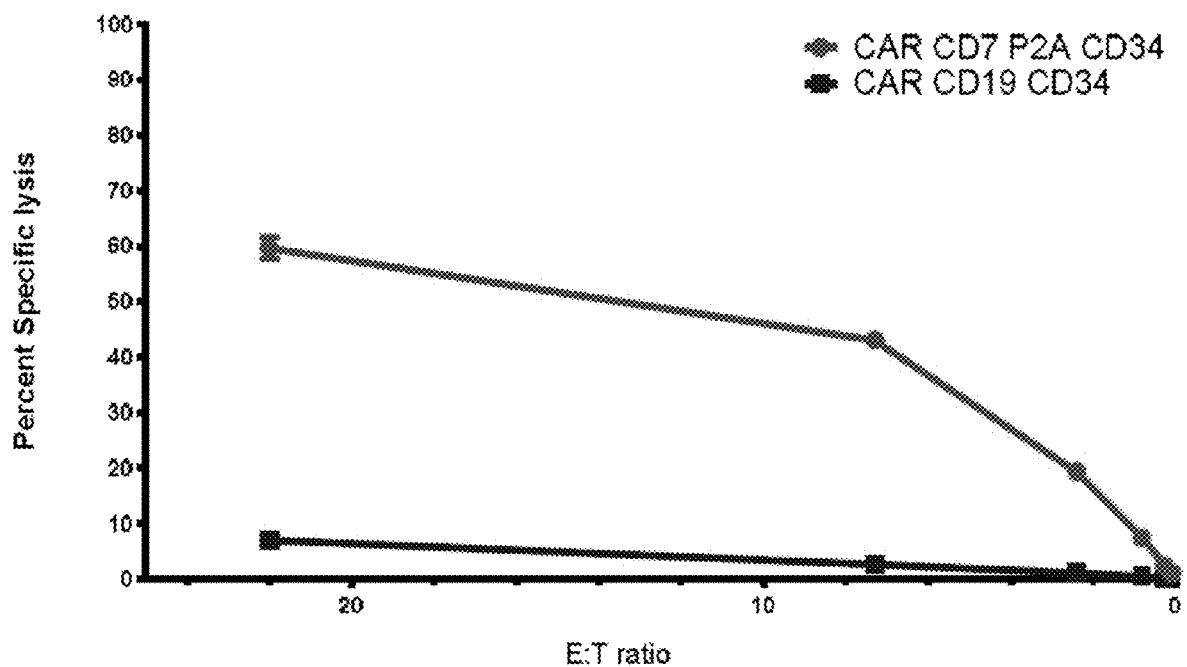
FIG. 3A illustrates CD7 gene edited CD7 CAR-T (CD7ΔCART7) cells effectively kill CD7 positive MOLT 3 cells of T cell acute lymphoblastic leukemia cells in vitro.
Figure 3B:
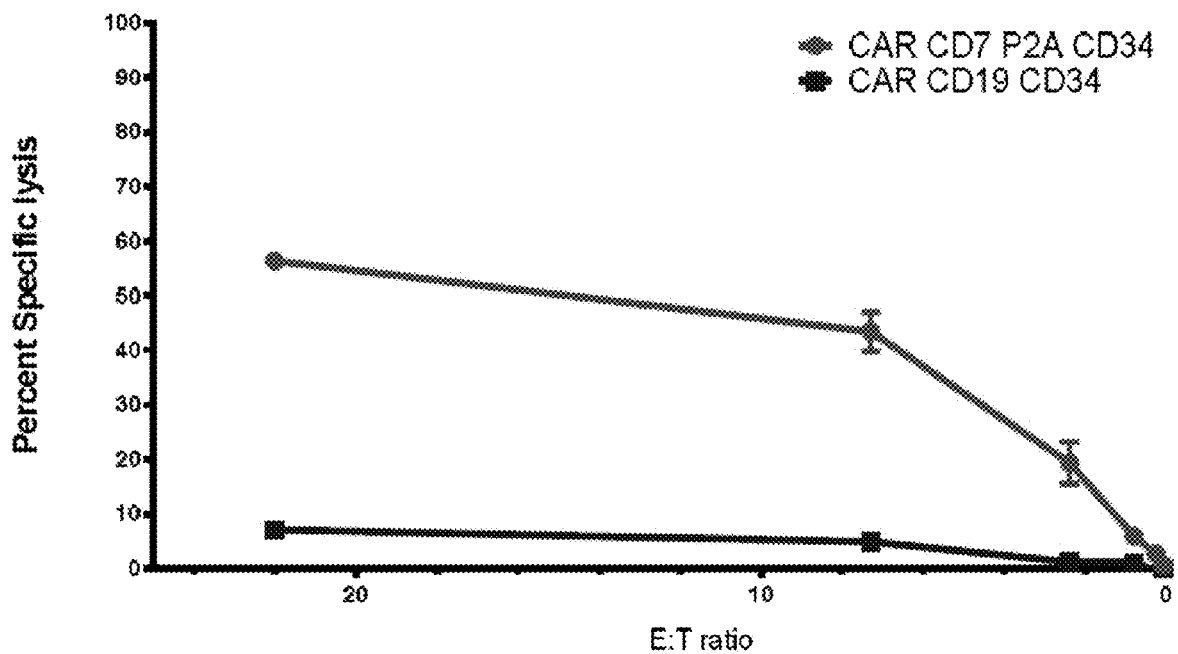
FIG. 3B CD7ΔCART7 effectively kill CD7 positive HSB-2 cells of T cell acute lymphoblastic leukemia cells in vitro.
Figure 4A:
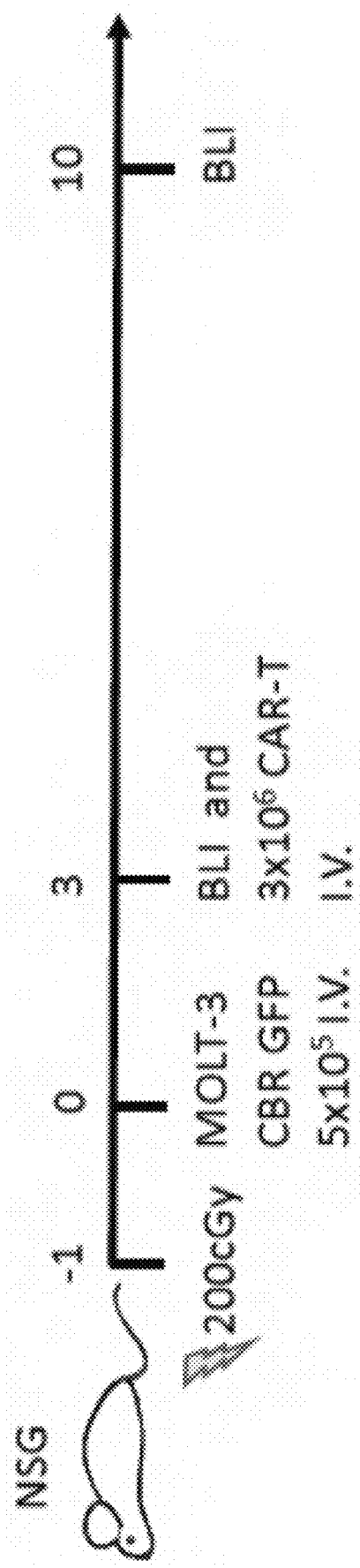
FIG. 4A-FIG. 4D illustrates that CD7ΔCART7 effectively kill CD7 positive T cell acute lymphoblastic leukemia cells in vivo.
Figure 4B:
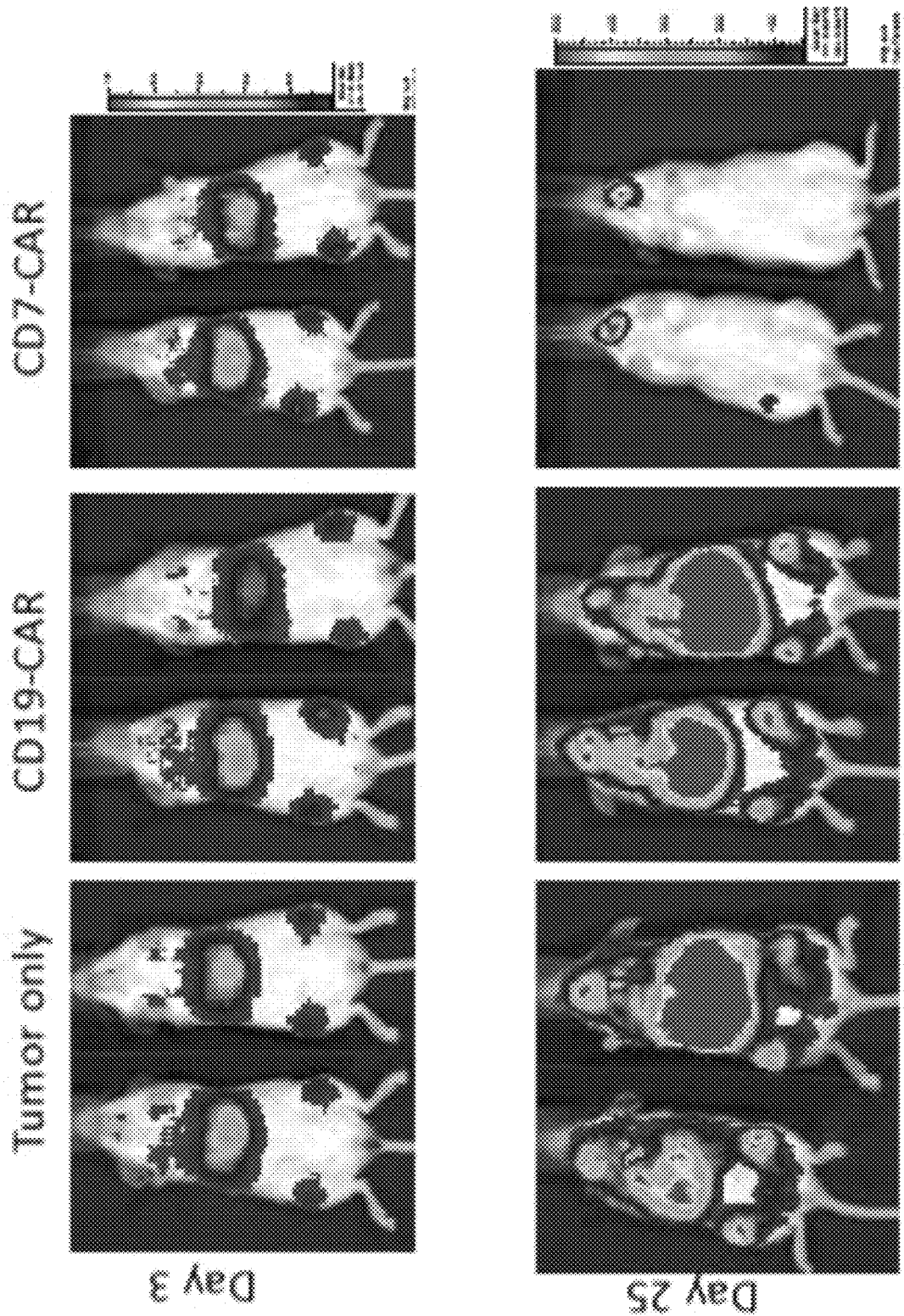
Figure 4C:
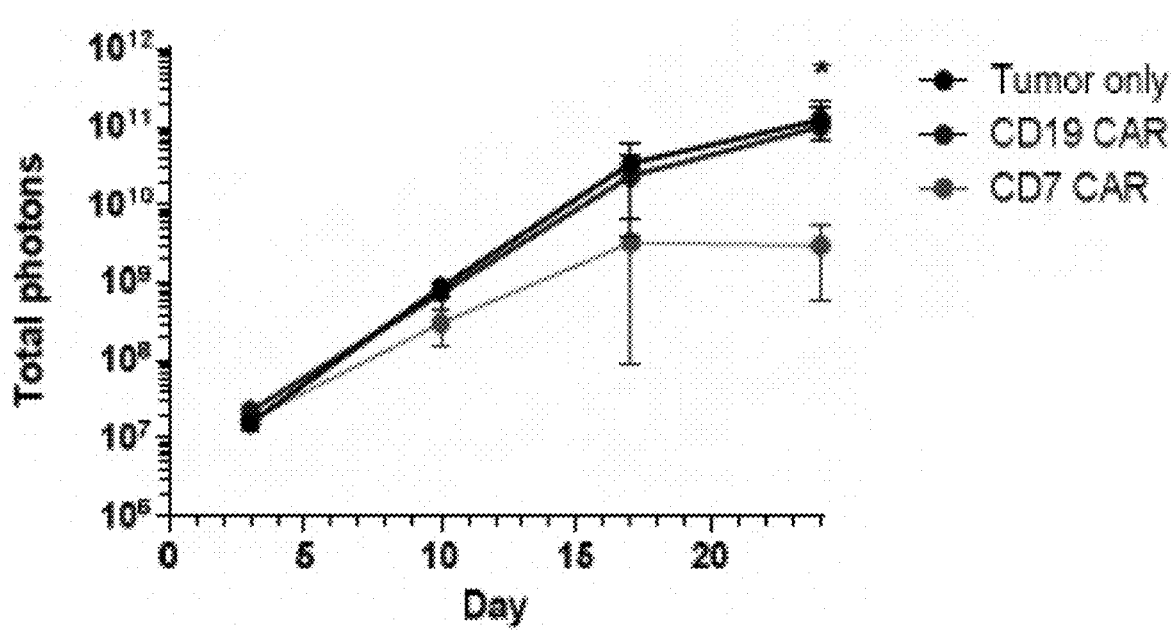
Figure 4D:
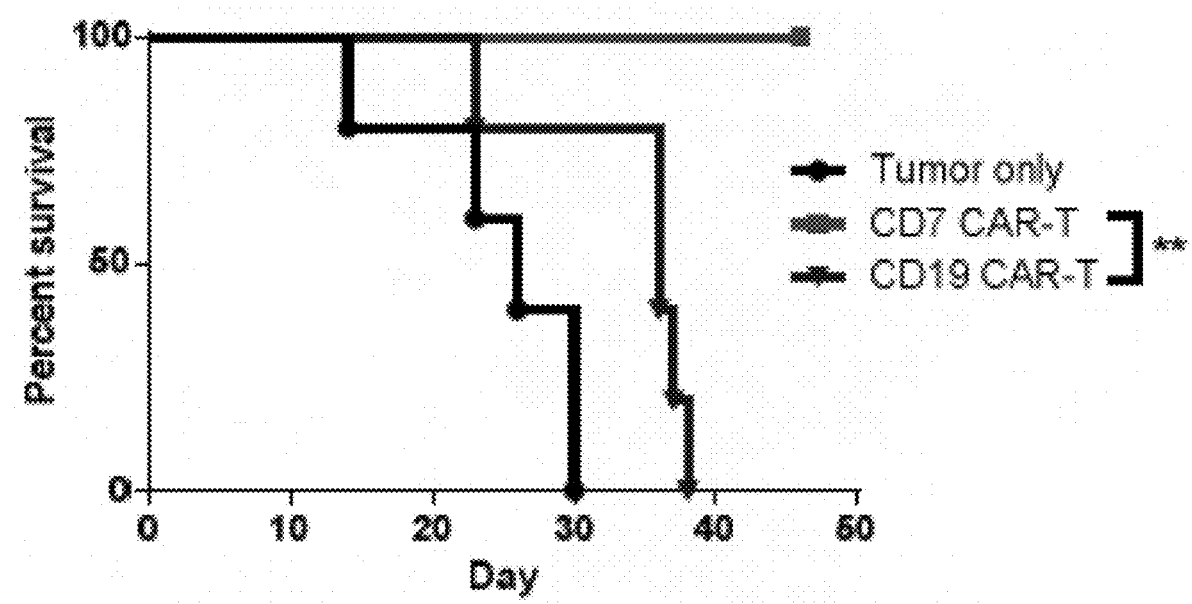

The ability of gene edited (CD7 deleted) CD7 CAR-T cells to target CD7+ T-ALL cell lines in vitro was tested. In contrast to the CD19 CAR-T cells, CD7 CAR-T cells effectively killed the CD7+ cell lines MOLT-3 and HSB-2 as determined by a 4 hr chromium release assay (FIG. 3). The ability of CD7 deleted CD7 CAR-T to eradicate T-ALL in vivo was tested. NSG mice were sub-lethally irradiated (200cGy) prior to infusion of $5 \times 10^5$ MOLT-3 T-ALL cells modified to express CBR (click beetle red) luciferase. A single dose of CAR-T ($3 \times 10^6$) were injected i.v. on day 3. Mice receiving CD7 CAR-T cells had a significantly reduced tumor burden compared to mice receiving CD19 CAR-T cells as assessed by bioluminescent imaging. Furthermore, mice receiving CD7 CAR-T cells survived significantly longer than mice treated with CD19 CAR-T cells (p=0.0018, FIG. 4). These data support T cell adoptive therapy in combination with genome editing as a promising therapy for targeting T-ALL.

Methods for Examples 4-8

CAR Design

CD7-CAR was generated by using commercial gene synthesis of an Anti-CD7 single chain variable fragment (scFv) and cloned into a backbone of a 3rd generation CAR with CD28 and 4-1 BB internal signaling domains. The Ef1α pELNS lentiviral plasmid was a kind gift from Dr. Carl June (University of Pennsylvania). The construct was modified to express the extracellular domain of hCD34 via a P2A peptide to enable both detection of CAR following viral transduction and, if required, purification of CAR-T using anti-hCD34 magnetic beads. CART19 were used as a non-targeting control.

Viral Vector Production

To produce lentivirus, the Lenti-X 293T Cell Line (Takara Bio, Mountain View, CA) was transfected with CAR lentiviral vector and the packaging plasmids, pMD.Lg/pRRE, pMD.G, pRSV.Rev 1,2 using the CalPhos™ Mammalian Transfection Kit (Takara) per the manufactures instructions. Virus was harvested 36 hrs post transfection, filtered to remove cell debris, and concentrated by ultracentrifugation for 90 mins at 25 000 rpm, 4o C (Optima LE-80K Ultracentrifuge, Beckman Coulter, Indianapolis IN). Virus was re-suspended in phosphate buffered saline, snap frozen in liquid nitrogen and stored at −80° C. in single use aliquots.

CRISPR/cas9 Gene Editing

Guide RNA were designed and validated for activity by Washington University Genome Engineering & iPSC (SEQ ID NOS: 7-16). Plasmids encoding gRNA (400 ng, Addgene 43860) and spCas9 (500 ng, Addgene 43945) were electroporated into the leukemia cell line, K562, using the nucleofector 4D (Lonza NJ) in 20 μl solution P3 (program FF-120).

RNA guides were commercially synthesized (Trilink Biotechnologies San Diego, CA), incorporating 2'-O-methyl and 3' phosphorothioate bases at the three terminal bases of the 5' and 3' ends of the gRNA to protect from nuclease activity. SEQ ID NO 17-19 are full guide sequences. Streptococcus pyogenes Cas9 (spCas9) mRNA (5meC, Ψ) was purchased from Trilink Biotechnologies.

Gene Edited CAR-T

T cells were cultured in Xcyte media supplemented with 50 U/mL IL-2 and 10 ng/ml IL-15 in the presence of anti-CD3/CD28 beads (Bead to cell ratio 3:1). On day +2 post activation, beads were removed and $4 \times 10^6$ T cells were electroporated in 100 μl buffer P3 with 15 μg spCas9 (Trilink, CA) and 20 μg of each gRNA (Trilink) using anucleofector 4D, program EO-115. Cells were transduced with CAR7 or CAR19 (control) lentiviral particles in the presence of polybrene (Sigma Aldrich. St Louis MO) (final conc. 6 μg/ml) on day +3. Cells were expanded for an additional 6 days prior to use in downstream experiments.

Targeted Deep Sequencing

The CD7 locus was amplified with primers forward primer GCCTGCGTGGGATCTACCTGAGGCA [SEQ ID NO: 1], and reverse primer AGCTATCTAG-GAGGCTGCTGGGGGC [SEQ ID NO: 2]. The TRAC Locus was amplified with forward primer TGGGGCAAAGAGGGAAATGA [SEQ ID NO: 3], and reverse primer R_GTCAGATTTGTTGCTCCAGGC [SEQ ID NO: 4]. PCR products were sequenced using the Illumia MiSeq platform (San Diego, CA). Editing efficiencies were determined as a percentage of sequencing reads with indels aligned to reads obtained from WT cells.

Cell Lines

CD7 positive T-ALL cell lines, MOLT-3 (ACC 84), MOLT-4 (ACC 362), HSB-2 (ACC 435) and CCRF-CEM (ACC 240) were obtained from directly from DSMZ-German collection of Microorganisms and Cell cultures (Leibniz, Germany). The cell lines were mycoplasma tested and characterized by DSMZ. CCRF-CEM cells were transduced with EF1αCBR-GFP lentivirus. GFP positive cells were sorted and cloned to establish the CCRF-CEMCBR-GFP cell line.

Chromium Release Assay

CAR-T were incubated with MOLT-3, MOLT4, HSB2 or CCRF cell lines ($4 \times 10^4$ total cells/well) at an effector:target [E:T] ratio ranging from 25:1 to 0.25:1 in RPMI supplemented with 5% fetal calf serum. Chromium-51 release assays were performed as described previously.

In Vitro Primary T-ALL Killing Assay

Primary T-ALL from consented patients were obtained from the Siteman Cancer Center (IRB #201108251). Informed consent was obtained from all subjects. Primary cells were labeled with 150 nM carboxyfluorescein succinimidyl ester (CFSE) (Sigma Aldrich, MO) to enable distinction between T-ALL blasts and CAR-T. Labeled cells were co-incubated at 1:1 ratio with either CD7ΔCART7, UCART7 or their respective CD19 controls for 24 hours prior to FACS analysis. Absolute cell counts of viable target cells were quantified by flow cytometry using 7-aminoactinomycin D and SPHERO AccuCount fluorospheres (Spherotech Inc., Lake Forest, IL, USA). Data were analyzed using FlowJo V10.

Fratricide Assay

WT T cells were cultured in Xcyte media supplemented with 50 U/mL IL-2 and 1 Ong/ml IL15 in the presence of anti-CD3/CD28 beads (bead to cell ratio 3:1). Beads were removed after 48 hours and T cell were transduced with lentivirus particles to express GFP. Seventy-two hrs. post transduction, T cells were sorted for GFP using flow cytometry and co-incubated with CD7ΔCART7 or CD7ΔCART19 at a ratio of 1:1 for 24 hrs in Xcyte media supplemented with 50 U/mL IL-2 and 1 Ong/ml IL-15, 50 ng/ml SCF, 10 ng/ml IL-7, and 20 ng/ml FL3TL. Percent GFP+ cells were calculated as a percentage of total viable cells, quantified by flow cytometry using 7-aminoactinomycin D.

T Cell Phenotype Analysis

Cultured T cells were washed in PBS/0.1% BSA and re-suspended at $1 \times 10^6$ cells in 50 uL Brilliant Buffer (BD Biosciences) supplemented with 4% rat serum for 15 minutes at 4C. Cells were then incubated for 30 minutes at 4° C. in 100 μL of Brilliant Buffer using the following antibody fluorophore conjugates (all from BD Biosciences unless otherwise noted): CD7 BV421, CD4 BV510, CCR4 BV605 (BioLegend), CD8 BV650, CD196 BV786 (BioLegend), CD3 AF488, CD45RA PerCPCy5.5, CD183 PE, CD197 PE-CF594, CD185 PE-Cy7 (BioLegend), and CCR10 APC (R&D Systems). Full details of flurophore conjugated antibodies are listed in Table 1. Cells were then washed twice in PBS/0.1% BSA and data acquired on a ZE5 (Yeti) cytometer (BioRad/Propel Labs). Compensation and analyses were performed on FlowJo V10 (TreeStar) using fluorescence minus one (FMO) controls. Statistical analyses were performed on Graph Pad Prism 7 using 2-way ANOVA with Bonferroni post-hoc corrections.

TABLE 1

Details of conjugated antibodies used for flow cytometry.

| Antigen | Clone | Fluorochrome | Manufacturer | Catalogue number |
|---|---|---|---|---|
| hCD7 | MT701 | BV421 | BD Biosciences | 562635 |
| hCD4 | SK3 | BV510 | BD Biosciences | 562970 |
| hCD194/CCR4 | L291H4 | BV605 | BioLegend | 359418 |
| hCD8 | RPA-T8 | BV650 | BD Biosciences | 563821 |
| hCD196/CCR6 | G034 | BV785 | BioLegend | 353422 |
| hCD3 | UCHT1 | AF488 | BD Biosciences | 557694 |
| hCD45RA | HI100 | PerCP-Cy5.5 | BD Biosciences | 563429 |
| hCD183/CXCR3 | 1C6 | PE | BD Biosciences | 557185 |
| hCD197/CCR7 | 150503 | PE-CF594 | BD Biosciences | 562381 |
| hCD185/CXCR5 | RF8B2 | PE-Cy7 | BioLegend | 356924 |
| hCCR10 | 314305 | APC | R&D | FAB3478A100 |
| hCD34 | QBEnd10 | PE | Beckman Coulter | IM1250U |
| hCD4 | RPA-T4 (RUO) | APC | BD Biosciences | 555349 |
| hCD8-PECy7 | HIT8a (RUO) | PeCy7 | BD Biosciences | 555635 |
| mCD45-BV510 | 30-F11 | BV510 | BD Biosciences | 563891 |
| hCD45 | 2D1 | APC-H7 | BD Biosciences | 560274 |
| hCD3 | SK7 | APC | eBioScience | 47-0036-42 |

Animal Models

Animal protocols were in compliance with the regulations of Washington University School of Medicine Animal Studies Committee. Six to ten week old NOD.Cg-Prkdcscid 112rgtm1Wjl/SzJ (NSG) were used in all mice experiments. Both male and female mice were used in all experiments and randomly assigned to a treatment group.

CCRF-CEM Xenograft Model

The anti-leukemic effect of the CD7ΔCAR7 was tested in vivo using the T-ALL cell line, CCRF-CEM, modified to over express GFP and click-beetle red luciferase (CBR). NSG mice were injected into the tail vein with $1\times10^5$ CCRF-CEMCBR-GFP on day 0. Both male and female mice were used. CAR-T ($2\times10^6$) were injected into the mice receiving CCRF-CEMCBR-GFP cells on day 1. To track CCRF-CEMCBR-GFP tumor growth in vivo, mice were injected intraperitoneally with 50 μg/g D-luciferin (Biosynth, Itasca, IL, USA) and imaged. Statistical consideration: Log-rank (Mantel-Cox) test was used to determine significant differences in survival. Statistical analysis of tumor burden, as defined by BLI imaging, was determined using two-way ANOVA for repeated measurement data, followed by a step-down Bonferroni adjustment for multiple comparisons.

Patient Derived Xenograft Model

T-ALL POX DFCI12 was obtained from the Public Repository of Xenografts (PRoXe). PRoXe.org. NSG were engrafted with $1\times10^6$ PDX DFC112 cells on day 0 followed by infusion of $2\times10^6$ UCART7, UCART19, TRACΔ1 or WT T on day+1. Peripheral blood and spleens were analyzed by flow cytometry after one week. Red blood cells were lysed using Red Blood Cell Lysing Buffer (Sigma-Aldrich) and washed with ice cold PBS. Samples were prepared for flow cytometry by re-suspending cells in staining buffer (PBS supplemented with 0.5% bovine serum albumin and 2 mM EOTA) and incubating for 30 min at 4° C. with pre-titrated saturating dilutions of the following fluorochrome-labeled monoclonal antibodies; CD34-PE, CD7-BV421, CD4-APC, CD8-PECy7, mCD45-BV510, and hCD45-APC-H7. Full details of the antibodies can be found in Table 1. Antibodies were purchased from BD biosciences unless otherwise stated. Data were analyzed using FlowJo V10.

Off Target Analysis
Genomic Insertion of dsODN

Blunt double-stranded oligodeoxynucleotide double stranded oligonucleotide (dsODN) were prepared by annealing two modified oligonucleotides (Integrated DNA technologies, IA).

Rev_5Phos/A*T*ACCGTTATTAACATATGACAACT-CAATTAA*A*C (SEQ ID NO: 5), and For_/5Phos/G*T*TTAATTGAGTTGTCATATGTTAATAACGGT*A*T* (SEQ ID NO: 6) represents phosphorothioate linkage and 5phos represents 5' phosphorylation. CRISPR/Cas9 gene editing of primary T cells was performed as described previously, but with the addition of 100 pmol dsODN. Cells were cultured for an additional 7 days prior to harvest and DNA extraction (DNAeasy Qiagen GmbH, Germany).

dsODN Capture

Hybrid capture of small discreet genomic loci can prove to be difficult without certain bait design & protocol modifications. Fragments that contain a 34 bp DNA dsODN utilizing modified xGEN Lockdown probes that are complimentary to the inserted dsODN sequence were enriched. The xGen lockdown probes were designed to participate in a competitive hybridization manner to maximize hybrid pull down efficiency. The novel design consists of multiple probes interrogating the tag region with a 2 base offset design. Additionally, the modified xGen Lockdown Probes were designed to enhance target sequence binding to the approximate melting temperature of standard 120 nt DNA xGen Lockdown probes. The streptavidin/biotin-mediated pull down mechanism was modified to augment the result of an enriched subset of gDNA containing the 34 bp tag.

Automated dual indexed libraries were constructed with 250ng of genomic DNA utilizing the KAPA HTP Library Kit (KAPA Biosystems) on the SciClone NGS instrument (Perkin Elmer) targeting 250 bp inserts. The Dual indexed KAPA library primer sequences are SEQ ID NO: 20-SEQ ID NO: 54. Libraries were enriched for eight PCR cycles. Sixteen libraries were pooled pre-capture generating a 5 μg library pool. The library pool was hybridized with a custom set of xGen Lockdown Probes (IDT), targeting the 34 bp ODN sequence. The concentration of the captured library pool was accurately determined through qPCR (KAPA Biosystems) to produce cluster counts appropriate for the Illumina HiSeq4000 platform. 2×150 sequence data generated an average of 3.5 Gb of data per sample.

GUIDE-seq

The 16 existing dual indexed KAPA libraries constructed for the targeted capture experiment were utilized for the Guide-Seq amplifications. PCR reactions were set up with 20ng of existing library per sample, KAPA HiFi Hotstart Readymix (KAPA Biosystems), and 100 primers. PCR conditions were as follows: PCR cycling parameters for library generation
Cocktail for 504 reaction
    25 µL KAPA HiFi Master Mix
    1.0 µL 10 µM P5
    1.5 µL 10 µM GSiP
    x µL 20 ng of existing dual indexed library
    y µL Nuclease-free water
Cycle Conditions
    95° C. for 5 min,
    15 cycles of [95° C. for 30s, 70° C. (−1° C./cycle) for 2 min, 72° C. for 30 s]
    10 cycles of [95° C. for 30s, 55° C. for 1 min, 72° C. for 30 s]
    72° C. for 5min
    4° C. hold GUIDE-seq indexed primers (GSiPs) were designed to target the sense and antisense Guide-seq ODN sequence while incorporating the P7 engraftment sequence and 8 bp sample index.

Thirty-two amplicon libraries (16 sense and 16 anti-sense) were accurately quantitated through qPCR (KAPA Biosystems) to produce cluster counts appropriate for the Illumina HiSeq4000 platform. The amplicon libraries were normalized and pooled together. The amplicon library pool and targeted capture pool were combined in equal molar concentrations prior to generating one lane of HiSeq4000 2×150 sequence data (Illumina).

Data Analysis

Sequence was aligned to the reference genome (build GRCh37-lite) using BWA MEM v0.7.10. A modified version of the guide-seq package was used to identify 10-bp sliding windows where the target sequence was present with at least 10 reads of support. To characterize off-target alignments, 35 bp of reference sequence flanking both sides of the breakpoint was retrieved and aligned with the observed sequence. Sites were required to have at least one supporting read in both the forward and reverse directions to be retained. Any site also identified in one of the control samples was removed. Code availability: The modified guide-seq code is available at github.com/chrisamiller/guideseq.

Example 4: CD7-CAR-T Cells Induce Substantial Fratricide

Figure 5A:
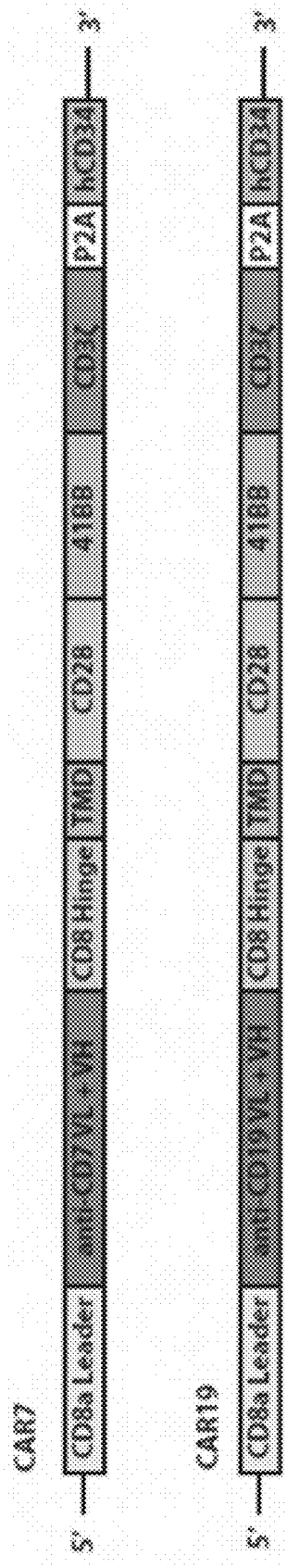
FIG. 5A-FIG. 5J illustrate CART7 induced fratricide.
Figure 5B:
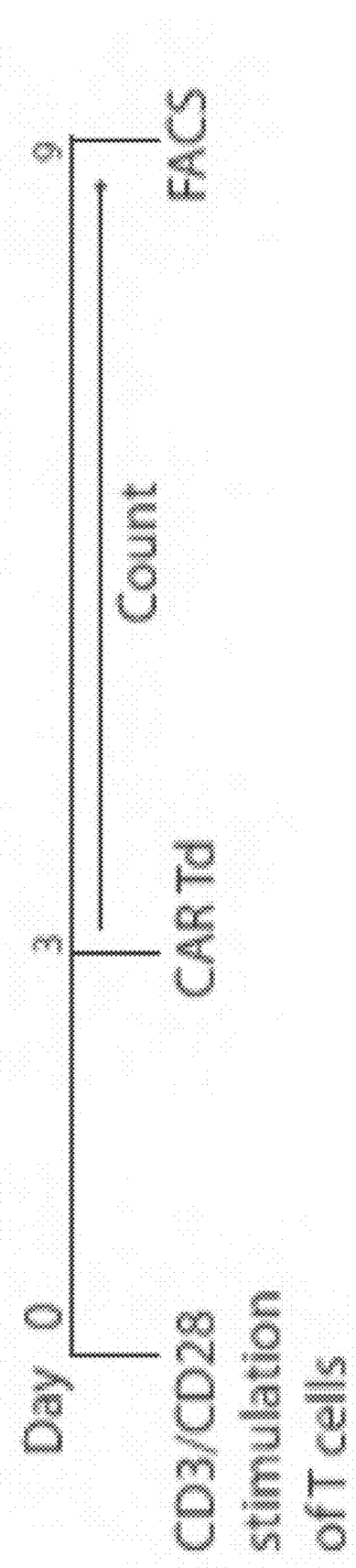
Figures 5C, 5D:
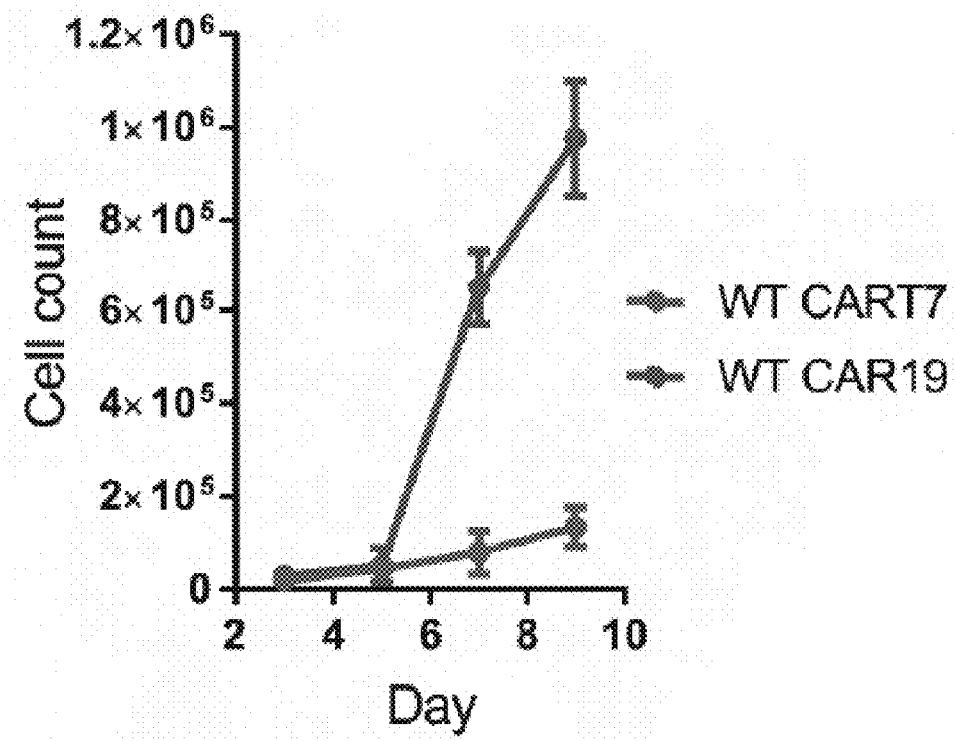

To generate the CD7-CAR-T (CART7), an anti-CD7 single chain variable fragment (scFv) was commercially synthesized and cloned into a 3rd generation CAR backbone with CD28 and 4-1BB internal signaling domains. The extracellular domain of hCD34 was added after a P2A peptide to enable both detection of CAR following viral transduction and purification using anti-hCD34 magnetic beads (FIG. 5A). CAR-T targeting CD19 (CART19) was used as an irrelevant CAR-T control. Following transduction of T cells there were significantly fewer CART7 than CART19 (FIG. 5C). In addition, CART7 were biased towards a CD4 phenotype when compared to CART19 (FIG. 5D).

Example 5: Deletion of CD7 by CRISPR/Cas9

Figure 5E:
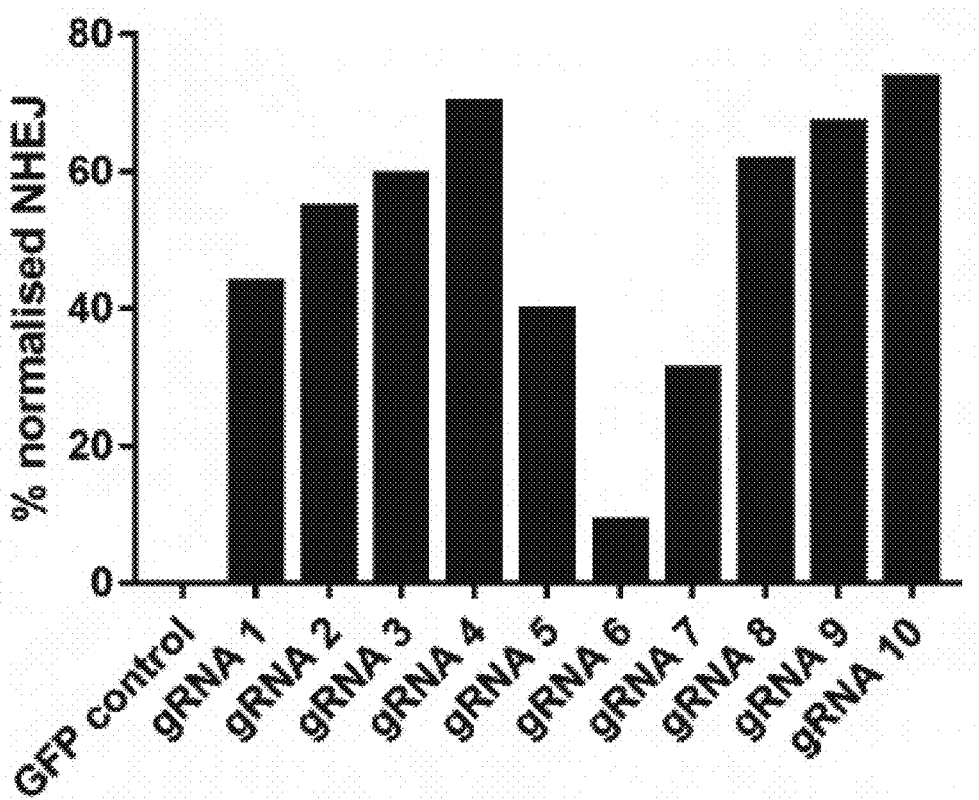
Figure 5F:
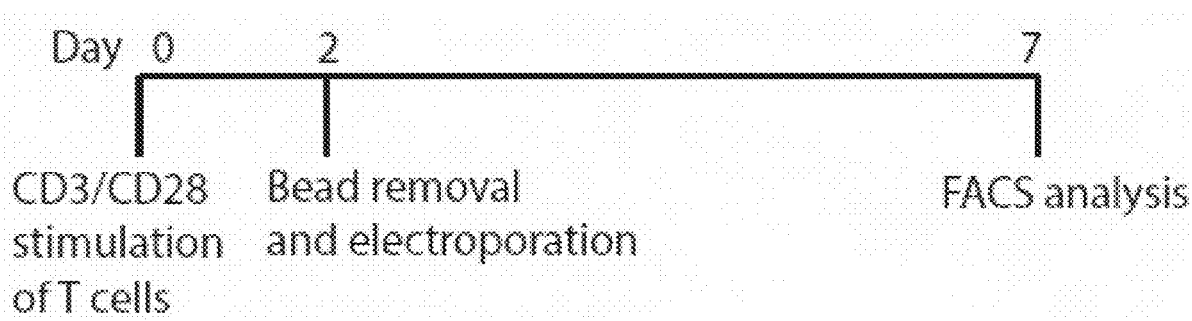
Figure 5G:
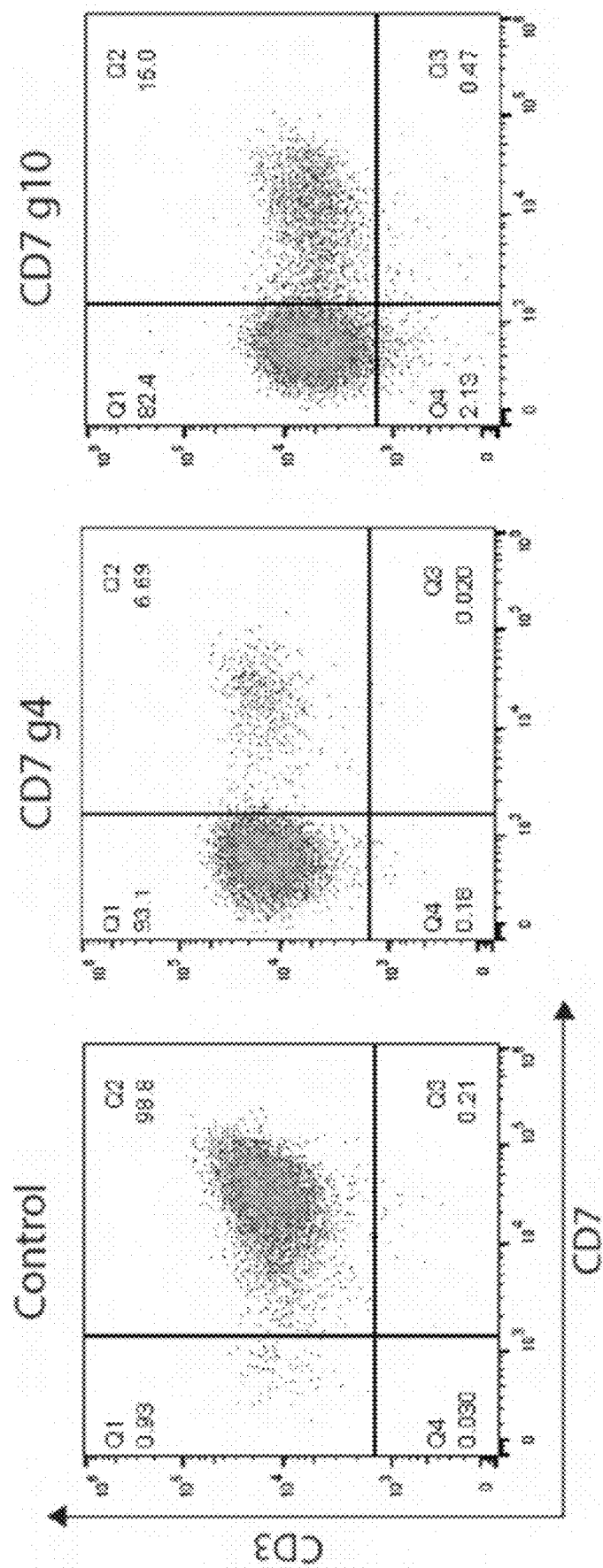
Figure 5H:
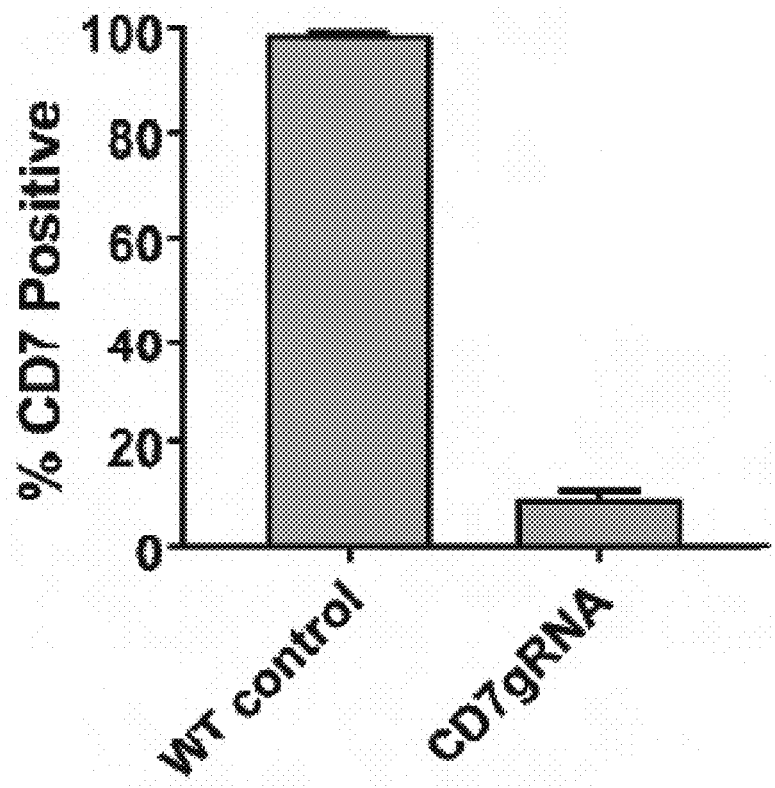
Figure 5I:
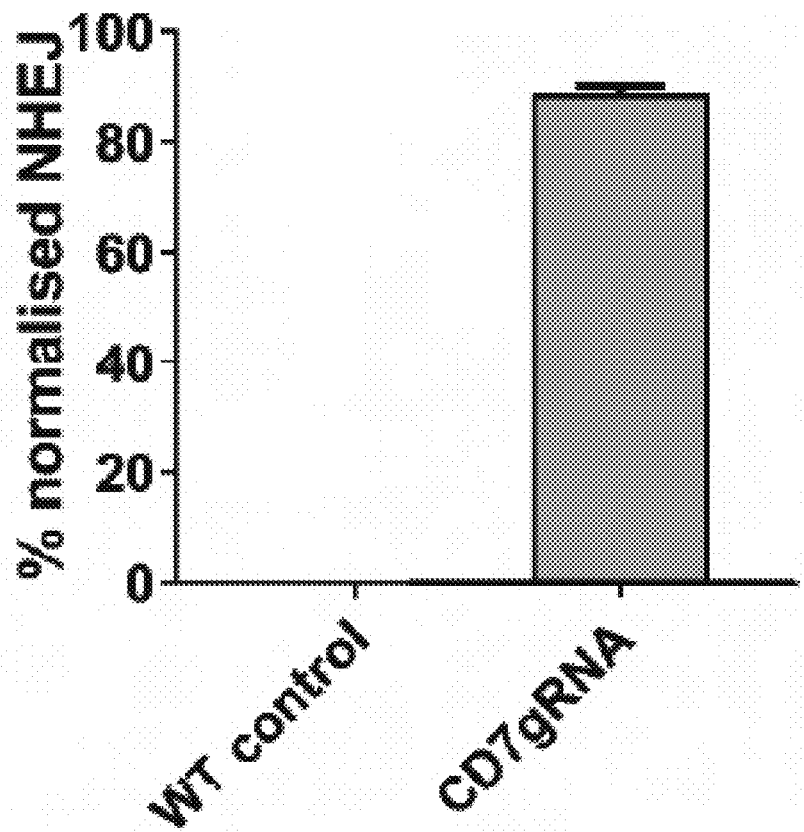
Figure 5J:
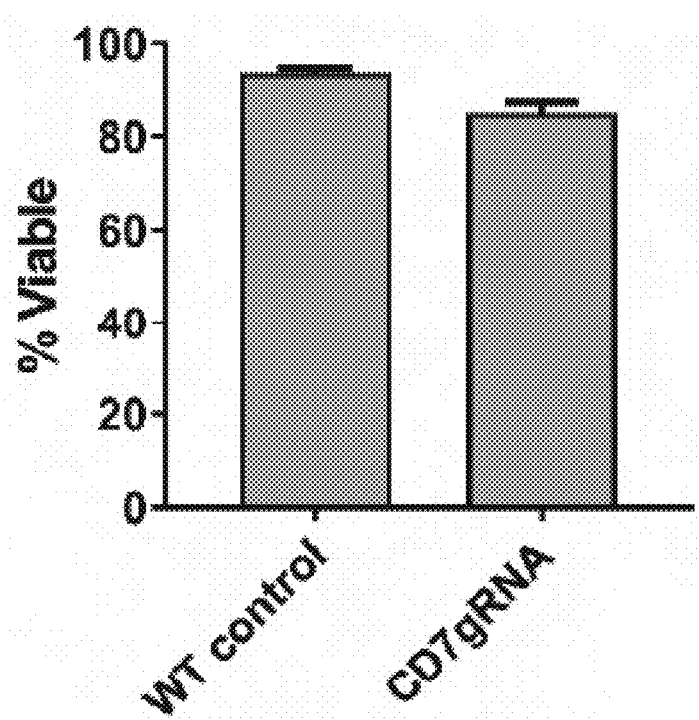

To prevent fratricide, CD7 was deleted in CAR-T using CRISPR/Cas9 gene-editing. Ten guide RNAs (gRNA) targeting CD7 were designed and validated for activity (SEQ ID NOS: 7-16). Plasmids encoding the gRNA and Cas9 were electroporated into the K562 leukemia cell line. CD7g4 and CD7g10 had the highest gene-editing efficiencies, as determined by targeted deep-sequencing across the CD7 locus (FIG. 5E) and were selected for further investigation. CD7g4 and CD7g10 guides were commercially synthesized, incorporating 2'-O-methyl and 3'phosphorothioate bases at the three terminal bases of the 5' and 3' of the gRNA to protect from nucleases activity 15. The efficacy of gene-editing by both CD7g4 and CD7g10 in human primary T cells was tested. Activated T cells were electroporated with gRNA and Cas9 mRNA (FIG. 5F), and then analysis by flow cytometry on day +7. CD7g4 was the most effective at deleting CD7 expression, reducing the percentage of CD7+ T cells from 98.8%±0.17 to 9.1%±1.74 (FIG. 5G-H). Effective disruption of the CD7 locus was confirmed by targeted deep-sequencing with indels observed in 89.14% of CD7 sequence reads (FIG. 5I). Only minimal loss of viability was observed 24 hrs post electroporation (FIG. 5J). As CD7g4 was most effective at deleting expression of CD7 in T cells, all future experiments were performed using CD7g4.

Figure 6A:
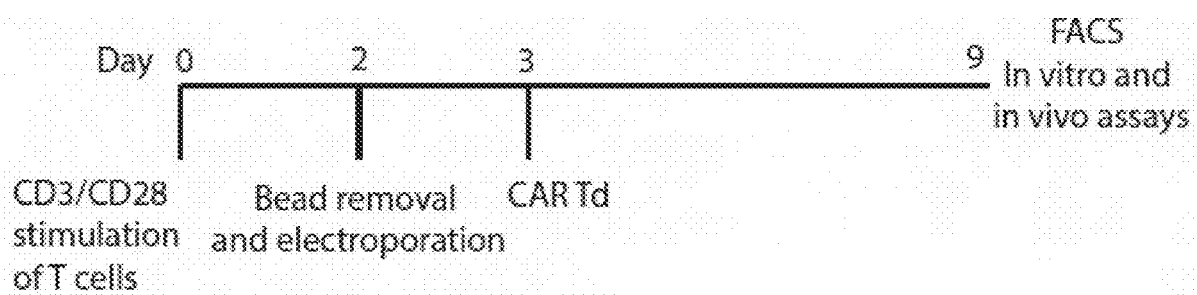
FIG. 6A-FIG. 6G illustrate that CD7ΔCART7 effectively kills T-ALL cell lines in vitro and in vivo.
Figure 6B:
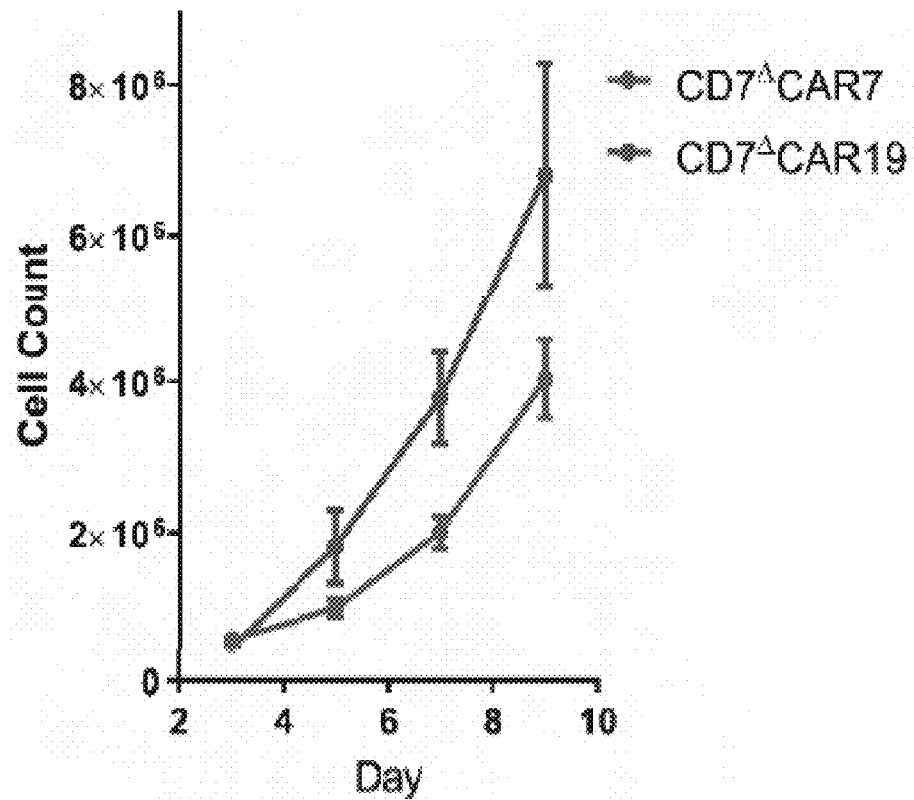
Figure 6C:
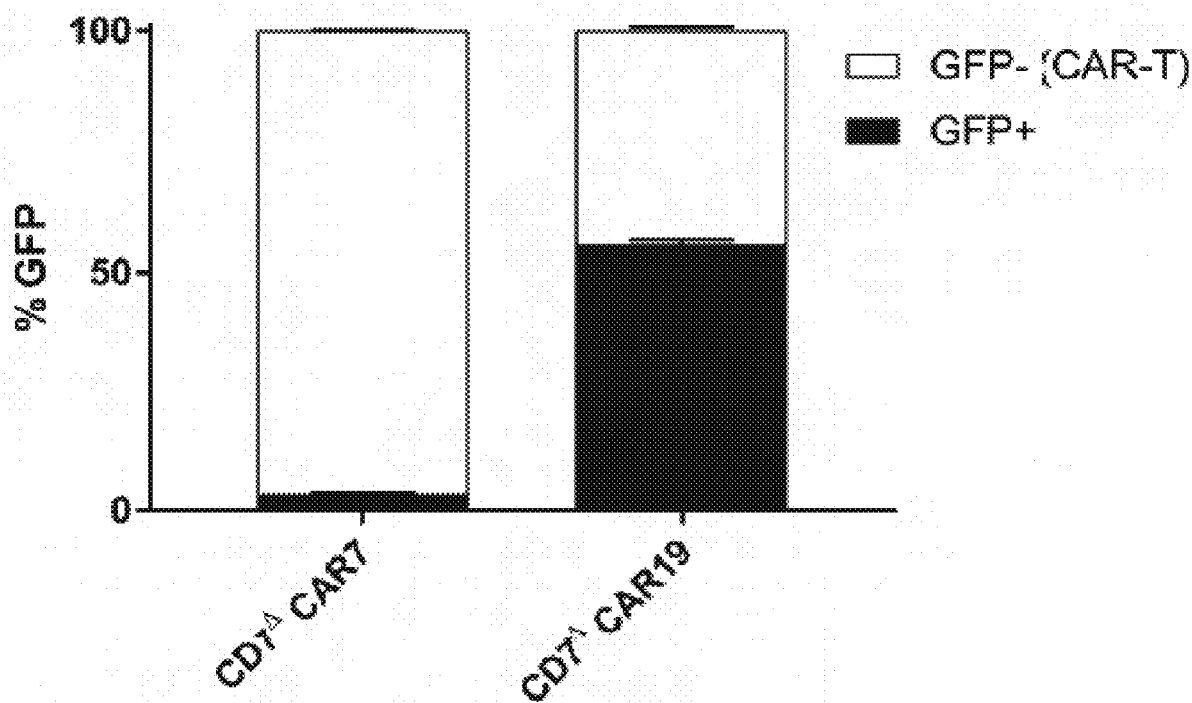
Figure 6D:
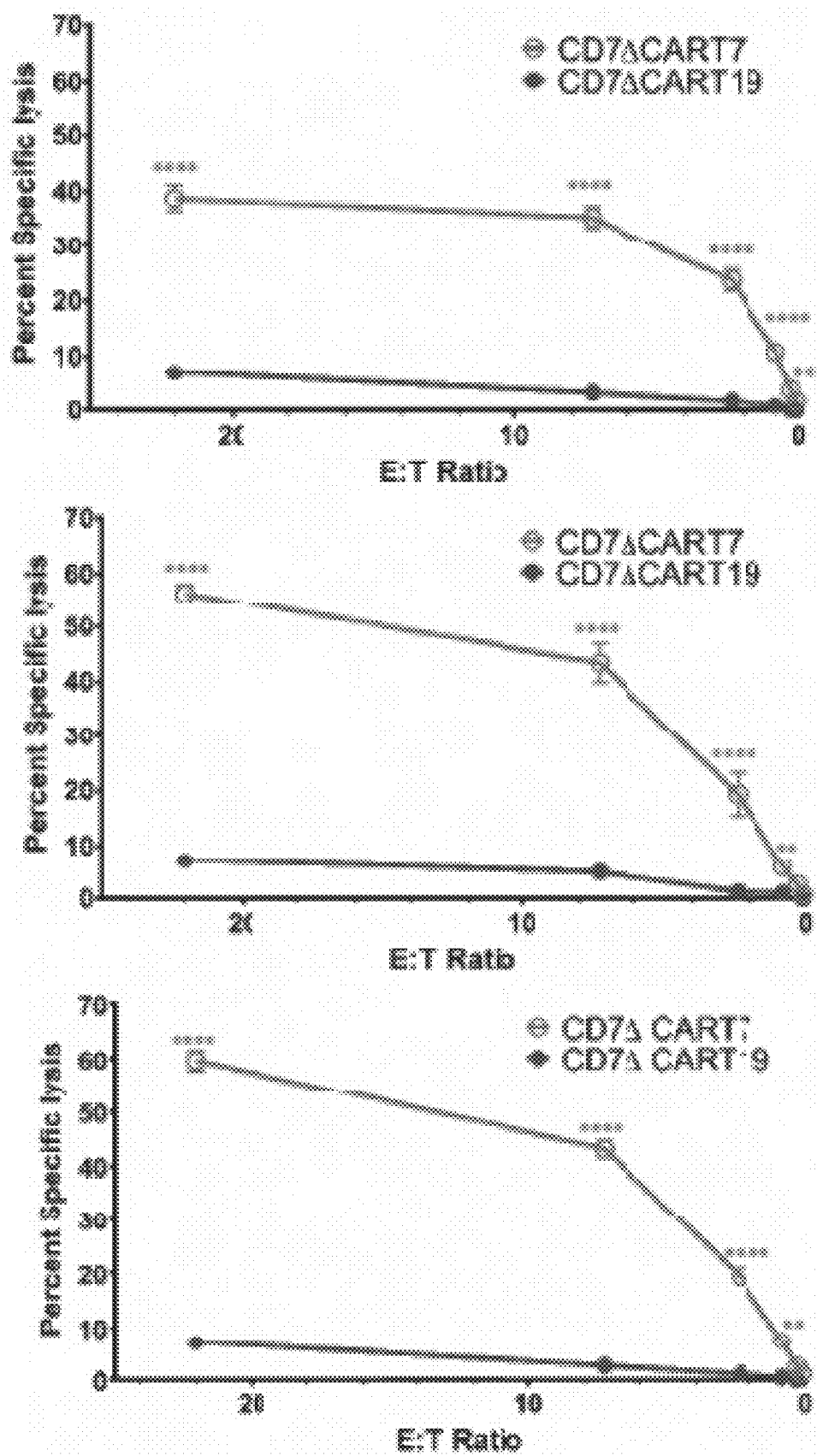
Figure 6E:
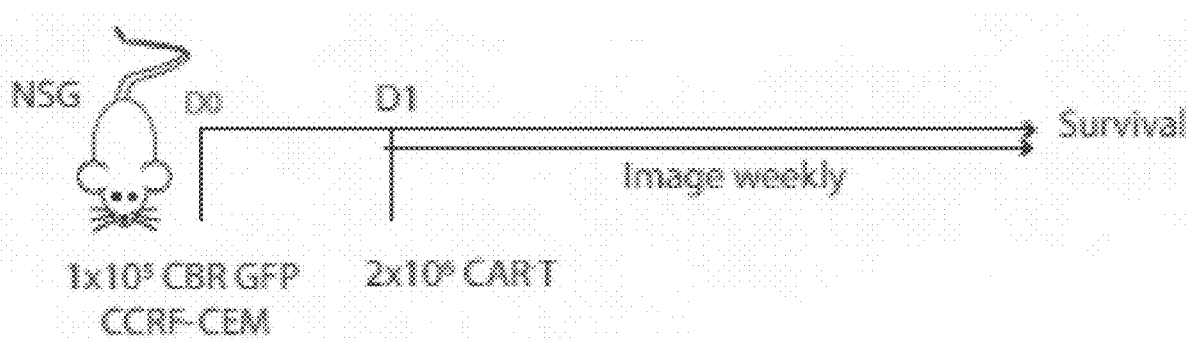
Figure 6F:
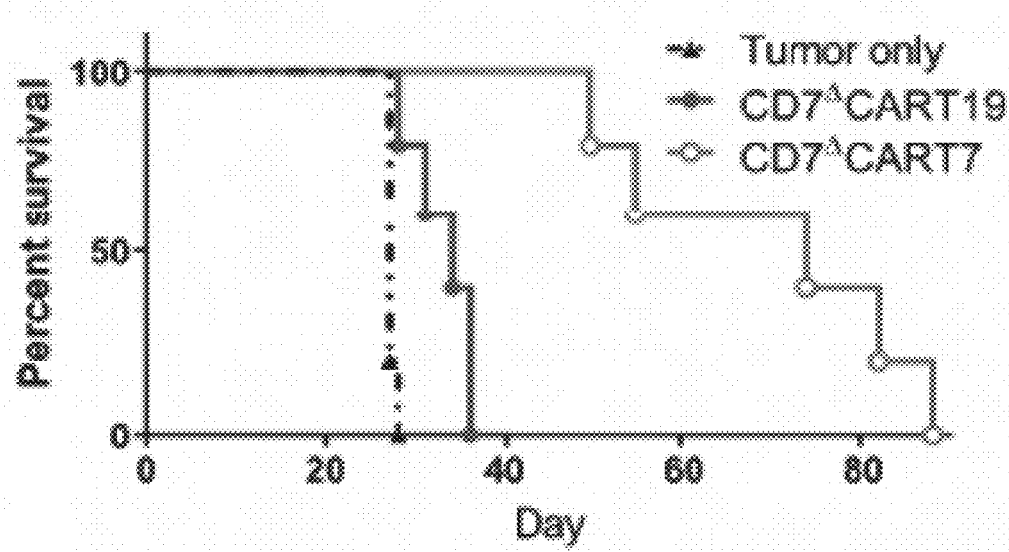
Figure 6G:
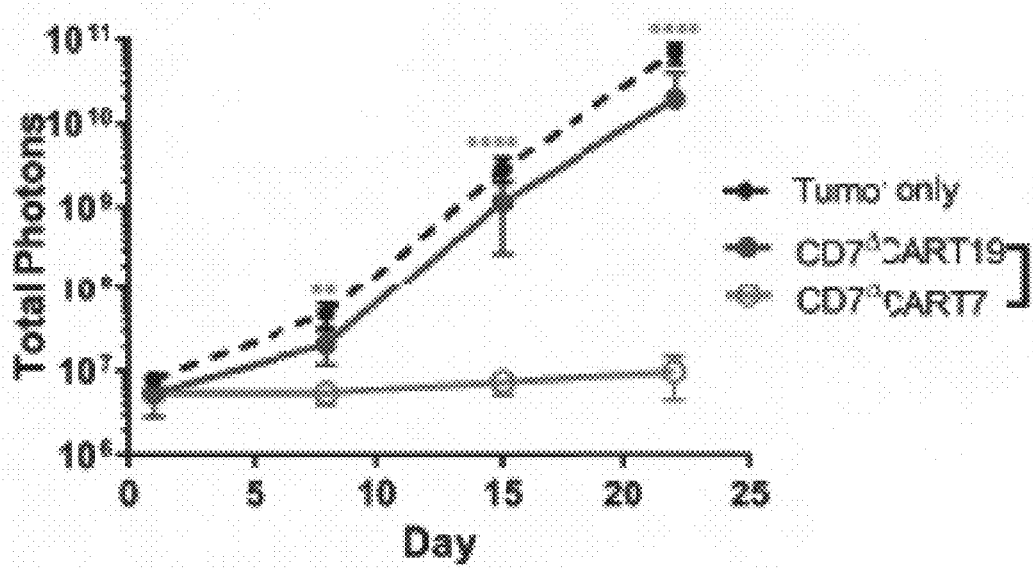

Example 6: CD7ΔCART7 Prevents Fratricide and Effectively Kills T-ALL In Vitro and In Vivo CRISPR/Cas9 gene-editing of CD7 followed by transduction of CD7 edited T cells (CD7Δ) with the CART7 construct was performed as shown in FIG. 5A to generate CD7ΔCART7. Activated T cells were electroporated with spCas9 mRNA (15 µg) and CD7g4 (20 µg) one day prior to viral transduction with either CAR7 or CAR19 control on Day 3. Cells were cultured for an additional 6 days (FIG. 6A). A low level of fratricide resulting from residual CD7 surface expression following gene-editing was anticipated, and this was confirmed by a moderate reduction in CD7ΔCART7 yield relative to CD7ΔCART19 (7.5-fold vs. 12.6-fold expansion over 6 days FIG. 6B). Autologous T cells transduced with GFP were effectively killed by CD7ΔCART7, but not CD7ΔCART19 confirming the requirement for CD7 deletion when CAR-T target CD7 (FIG. 6C). Finally, in contrast to CD7ΔCART19, CD7ΔCART7 effectively killed CD7+ T-ALL cell lines MOLT-4 (70% CD7+), MOLT-3 (96% CD7+) and HSB-2 (99% CD7+) as determined by 4 hr Cr release assays (FIG. 6D). To assess the activity of CD7ΔCART7 in a xenogeneic model of T-ALL, $1 \times 10^5$ Click Beetle Red luciferase (CBR) labeled CCRF-CEM T-ALL (99% CD7+ by FACS) cells were injected I.V. into NSG recipients prior to infusion of 2×10×6 CD7ΔCART7 or non-targeting CD7ΔCART19 control cells on day+1 (FIG. 6E). In contrast to mice receiving CD7ΔCART19, or mice injected with tumor only, mice receiving CD7ΔCART7 had significantly prolonged survival (FIG. 6F) and reduced tumor burden as determined by bioluminescent imaging (BLI) (FIG. 6G). To assess efficacy of CD7ΔCART7 against patient primary T-ALL cells, CAR-T were tested against patient derived xenografts. However, T-ALL blasts were only detectable in mice receiving tumor only and were eliminated in mice receiving either CD7ΔCART7 or CD7ΔCART19 or unmanipulated T cells, suggesting that CD7ΔCART7 maintained similar levels of alloreactivity in vivo in NSG mice as both non-transduced human T cells and CD7ΔCART19.

Figure 7A:
FIG. 7A-FIG. 7G illustrates that UCART7 cells deficient in CD7 and TRAC effectively kills T-ALL cell lines in vitro.
Figure 7B:
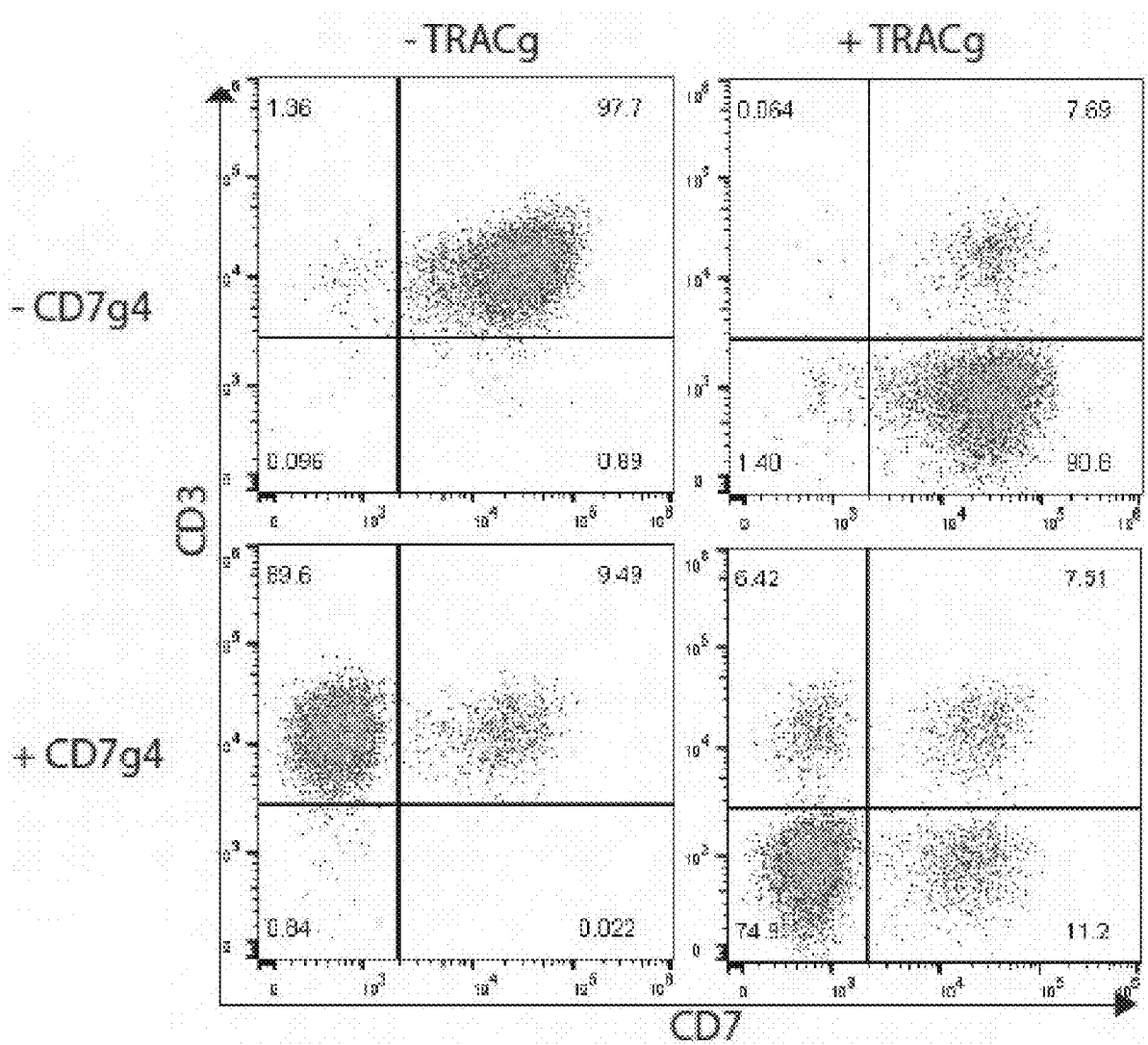
Figure 7C:
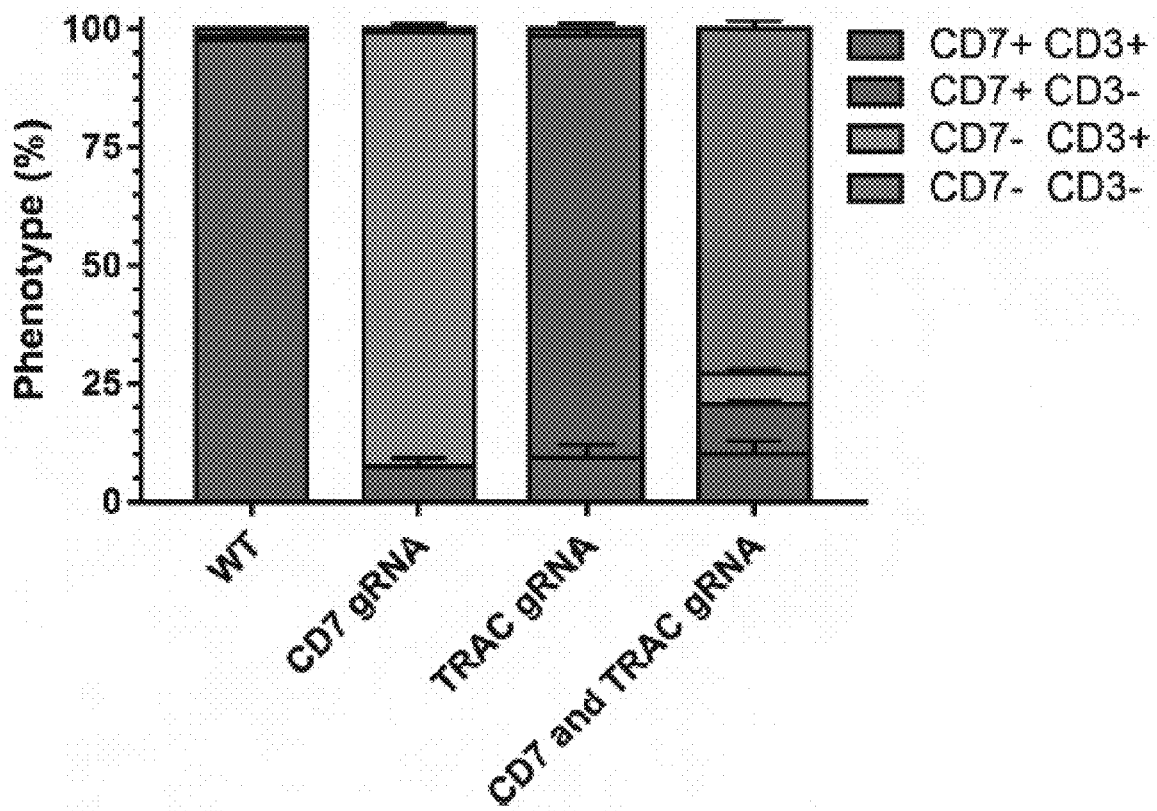
Figure 7D:
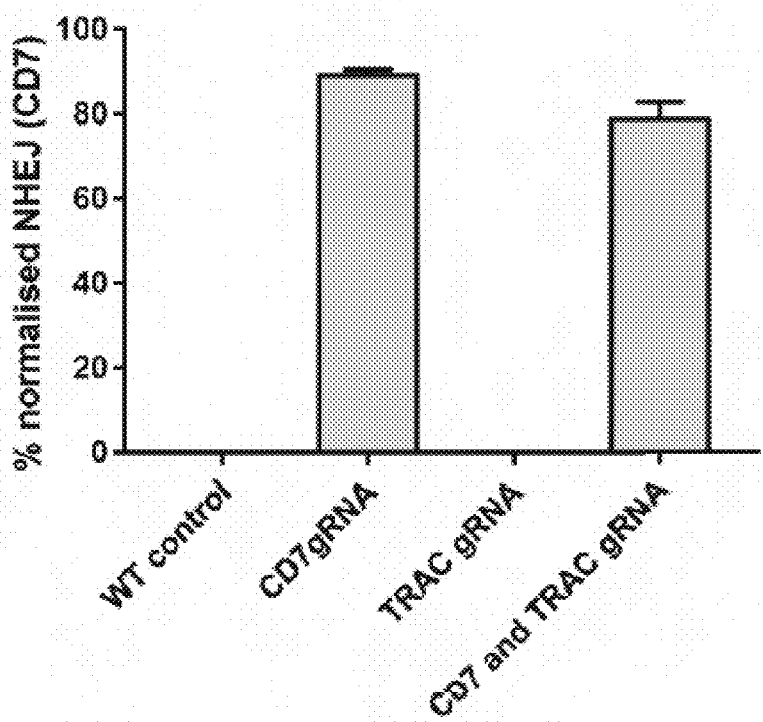
Figure 7E:
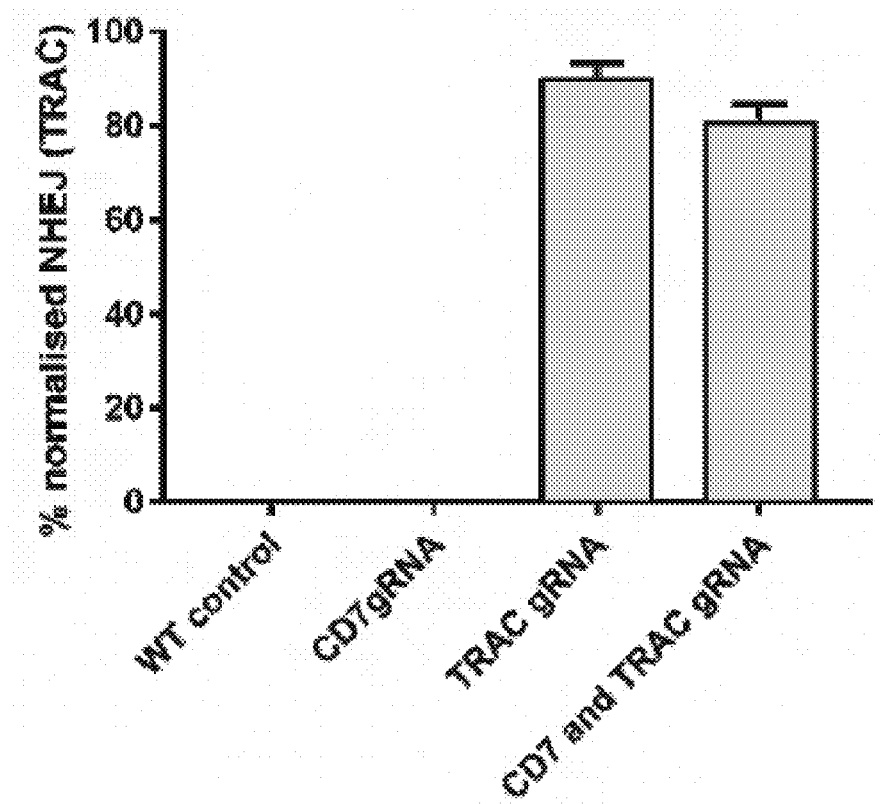

Example 7: Double Deletion of TRAC and CD7 in CART7 Prevents Fratricide, GvHD and Maintains Robust CD7 Directed T-ALL Killing To overcome alloreactive barriers that limit the use of non-self T cells, due to the risk of lethal GvHD, CAR-T in which both CD7 and the T cell receptor alpha chain (TRAC) were genetically deleted were generated. The gRNA sequence, targeting TRAC, was obtained from Osborn et al. T cells were activated using anti-CD3/CD28 beads for two days prior to bead removal and electroporation with 20 μg of CD7g4, 20 μg of TRACg and 15 μg of Cas9 mRNA (FIG. 7A). Multiplex CRISPR/cas9 gene-editing resulted in the simultaneous deletion of CD7 and TRAC in 72.8%±1.92 of cells, as determined by FACS analysis (FIG. 7B-E).

Figure 7F:
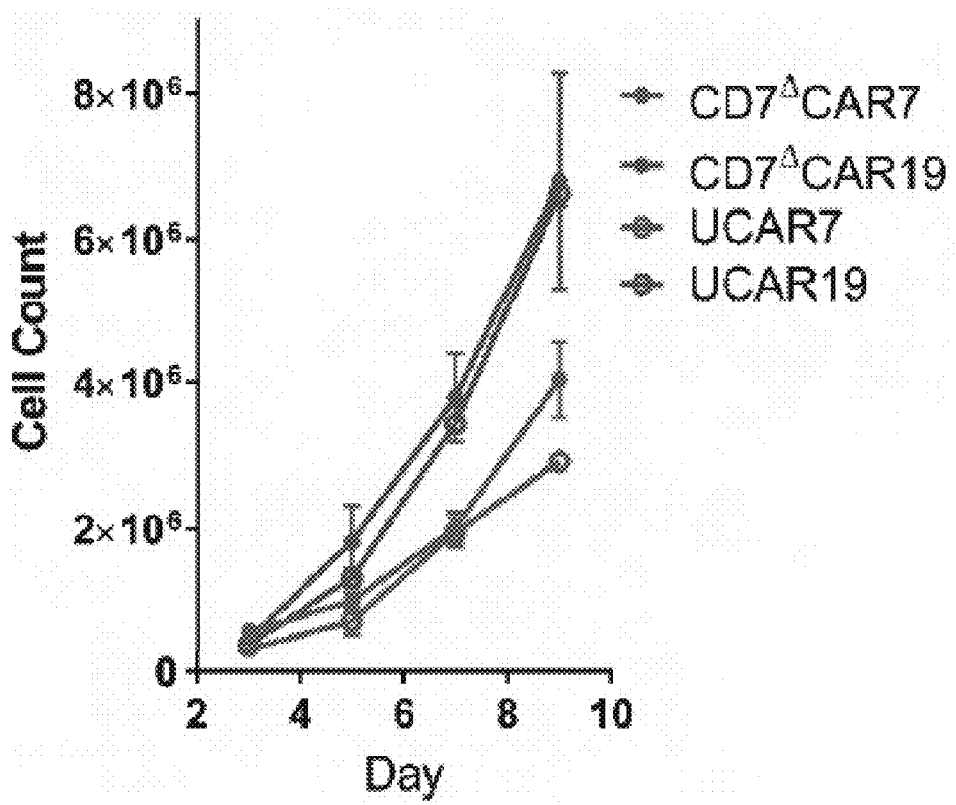
Figure 7G:
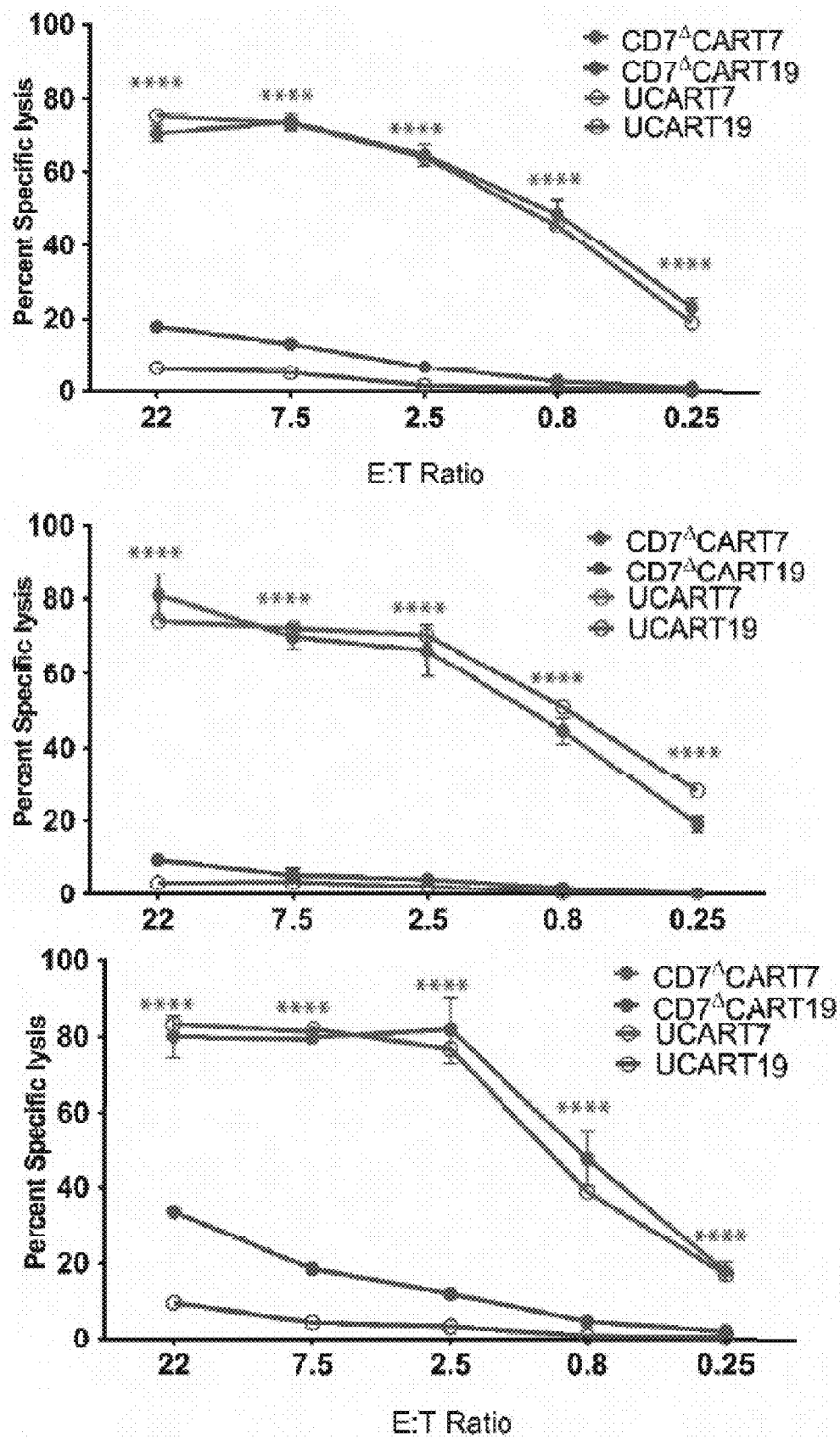

In keeping with recent nomenclature in the field, CD7ΔTRACΔCART7 was termed universal CART7 or UCART717. UCART7 was as effective as CD7ΔCART7 at killing T-ALL cell lines in vitro. UCART7 had no proliferation defect when compared to CD7ΔCART7, however, as observed with CD7ΔCART7, UCART7 resulted in moderately reduced CAR-T proliferation and yield relative to the CD19 control CART (FIG. 7F). Since incomplete gene-editing of TRAC leaves residual potentially alloreactive CD3+ CAR-T, these were depleted by negative selection using anti-CD3 magnetic beads on Day +8. Both UCART7 and CD7ΔCART7 killed CD7+ T-ALL cell lines, MOLT3, CCRF-CEM and HSB-2 in vitro with equally high efficiencies demonstrating no loss of efficacy upon double deletion of CD7 and TRAC (FIG. 7G). Interestingly, non-specific killing by UCART19 was attenuated at high effector to target (E:T) ratios when compared to CD7ΔCART19 suggesting loss of alloreactivity following TRAC deletion.

Figure 8A:
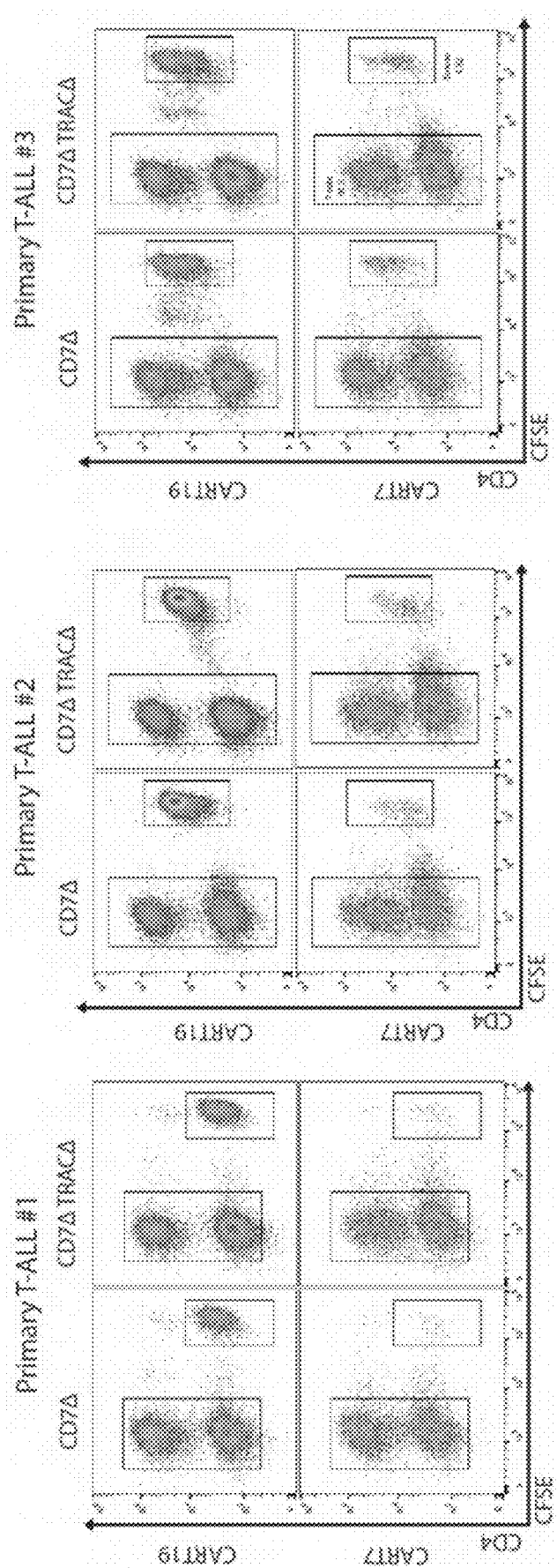
FIG. 8A-FIG. 8B illustrate that UCART7 kills primary patient T-ALL blast in vitro. Primary blasts obtained from three individual patients with CD7+ T-ALL were labeled with 150 nM carboxyfluorescein succinimidyl ester (CFSE). Labeled cells were co-incubated at a 1:1 ratio with either CD7ΔCART7, UCART7, or their respective CD19 controls in triplicate for 24 hours prior to FACS analysis. Accucount florescent beads were used to determine actual cell counts. Data were collected using a Gallios cytometer.
Figure 8B:
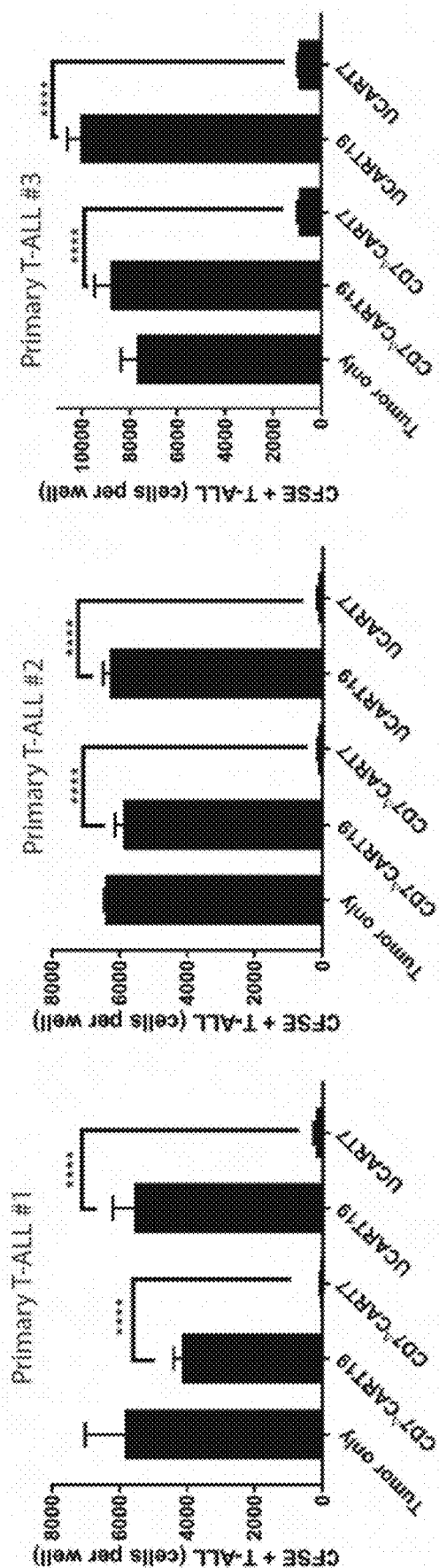

The ability of UCART7 to kill primary T-ALL blasts in vitro was tested next. Due to the similarity of antigen expression between primary T-ALL and CAR-T, primary T-ALL cells were labeled with CFSE to clearly distinguish T-ALL from CAR-T. T-ALL cells were incubated with CAR-T at a ratio of 1:1 for 24 hrs. Both CD7ΔCART7 and UCART7 killed an average of 95% of T-ALL blasts across all three primary samples, relative to the respective CD19 control CAR-T (FIG. 8A), thus demonstrating exceptional efficacy against human primary T-ALL in vitro.

Figure 9A:
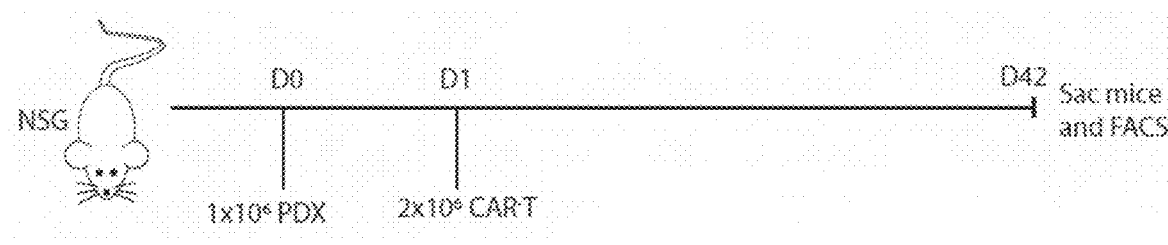
FIG. 9A-FIG. 9F illustrate that UCART7 kills primary patient T-ALL blast in vivo without inducing xenogenic GvHD.
Figure 9B:
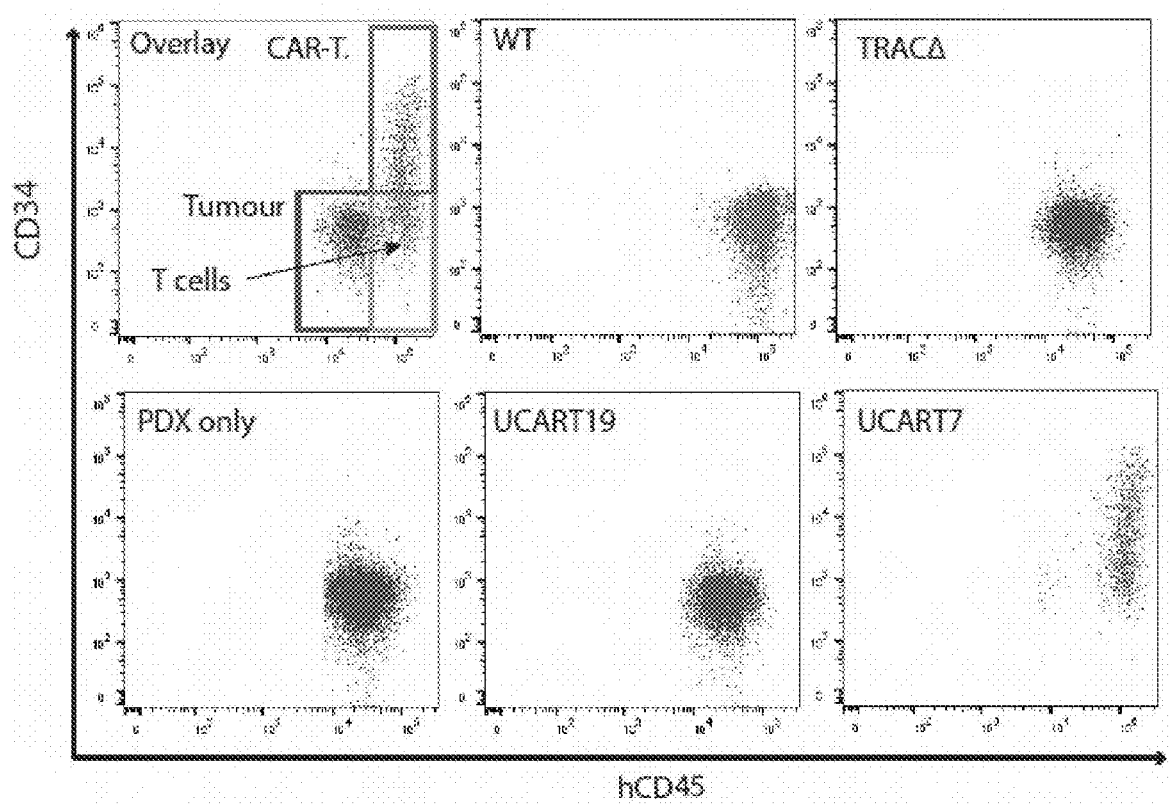
Figure 9C:
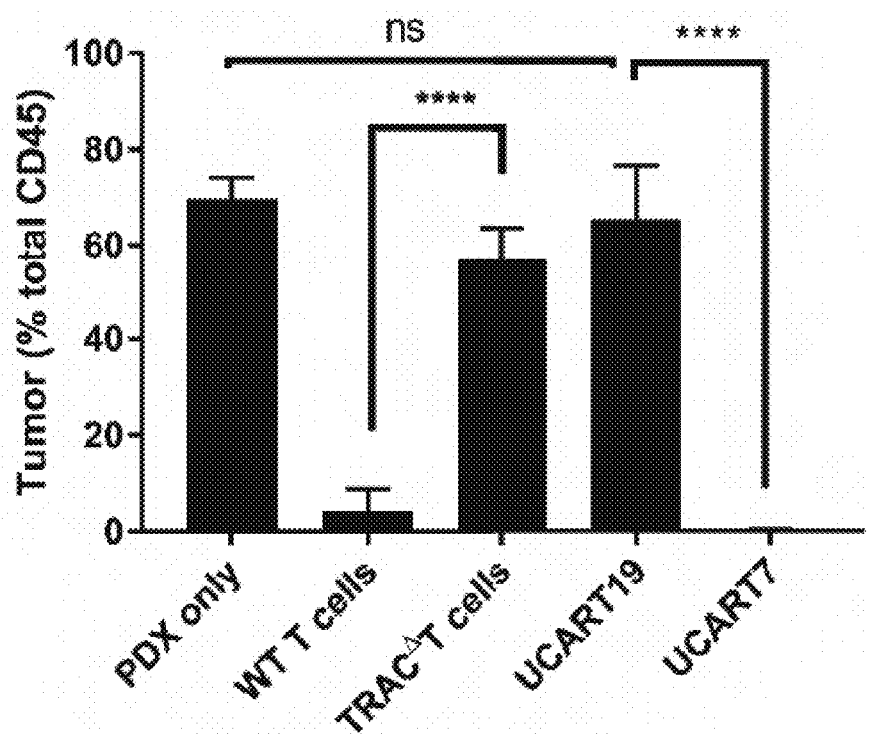
Figure 9D:
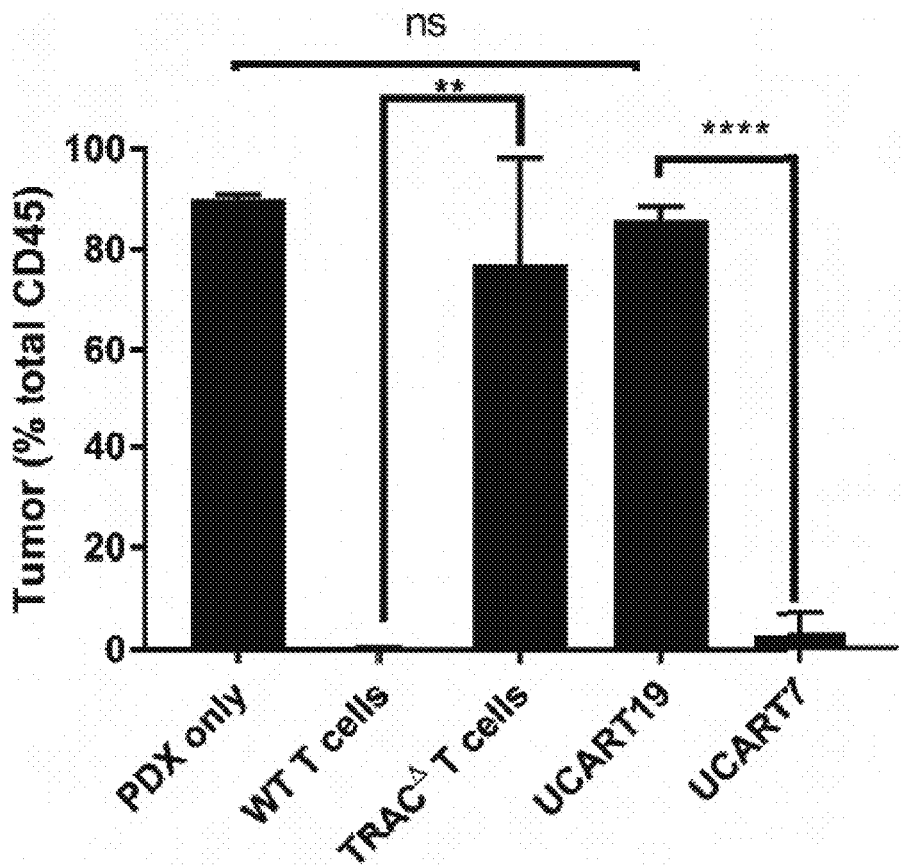
Figure 9E:
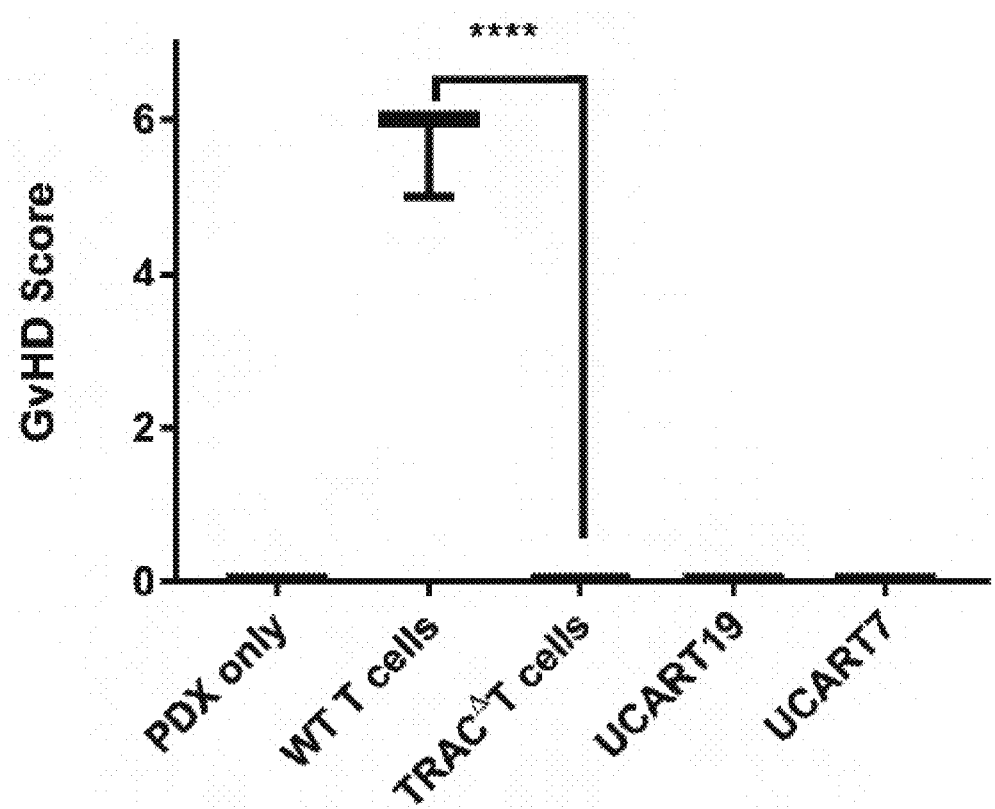
Figure 9F:
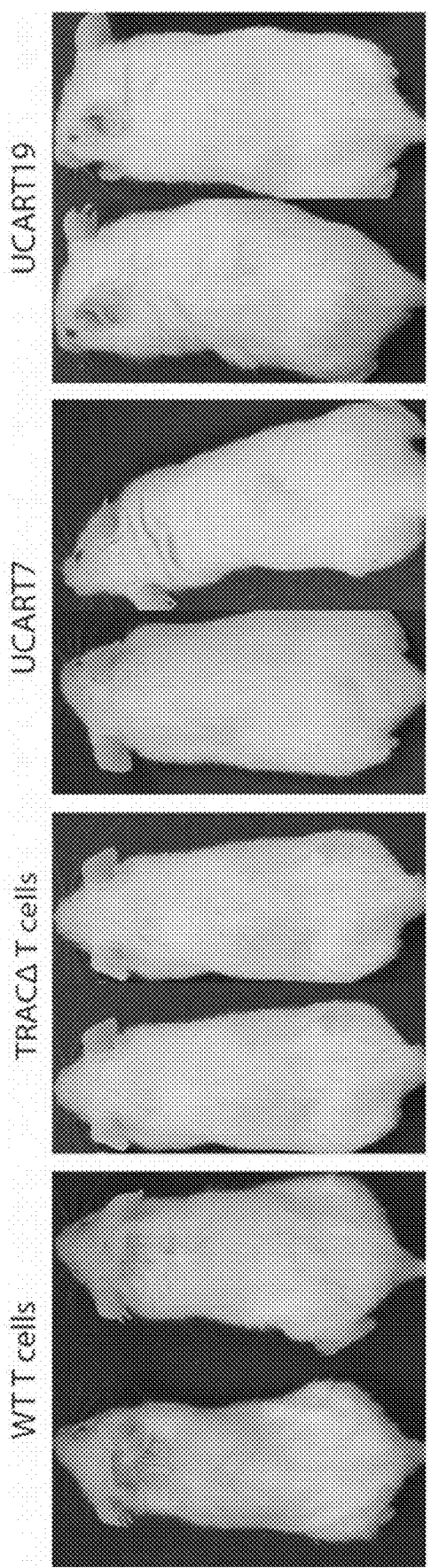

In light of the anti-tumor activity when either WT T cells, CD7ΔCART and CD7ΔCART19 were infused into primary T-ALL PDX bearing NSG mice, the capacity of UCART7 to kill primary T-ALL in vivo without alloreactive Graft-vs.-Leukemia effect (GvL) or xenogeneic GvHD was tested (FIG. 9A). Recipients of T cells edited to delete TRAC (TRACΔ) exhibited high tumor burden in both the blood (FIG. 9B-C) and spleen (FIG. 9D) when compared to recipients of WT T cells (Day +48 spleen p<0.0001, blood p=0.0001). Furthermore, considerable expansion of alloreactive T cells (FIG. 9B) and severe GvHD (mean clinical GvHD score=5.66, p<0.0001 FIG. 9E) was observed in recipients of WT T cells. In contrast, GvHD was completely absent and T cells undetectable in mice receiving TRACΔ T cells (p<0.0001, FIG. 9E,F). T-ALL blasts were absent in peripheral blood of mice receiving UCART7 in comparison to mice receiving UCART19 with T-ALL comprising >56% of total CD45+ cells in these mice (p<0.0001), similar to the high tumor burden observed in PDX only controls (FIG. 9C). Concordant results were observed in the spleen (FIG. 9D, UCART7 <3% T-ALL vs. UCART19=85.87% T-ALL; p<0.0001), with TRACΔ T cells, UCAR19 and PDX only recipient mice exhibiting splenomegaly. In stark contrast UCART7 recipients had normal sized spleens. Furthermore, unlike UCART19, UCART7 were detectable 6 weeks' post injection as detected by the hCD34 epitope (FIG. 9B), demonstrating persistence of UCART7 in vivo.

Example 8: Off Target Nuclease Activity

High efficiency gene-editing with CRISPR/Cas9 can induce undesirable off-target genetic changes that could have potentially detrimental effects on the biology of these T cells and subsequently on the recipients that receive UCART7 infusions. Two different techniques to assess off-target genetic changes in human primary T cells were used, both of which rely on the insertion of a small double stranded oligodeoxynucleotide (dsODN) at DNA double strand breaks. The first protocol utilized a modified version of GUIDE-seq, without the inclusion of barcoded indexes, to specifically amplify target sites surrounding the inserted dsODN using PCR; the second technique used Integrated DNA Technologies (IDT) capture probes to enrich loci containing the target dsODN sequence. Both techniques use next-generation sequencing to identify the loci of inserted dsODN. To ensure identification of bona fide sites of off-target nuclease activity, each condition (CD7g4, TRACg and combined CD7g+TRACg) was performed in triplicate, generating an average $1.26 \times 10^6$ (mean) sequencing reads per replicate. Loci with bidirectional sequencing reads >10× coverage were included in the analysis. First, the ability of each technique to identify on-target sites was assessed. Both GUIDE-seq and dsODN capture robustly identified sites of on-target activity, with each on-target site generating between 300× and 22,000× coverage across all three replicates in each condition (Table 2 and 3). Next, off target nuclease activity using the same stringency was assessed. GUIDE-seq revealed a single off target site in multiplex edited T cells (CD7g4+TRACg), an intronic insertion in RBM33, present in all three replicates. No off-target sites were observed when assessed by dsODN capture despite high coverage of on-target activity (Table 2). Upon relaxing the stringency of GUIDE-seq analysis to include potential off target sites present in two or more replicates, we identified an additional four potential off-target sites for CD7, four sites for TRAC, and one additional site of potential off-target activity for multiplexed CD7 and TRAC gene-editing (Table 2). Loci identified by GUIDE-seq were not present in the data obtained using dsODN capture, nor were additional sites of off-target nuclease activity identified following analysis of these data with reduced stringency. These results suggest that high efficiency CRISPR/Cas9 gene-editing of primary T cells with CD7g4 and TRAC gRNA, individually or in combination, is not associated with significant off-target activity using these platforms.

TABLE 2

Sites of nuclease activity identified using GUIDE-seq. On target activity is highlighted in dark grey.

| position | Gene | CD7g4 | | TRACg | | CD7g + TRACg | | |
|---|---|---|---|---|---|---|---|---|
| | | total reads (mean) | # of replicates | total reads (mean) | # of replicates | total reads (mean) | # of replicates | |
| Chr17: 80274575 | CD7 | 501 | 3 | — | — | 326 | 3 | On target |
| Chr14: 23016519 | TRAC | — | — | 2845 | 3 | 1171 | 3 | On target |
| Chr7: 155492215 | RMB33 (Intron) | — | — | — | — | 739 | 3 | Off-target |

TABLE 2-continued

Sites of nuclease activity identified using GUIDE-seq. On target activity is highlighted in dark grey.

| | | CD7g4 | | TRACg | | CD7g + TRACg | | |
|---|---|---|---|---|---|---|---|---|
| position | Gene | total reads (mean) | # of replicates | total reads (mean) | # of replicates | total reads (mean) | # of replicates | |
| Chr18: 57136752 | CCBE1 (Exon) | 15 | 2 | — | — | — | — | Off-target |
| Chr5: 1246388037 | Intergenic | 78 | 2 | — | — | — | — | Off-target |
| Chr2: 131741952 | ARHGEF41 (Intron) | 188.5 | 2 | — | — | — | — | Off-target |
| Chr6: 163217520 | PACRG | 292 | 2 | — | — | — | — | Off-target |
| Chr4: 49659204 | Intergenic | — | — | 278 | 2 | — | — | Off-target |
| Chr5: 100549427 | Intergenic | — | — | 127 | 2 | — | — | Off-target |
| Chr4: 102319592 | Intergenic | — | — | 112.5 | 2 | — | — | Off-target |
| Chr5: 163357022 | Intergenic | — | — | 53.5 | 2 | — | — | Off-target |
| Chr2: 177340112 | Intergenic | — | — | — | — | 51.5 | 2 | Off-target |

TABLE 3

Sites of nuclease activity identified using dsODN probe capture. On target activity is highlighted in dark grey.

| | | CD7g4 | | TRACg | | CD7g + TRACg | | |
|---|---|---|---|---|---|---|---|---|
| position | Gene | total reads (mean) | # of replicates | total reads (mean) | # of replicates | total reads (mean) | # of replicates | |
| Chr17: 80274575 | CD7 | 2268 | 3 | — | — | 2163 | 3 | On target |
| Chr14: 23016519 | TRAC | — | — | 23632 | 3 | 22810 | 3 | On target |

Discussion for Examples 4-8

In this report the generation of CRISPR/cas9 genetically edited human T cells lacking both CD7 and TRAC was demonstrated. Lentiviral transduction of these genetically edited T cells with a CD7-CAR (UCART7) allows for efficient killing of CD7+ primary human T-ALL and T-ALL cell lines in vitro and in vivo without consequent fratricide or T cell mediated xenogeneic GvHD. This work improves upon previous CAR-T targeting T cell malignancies which induce partial fratricide. Pinz et al. described the preclinical development of a CD4-targeted CAR-T which mediated CD8+ CAR-T-mediated cytotoxicity of CD4+ targets resulting in complete CD4+ T cell loss. Likewise, Mamonkin et al described a CD5-targeted CAR-T that induces only transient fratricide, allowing sufficient CD5 CAR-T expansion despite almost universal expression of CD5 on activated WT T cells.

CD7 was chosen as a target due to high expression in the majority of NHL and T-ALL. In addition to T cell malignancies, CD7 is expressed in ~24% of AML and is thought to be marker of leukemic stem cells, thus CART7 could be used to treat myeloid as well as lymphoid malignancies. Furthermore, an antigen which could be deleted in T cells without impacting immune function needed to be targeted. Mice with genetic deletion of CD7 are phenotypically normal (with normal lifespan) with normal lymphocyte populations and maintain T cell activity in response to allogeneic and mitogenic stimuli. Thus, CD7 is the ideal candidate for gene-editing of CAR-T to target both AML and T cell malignancies.

There was extensive fratricide when CART7 was used without CD7 deletion with surviving CART7 predominantly CD4+ and CD7-24. These data underline the importance of using CART7 which are themselves devoid of CD7. Such cells provide optimal resistance to fratricide while allowing expansion of cytotoxic CD8 T cells with balanced expansion of CD4 cells. Indeed, high efficiency CRISPR/cas9-mediated CD7 genetic deletion mitigated CAR7 fratricide, and upon CD7 protein loss (which may lag genetic deletion), the cells demonstrated complete fratricide resistance.

The use of autologous T cell for the generation of CART7 presents unique challenges. First, patients with relapsed T-ALL and T-NHL are often heavily pretreated with T cell poisons such as purine nucleoside analogues (fludarabine, cladribine, nelarabine) and T cell cytotoxic monoclonal antibodies (Campath). Therefore, the number and function of T cells may be markedly reduced thereby limiting the efficient generation, sufficient numbers, and function of CART7 for therapeutic benefit. Second, most T-cell hematologic malignancies and normal T effectors co-express many of the same surface antigens making it very difficult to purify normal T effectors away from the malignant T cells for genetic editing and lentiviral transduction. If the process of purification is not absolute then there will be a risk of deleting CD7 in the malignant T cells thus generating a population of contaminating T cell cancers that are potentially resistant to UCART7. Thus, the potential contamination risk of normal effector T cells with malignant T cell precludes the use of patient-derived T cells to generate CAR-T cells for T cell malignancies. Consequently, CD7ΔCART7 were further modified by editing out TRAC permitting the use of allogeneic donor T cells without the risk of inducing GVHD. Following the success of the first in human trial of UCART19, a TRAC edited non-alloreactive CAR-T to CD19 generated from allogeneic donor T cells, we developed UCART7 in which we have successfully deleted, with high efficiency and with minimal off target effects, both CD7 and TRAC by multiplex CRISPR/Cas9 gene-editing. UCART7 killed T-ALL cell lines and primary patient T-ALL in vitro as effectively as CD7ΔCART7. Unlike CD7ΔCART7, which demonstrated alloreactive antileukemia activity against T-ALL PDX in vivo, UCART7 demonstrated robust CAR7-mediated killing independent of alloreactivity without inducing GvHD. This suggests TRAC deletion does not alter CAR-mediated cytotoxicity yet completely preventing GvHD.

In addition to T cells, NK cells also express CD7. UCART7-mediated T cell and NK cell killing may potentially prevent or limit allogeneic UCART7 rejection and increase UCART7 persistence. Despite observing UCART7 persistence in our immune-deficient PDX T models, clinical studies will be required to fully characterize UCART7 persistence in humans treated for T cell neoplasms.

Although a robust off-target nuclease activity was not observed following CD7, TRAC, or multiplex gene-editing, the recent development of high-fidelity Cas9 (SpCAS9-HF1) may further reduce the risk of undesirable genetic events. Furthermore, insertion of the CAR directly into the TRAC locus, as recently reported, or, potentially, the CD7 locus, would further mitigate the risk of oncogenic transformation from random viral vector integration into undesirable loci. Furthermore, the vector allows the inclusion of suicide genes such as CD34-TK which was previously shown in a first-in-man study to allow both the effective tracking of genetically modified T cells using [18F] FHBG PET-CT imaging and the elimination of T cells in vivo. This strategy would safeguard against potential toxicity or oncogenic transformation resulting from CRISPR/Cas9 gene-editing and viral integration.

This study presents the first clinically feasible adoptive T cell gene therapy for T cell malignancies. Specifically, it is shown that CD7xTRAC multiplex gene-editing of human T cells followed by lentiviral transduction with a third generation CD7-CAR results in UCART7 that are completely resistant to fratricide and exhibit no alloreactivity or GvHD potential in vivo. This will allow for the use of "off-the-shelf" tumor-free allogeneic T cells as a source of CAR-T. The use of these genetically modified T cells in NSG mice carrying human T-ALL cell lines or primary human T-ALL PDX tumors results in rapid and effective elimination of these tumors in vivo with no signs of xenogeneic GvHD. These findings warrant further efforts to translate these observations into the clinic specifically for the treatment of children and adults with relapsed and refractory T cell hematologic malignancies.

TABLE A

Sequences

| SEQ ID NO | Name | Sequence | Source |
|---|---|---|---|
| 1 | CD7 Locus Forward Primer | GCCTGCGTGGGATCTACCTGAGGCA | Synthesized |
| 2 | CD7 Locus Reverse Primer | AGCTATCTAGGAGGCTGCTGGGGGC | Synthesized |
| 3 | TRAC Locus Forward Primer | TGGGGCAAAGAGGGAAATGA | Synthesized |
| 4 | TRAC Locus Reverse Primer | GTCAGATTTGTTGCTCCAGGC | Synthesized |
| 5 | Rev_5Phos | A*T*ACCGTTATTAACATATGACAACTCAATTAA*A*C | Synthesized |
| 6 | For_/5Phos | G*T*TTAATTGAGTTGTCATATGTTAATAACGGT*A*T | Synthesized |
| 7 | CD7 gRNA 1 | GATGCTCGGACGCCCCACCANGG | Synthesized |
| 8 | CD7 gRNA 2 | ATGCTCGGACGCCCCACCAAGG | Synthesized |
| 9 | CD7 gRNA 3 | AGGCTGTCTGCGGGTCAGGGNGG | Synthesized |
| 10 | CD7 gRNA 4 | ATCACGGAGGTCAATGTCTANGG | Synthesized |
| 11 | CD7 gRNA 5 | TCAGGGAGGGCGGAGCCTGTNGG | Synthesized |
| 12 | CD7 gRNA 6 | GACCTCCGTGATGGCCTGGCNGG | Synthesized |
| 13 | CD7 gRNA 7 | CGTGATGGCCTGGCAGGTGTNGG | Synthesized |
| 14 | CD7 gRNA 8 | GAGGTCAATGTCTACGGCTCNGG | Synthesized |
| 15 | CD7 gRNA 9 | TGTCTACGGCTCCGGCACCCNGG | Synthesized |
| 16 | CD7 gRNA 10 | GTAGACATTGACCTCCGTGANGG | Synthesized |
| 17 | CD7g10 | 5'_2'OMe(G(ps)U(ps)A(ps))GACAUUGACCUCC GUGAGUUUUAGAGCUAGAAAUAGCAAGUUAAAAUAAGG CUAGUCCGUUAUCAACUUGAAAAAGUGGCACCGAGUCG GUGC2'OMe(U(ps)U(ps)U(ps)U_3' | Synthesized |
| 18 | CD7g4 | 5'_2'OMe(A(ps)U(ps)C(ps))ACGGAGGUCAAUG UCUAGUUUUAGAGCUAGAAAUAGCAAGUUAAAAUAAGG CUAGUCCGUUAUCAACUUGAAAAAGUGGCACCGAGUCG GUGC2'OMe(U(ps)U(ps)U(ps)U_3' | Synthesized |

TABLE A-continued

Sequences

| SEQ ID NO | Name | Sequence | Source |
|---|---|---|---|
| 19 | TRACg | 5'_2'OMe(G(ps)A(ps)G(ps))AAUCAAAAUCGGU GAAUGUUUUAGAGCUAGAAAUAGCAAGUUAAAAUAAGG CUAGUCCGUUAUCAACUUGAAAAAGUGGCACCGAGUCG GUGC2'OMe(U(ps)U(ps)U(ps)U 3' | Synthesized |
|  | Dual indexed KAPA library primer sequences MGI(+)_840 Index Seq | TAATCGCG | Synthesized |
|  | MGI(+)_840 Rev comp | CGCGATTA | Synthesized |
| 20 | MGI(+)_840 Primer Sequence (5'-3')*C | CAAGCAGAAGACGGCATACGAGATCGCGATTAGTGACT GGAGTTCAGACGTGTGCTCTTCCGATCTATACCGTTAT TAACATATGACAACTCAATTAAA*C | Synthesized |
|  | MGI(+)_841 Index Seq | TACAGCAC | Synthesized |
|  | MGI(+)_841 Rev comp | GTGCTGTA | Synthesized |
| 21 | MGI(+)_841 Primer Sequence (5'-3')*C | CAAGCAGAAGACGGCATACGAGATGTGCTGTAGTGACT GGAGTTCAGACGTGTGCTCTTCCGATCTATACCGTTAT TAACATATGACAACTCAATTAAA*C | Synthesized |
|  | MGI(+)_843 Index Seq | TCATTCAT | Synthesized |
|  | MGI(+)_843 Rev comp | ATGAATGA | Synthesized |
| 22 | MGI(+)_843 Primer Sequence (5'-3')*C | CAAGCAGAAGACGGCATACGAGATATGAATGAGTGACT GGAGTTCAGACGTGTGCTCTTCCGATCTATACCGTTAT TAACATATGACAACTCAATTAAA*C | Synthesized |
|  | MGI(+)_845 Index Seq | TCTACCGT | Synthesized |
|  | MGI(+)_845 Rev comp | ACGGTAGA | Synthesized |
| 23 | MGI(+)_845 Primer Sequence (5'-3')*C | CAAGCAGAAGACGGCATACGAGATACGGTAGAGTGACT GGAGTTCAGACGTGTGCTCTTCCGATCTATACCGTTAT TAACATATGACAACTCAATTAAA*C | Synthesized |
|  | MGI(+)_846 Index Seq | TGAATGCA | Synthesized |
|  | MGI(+)_846 Rev comp | TGCATTCA | Synthesized |
| 24 | MGI(+)_846 Primer Sequence (5'-3')*C | CAAGCAGAAGACGGCATACGAGATTGCATTCAGTGACT GGAGTTCAGACGTGTGCTCTTCCGATCTATACCGTTAT TAACATATGACAACTCAATTAAA*C | Synthesized |
|  | MGI(+)_849 Index Seq | AACAAAAC | Synthesized |
|  | MGI(+)_849 Rev comp | GTTTTGTT | Synthesized |
| 25 | MGI(+)_849 Primer Sequence (5'-3')*C | CAAGCAGAAGACGGCATACGAGATGTTTTGTTGTGACT GGAGTTCAGACGTGTGCTCTTCCGATCTATACCGTTAT TAACATATGACAACTCAATTAAA*C | Synthesized |

TABLE A-continued

Sequences

| SEQ ID NO | Name | Sequence | Source |
|---|---|---|---|
|  | MGI(+)_850 Index Seq | AACCCCTT | Synthesized |
|  | MGI(+)_850 Rev comp | AAGGGGTT | Synthesized |
| 26 | MGI(+)_850 Primer Sequence (5'-3')*C | CAAGCAGAAGACGGCATACGAGATAAGGGGTTGTGACTGGAGTTCAGACGTGTGCTCTTCCGATCTATACCGTTATTAACATATGACAACTCAATTAAA*C | Synthesized |
|  | MGI(+)_851 Index Seq | AACTTGAT | Synthesized |
|  | MGI(+)_851 Rev comp | ATCAAGTT | Synthesized |
| 27 | MGI(+)_851 Primer Sequence (5'-3')*C | CAAGCAGAAGACGGCATACGAGATATCAAGTTGTGACTGGAGTTCAGACGTGTGCTCTTCCGATCTATACCGTTATTAACATATGACAACTCAATTAAA*C | Synthesized |
|  | MGI(+)_852 Index Seq | AAGACTTA | Synthesized |
|  | MGI(+)_852 Rev comp | TAAGTCTT | Synthesized |
| 28 | MGI(+)_852 Primer Sequence (5'-3')*C | CAAGCAGAAGACGGCATACGAGATTAAGTCTTGTGACTGGAGTTCAGACGTGTGCTCTTCCGATCTATACCGTTATTAACATATGACAACTCAATTAAA*C | Synthesized |
|  | MGI(+)_853 Index Seq | AAGCGAGT | Synthesized |
|  | MGI(+)_853 Rev comp | ACTCGCTT | Synthesized |
| 29 | MGI(+)_853 Primer Sequence (5'-3')*C | CAAGCAGAAGACGGCATACGAGATACTCGCTTGTGACTGGAGTTCAGACGTGTGCTCTTCCGATCTATACCGTTATTAACATATGACAACTCAATTAAA*C | Synthesized |
|  | MGI(+)_854 Index Seq | AAGGACCA | Synthesized |
|  | MGI(+)_854 Rev comp | TGGTCCTT | Synthesized |
| 30 | MGI(+)_854 Primer Sequence (5'-3')*C | CAAGCAGAAGACGGCATACGAGATTGGTCCTTGTGACTGGAGTTCAGACGTGTGCTCTTCCGATCTATACCGTTATTAACATATGACAACTCAATTAAA*C | Synthesized |
|  | MGI(+)_855 Index Seq | AATAGGGA | Synthesized |
|  | MGI(+)_855 Rev comp | TCCCTATT | Synthesized |
| 31 | MGI(+)_855 Primer Sequence (5'-3')*C | CAAGCAGAAGACGGCATACGAGATTCCCTATTGTGACTGGAGTTCAGACGTGTGCTCTTCCGATCTATACCGTTATTAACATATGACAACTCAATTAAA*C | Synthesized |
|  | MGI(+)_876 Index Seq | CCAACATA | Synthesized |
|  | MGI(+)_876 Rev comp | TATGTTGG | Synthesized |

TABLE A-continued

Sequences

| SEQ ID NO | Name | Sequence | Source |
|---|---|---|---|
| 32 | MGI(+)_876 Primer Sequence (5'-3')*C | CAAGCAGAAGACGGCATACGAGATTATGTTGGGTGACT GGAGTTCAGACGTGTGCTCTTCCGATCTATACCGTTAT TAACATATGACAACTCAATTAAA*C | Synthesized |
| | MGI(+)_877 Index Seq | CCACGCGT | Synthesized |
| | MGI(+)_877 Rev comp | ACGCGTGG | Synthesized |
| 33 | MGI(+)_877 Primer Sequence (5'-3')*C | CAAGCAGAAGACGGCATACGAGATACGCGTGGGTGACT GGAGTTCAGACGTGTGCTCTTCCGATCTATACCGTTAT TAACATATGACAACTCAATTAAA*C | Synthesized |
| | MGI(+)_882 Index Seq | GAAACCAC | Synthesized |
| | MGI(+)_882 Rev comp | GTGGTTTC | Synthesized |
| 34 | MGI(+)_882 Primer Sequence (5'-3')*C | CAAGCAGAAGACGGCATACGAGATGTGGTTTCGTGACT GGAGTTCAGACGTGTGCTCTTCCGATCTATACCGTTAT TAACATATGACAACTCAATTAAA*C | Synthesized |
| | MGI(+)_884 Index Seq | TCGGCATA | Synthesized |
| | MGI(+)_884 Rev comp | TATGCCGA | Synthesized |
| 35 | MGI(+)_884 Primer Sequence (5'-3')*C | CAAGCAGAAGACGGCATACGAGATTATGCCGAGTGACT GGAGTTCAGACGTGTGCTCTTCCGATCTATACCGTTAT TAACATATGACAACTCAATTAAA*C | Synthesized |
| | MGI(-)_504 Index Seq | GGCTCTGA | Synthesized |
| | MGI(-)_504 Rev comp | TCAGAGCC | Synthesized |
| 36 | MGI(-)_504 Primer Sequence (5'-3')*C | CAAGCAGAAGACGGCATACGAGATTCAGAGCCGTGACT GGAGTTCAGACGTGTGCTCTTCCGATCTGTTTAATTGA GTTGTCATATGTTAATAACGGTA*T | Synthesized |
| | MGI(-)_810 Index Seq | TAGCTTCA | Synthesized |
| | MGI(-)_810 Rev comp | TGAAGCTA | Synthesized |
| 37 | MGI(-)_810 Primer Sequence (5'-3')*C | CAAGCAGAAGACGGCATACGAGATTGAAGCTAGTGACT GGAGTTCAGACGTGTGCTCTTCCGATCTGTTTAATTGA GTTGTCATATGTTAATAACGGTA*T | Synthesized |
| | MGI(-)_832 Index Seq | GATATACG | Synthesized |
| | MGI(-)_832 Rev comp | CGTATATC | Synthesized |
| 38 | MGI(-)_832 Primer Sequence (5'-3')*C | CAAGCAGAAGACGGCATACGAGATCGTATATCGTGACT GGAGTTCAGACGTGTGCTCTTCCGATCTGTTTAATTGA GTTGTCATATGTTAATAACGGTA*T | Synthesized |

TABLE A-continued

Sequences

| SEQ ID NO | Name | Sequence | Source |
|---|---|---|---|
| | MGI(-)_833 Index Seq | GATGCTAC | Synthesized |
| | MGI(-)_833 Rev comp | GTAGCATC | Synthesized |
| 39 | MGI(-)_833 Primer Sequence (5'-3')*C | CAAGCAGAAGACGGCATACGAGATGTAGCATCGTGACTGGAGTTCAGACGTGTGCTCTTCCGATCTGTTTAATTGAGTTGTCATATGTTAATAACGGTA*T | Synthesized |
| | MGI(-)_834 Index Seq | GTAGAGTT | Synthesized |
| | MGI(-)_834 Rev comp | AACTCTAC | Synthesized |
| 40 | MGI(-)_834 Primer Sequence (5'-3')*C | CAAGCAGAAGACGGCATACGAGATAACTCTACGTGACTGGAGTTCAGACGTGTGCTCTTCCGATCTGTTTAATTGAGTTGTCATATGTTAATAACGGTA*T | Synthesized |
| | MGI(-)_839 Index Seq | GTCCGCAC | Synthesized |
| | MGI(-)_839 Rev comp | GTGCGGAC | Synthesized |
| 41 | MGI(-)_839 Primer Sequence (5'-3')*C | CAAGCAGAAGACGGCATACGAGATGTGCGGACGTGACTGGAGTTCAGACGTGTGCTCTTCCGATCTGTTTAATTGAGTTGTCATATGTTAATAACGGTA*T | Synthesized |
| | MGI(-)_847 Index Seq | TTCTCCGA | Synthesized |
| | Rev comp | TCGGAGAA | Synthesized |
| 42 | Primer Sequence (5'-3')*C | CAAGCAGAAGACGGCATACGAGATTCGGAGAAGTGACTGGAGTTCAGACGTGTGCTCTTCCGATCTGTTTAATTGAGTTGTCATATGTTAATAACGGTA*T | Synthesized |
| | MGI(-)_848 Index Seq | TGCCATCG | Synthesized |
| | Rev comp | CGATGGCA | Synthesized |
| 43 | Primer Sequence (5'-3')*C | CAAGCAGAAGACGGCATACGAGATCGATGGCAGTGACTGGAGTTCAGACGTGTGCTCTTCCGATCTGTTTAATTGAGTTGTCATATGTTAATAACGGTA*T | Synthesized |
| | MGI(-)_856 Index Seq | ACAAACCG | Synthesized |
| | Rev comp | CGGTTTGT | Synthesized |
| 44 | Primer Sequence (5'-3')*C | CAAGCAGAAGACGGCATACGAGATCGGTTTGTGTGACTGGAGTTCAGACGTGTGCTCTTCCGATCTGTTTAATTGAGTTGTCATATGTTAATAACGGTA*T | Synthesized |
| | MGI(-)_864 Index Seq | ATACGGCG | Synthesized |
| | Rev comp | CGCCGTAT | Synthesized |
| 45 | Primer Sequence (5'-3')*C | CAAGCAGAAGACGGCATACGAGATCGCCGTATGTGACTGGAGTTCAGACGTGTGCTCTTCCGATCTGTTTAATTGAGTTGTCATATGTTAATAACGGTA*T | Synthesized |
| | MGI(-)_865 Index Seq | ATCCTAAC | Synthesized |

TABLE A-continued

Sequences

| SEQ ID NO | Name | Sequence | Source |
|---|---|---|---|
| | Rev comp | GTTAGGAT | Synthesized |
| 46 | Primer Sequence (5'-3')*C | CAAGCAGAAGACGGCATACGAGATGTTAGGATGTGACTGGAGTTCAGACGTGTGCTCTTCCGATCTGTTTAATTGAGTTGTCATATGTTAATAACGGTA*T | Synthesized |
| | MGI(-)_868 Index Seq | ATTCCTTT | Synthesized |
| | Rev comp | AAAGGAAT | Synthesized |
| 47 | Primer Sequence (5'-3')*C | CAAGCAGAAGACGGCATACGAGATAAAGGAATGTGACTGGAGTTCAGACGTGTGCTCTTCCGATCTGTTTAATTGAGTTGTCATATGTTAATAACGGTA*T | Synthesized |
| | MGI(-)_874 Index Seq | CATGGCTT | Synthesized |
| | Rev comp | AAGCCATG | Synthesized |
| 48 | Primer Sequence (5'-3')*C | CAAGCAGAAGACGGCATACGAGATAAGCCATGGTGACTGGAGTTCAGACGTGTGCTCTTCCGATCTGTTTAATTGAGTTGTCATATGTTAATAACGGTA*T | Synthesized |
| | MGI(-)_875 Index Seq | CATTTTAT | Synthesized |
| | MGI(-)_875 Rev comp | ATAAAATG | Synthesized |
| 49 | MGI(-)_875 Primer Sequence (5'-3')*C | CAAGCAGAAGACGGCATACGAGATATAAAATGGTGACTGGAGTTCAGACGTGTGCTCTTCCGATCTGTTTAATTGAGTTGTCATATGTTAATAACGGTA*T | Synthesized |
| | MGI(-)_878 Index Seq | CCCATGCA | Synthesized |
| | MGI(-)_878 Rev comp | TGCATGGG | Synthesized |
| 50 | MGI(-)_878 Primer Sequence (5'-3')*C | CAAGCAGAAGACGGCATACGAGATTGCATGGGGTGACTGGAGTTCAGACGTGTGCTCTTCCGATCTGTTTAATTGAGTTGTCATATGTTAATAACGGTA*T | Synthesized |
| | MGI(-)_881 Index Seq | CGTACGTA | Synthesized |
| | MGI(-)_881 Rev comp | TACGTACG | Synthesized |
| 51 | MGI(-)_881 Primer Sequence(5'-3')*C | CAAGCAGAAGACGGCATACGAGATTACGTACGGTGACTGGAGTTCAGACGTGTGCTCTTCCGATCTGTTTAATTGAGTTGTCATATGTTAATAACGGTA*T | Synthesized |
| 52 | P5 | AATGATACGGCGACCACCG*A | Synthesized |
| 53 | Apapter_P5 | AATGATACGGCGACCACCGAGATCTACACTTGAGCTCACACTCTTTCCCTACACGACGCTCTTCCGATC*T | Synthesized |
| 54 | Apapter_P7 | GATCGGAAGAGCACACGTCTGAACTCCAGTCACTATAGCCTATCTCGTATGCCGTCTTCTGCTTG | Synthesized |

What is claimed is:

1. A human primary T cell comprising a chimeric antigen receptor (CAR-T cell),
wherein the chimeric antigen receptor (CAR) specifically binds to CD7 and comprises a 4-1BB costimulatory domain, and
wherein the CAR-T cell comprises
a first genetic modification comprising a first indel in the genomic locus of CD7, wherein the first indel occurs at a position within:
80,274,181-80,274,203;
80,274,195-80,274,217;
80,274,238-80,274,260;
80,274,239-80,274,261;
80,274,555-80,274,577;
80,274,563-80,274,585;
80,274,569-80,274,591;
80,274,571-80,274,593;
80,274,580-80,274,602; or
80,274,586-80,274,608 of chromosome 17, wherein positional numbering is according to Genome Reference Consortium Human Build 37 (GRCh37); and
a second genetic modification comprising a second indel in the genomic locus of TRAC, wherein the second indel occurs at a position within 23,016,517-23,016,536 of chromosome 14, wherein positional numbering is according to Genome Reference Consortium Human Build 37 (GRCh37).

2. The human primary T cell of claim 1, wherein the first indel occurs at a position within 80,274,181-80,274,203.

3. The human primary T cell of claim 1, wherein the first indel occurs at a position within 80,274,195-80,274,217.

4. The human primary T cell of claim 1, wherein the first indel occurs at a position within 80,274,238-80,274,260.

5. The human primary T cell of claim 1, wherein the first indel occurs at a position within 80,274,239-80,274,261.

6. The human primary T cell of claim 1, wherein the first indel occurs at a position within 80,274,555-80,274,577.

7. The human primary T cell of claim 1, wherein the first indel occurs at a position within 80,274,563-80,274,585.

8. The human primary T cell of claim 1, wherein the first indel occurs at a position within 80,274,569-80,274,591.

9. The human primary T cell of claim 1, wherein the first indel occurs at a position within 80,274,571-80,274,593.

10. The human primary T cell of claim 1, wherein the first indel occurs at a position within 80,274,580-80,274,602.

11. The human primary T cell of claim 1, wherein the first indel occurs at a position within 80,274,586-80,274,608.

12. A human primary T cell comprising a chimeric antigen receptor (CAR-T cell),
wherein the chimeric antigen receptor (CAR) specifically binds to CD7, and
wherein the CAR-T cell comprises
a first genetic modification comprising a first indel in the genomic locus of CD7, wherein the first indel occurs within the genomic region targeted by any one of the sequences selected from SEQ ID NO:7, SEQ ID NO:8, SEQ ID NO:9, SEQ ID NO: 10, SEQ ID NO:11, SEQ ID NO: 12, SEQ ID NO: 13, SEQ ID NO: 14, SEQ ID NO:15 or SEQ ID NO: 16; and
a second genetic modification comprising a second indel in the genomic locus of TRAC, wherein the second indel occurs within the genomic region targeted by residues 1-20 of SEQ ID NO: 19.

13. The human primary T cell of claim 12, wherein the first indel occurs within the genomic region targeted by SEQ ID NO:7.

14. The human primary T cell of claim 12, wherein the first indel occurs within the genomic region targeted by SEQ ID NO:8.

15. The human primary T cell of claim 12, wherein the first indel occurs within the genomic region targeted by SEQ ID NO:9.

16. The human primary T cell of claim 12, wherein the first indel occurs within the genomic region targeted by SEQ ID NO:10.

17. The human primary T cell of claim 12, wherein the first indel occurs within the genomic region targeted by SEQ ID NO:11.

18. The human primary T cell of claim 12, wherein the first indel occurs within the genomic region targeted by SEQ ID NO: 12.

19. The human primary T cell of claim 12, wherein the first indel occurs within the genomic region targeted by SEQ ID NO:13.

20. The human primary T cell of claim 12, wherein the first indel occurs within the genomic region targeted by SEQ ID NO:14.

21. The human primary T cell of claim 12, wherein the first indel occurs within the genomic region targeted by SEQ ID NO:15.

22. The human primary T cell of claim 12, wherein the first indel occurs within the genomic region targeted by SEQ ID NO:16.

23. The CAR-T cell of claim 1 or 12, wherein the indel in the genomic locus of CD7 occurs within the genomic region targeted by residues 1-20 of SEQ ID NO:17 or SEQ ID NO:18.

24. The CAR-T cell of claim 1 or 12, wherein the CAR comprises a signaling domain comprising a CD32 effector domain.

25. A population of two or more CAR-T cells of claim 1 or 12, wherein the population is without contamination with malignant T cells.

26. The population of CAR-T cells of claim 25, wherein the population comprises human primary T cells obtained from a donor who does not have a T cell malignancy.

27. A pharmaceutical composition comprising a therapeutically effective amount of the population of CAR-T cells of claim 25.

28. The CAR-T cell of claim 1 or 12, wherein CD7 and TRAC are genetically modified by multiplex gene editing.

29. A genetically modified human T cell, comprising a chimeric antigen receptor (CAR), the genetically modified T cell further comprising a genome comprising:
  (a) a CD7 gene on chromosome 17 comprising an indel within a genomic sequence that is complementary to residues 1-20 of the sequence set forth in SEQ ID NO: 17 or SEQ ID NO: 18; and
  (b) a TRAC gene on chromosome 14 comprising an indel within a genomic sequence that is complementary to residues 1-20 of the sequences set forth in SEQ ID NO:19,
  wherein the CAR comprises a 4-1BB costimulatory domain and an antigen binding domain that specifically binds a CD7 antigen.

30. A pharmaceutical composition comprising a therapeutically effective amount of a population of CAR-T cells of claim 29.

31. A complex comprising a guide RNA comprising any one of the sequences selected from SEQ ID NO:7, SEQ ID NO:8, SEQ ID NO:9, SEQ ID NO:10, SEQ ID NO:11, SEQ ID NO:12, SEQ ID NO: 13, SEQ ID NO: 14, SEQ ID NO: 15, SEQ ID NO:16, SEQ ID NO: 17, or SEQ ID NO: 18, and a Cas9 protein.

* * * * *

SEQUENCE LISTING

<160> NUMBER OF SEQ ID NOS: 54

<210> SEQ ID NO 1
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 1
gcctgcgtgg gatctacctg aggca                                    25

<210> SEQ ID NO 2
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 2
agctatctag gaggctgctg ggggc                                    25

<210> SEQ ID NO 3
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 3
tggggcaaag agggaaatga                                          20

<210> SEQ ID NO 4
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 4
gtcagatttg ttgctccagg c                                        21

<210> SEQ ID NO 5
<211> LENGTH: 34
<212> TYPE: DNA
<213> ORGANISM: Artificial Sequence
<220> FEATURE:
<223> OTHER INFORMATION: SYNTHESIZED; 5' PHOSPHORYLATION; AND
      PHOSPHOROTHIOATE AT POSITIONS 1, 2, 32 AND 33

<400> SEQUENCE: 5
ataccgttat taacatatga caactcaatt aaac                          34

<210> SEQ ID NO 6
<211> LENGTH: 34
<212> TYPE: DNA
<213> ORGANISM: Artificial Sequence
<220> FEATURE:
<223> OTHER INFORMATION: SYNTHESIZED; 5' PHOSPHORYLATION; AND
      PHOSPHOROTHIOATE AT POSITIONS 1, 2, 32 AND 33

<400> SEQUENCE: 6
gtttaattga gttgtcatat gttaataacg gtat                          34

<210> SEQ ID NO 7
<211> LENGTH: 23

```
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 7
gatgctcgga cgccccacca ngg                                              23

<210> SEQ ID NO 8
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 8
atgctcggac gccccaccaa ngg                                              23

<210> SEQ ID NO 9
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 9
aggctgtctg cgggtcaggg ngg                                              23

<210> SEQ ID NO 10
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 10
atcacggagg tcaatgtcta ngg                                              23

<210> SEQ ID NO 11
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 11
tcagggaggg cggagcctgt ngg                                              23

<210> SEQ ID NO 12
```

```
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 12
gacctccgtg atggcctggc ngg                                           23

<210> SEQ ID NO 13
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 13
cgtgatggcc tggcaggtgt ngg                                           23

<210> SEQ ID NO 14
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 14
gaggtcaatg tctacggctc ngg                                           23

<210> SEQ ID NO 15
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 15
tgtctacggc tccggcaccc ngg                                           23

<210> SEQ ID NO 16
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: n is a, c, g, or t

<400> SEQUENCE: 16
gtagacattg acctccgtga ngg                                           23
```

<210> SEQ ID NO 17
<211> LENGTH: 100
<212> TYPE: RNA
<213> ORGANISM: Artificial Sequence
<220> FEATURE:
<223> OTHER INFORMATION: SYNTHESIZED; GM AT POSITION 1; UM AT POSITION 97; AND PHOSPHOROTHIOATE AT POSITIONS 1, 2, 3, 97, 98 AND 99

<400> SEQUENCE: 17

```
guagacauug accuccguga guuuuagagc uagaaauagc aaguuaaaau aaggcuaguc    60
cguuaucaac uugaaaaagu ggcaccgagu cggugcuuuu                         100
```

<210> SEQ ID NO 18
<211> LENGTH: 100
<212> TYPE: RNA
<213> ORGANISM: Artificial Sequence
<220> FEATURE:
<223> OTHER INFORMATION: SYNTHESIZED; 2'-O-METHYADENSOSINE AT POSITION 1; UM AT POSITION 97; AND PHOSPHOROTHIOATE AT POSITIONS 1, 2, 3, 97, 98 AND 99

<400> SEQUENCE: 18

```
aucacggagg ucaaugucua guuuuagagc uagaaauagc aaguuaaaau aaggcuaguc    60
cguuaucaac uugaaaaagu ggcaccgagu cggugcuuuu                         100
```

<210> SEQ ID NO 19
<211> LENGTH: 100
<212> TYPE: RNA
<213> ORGANISM: Artificial Sequence
<220> FEATURE:
<223> OTHER INFORMATION: SYNTHESIZED

<400> SEQUENCE: 19

```
gagaaucaaa aucggugaau guuuuagagc uagaaauagc aaguuaaaau aaggcuaguc    60
cguuaucaac uugaaaaagu ggcaccgagu cggugcuuuu                         100
```

<210> SEQ ID NO 20
<211> LENGTH: 100
<212> TYPE: DNA
<213> ORGANISM: Artificial Sequence
<220> FEATURE:
<223> OTHER INFORMATION: SYNTHESIZED; and phosphorothioate at position 99

<400> SEQUENCE: 20

```
caagcagaag acggcatacg agatcgcgat tagtgactgg agttcagacg tgtgctcttc    60
cgatctatac cgttattaac atatgacaac tcaattaaac                         100
```

<210> SEQ ID NO 21
<211> LENGTH: 100
<212> TYPE: DNA
<213> ORGANISM: Artificial Sequence
<220> FEATURE:
<223> OTHER INFORMATION: SYNTHESIZED; and phosphorothioate at position 99

<400> SEQUENCE: 21

```
caagcagaag acggcatacg agatgtgctg tagtgactgg agttcagacg tgtgctcttc    60
cgatctatac cgttattaac atatgacaac tcaattaaac                         100
```

<210> SEQ ID NO 22
<211> LENGTH: 100
<212> TYPE: DNA
<213> ORGANISM: Artificial Sequence

```
<220> FEATURE:
<223> OTHER INFORMATION: SYNTHESIZED; and phosphorothioate at position
      99

<400> SEQUENCE: 22
caagcagaag acggcatacg agatatgaat gagtgactgg agttcagacg tgtgctcttc     60
cgatctatac cgttattaac atatgacaac tcaattaaac                          100

<210> SEQ ID NO 23
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 23
caagcagaag acggcatacg agatacggta gagtgactgg agttcagacg tgtgctcttc     60
cgatctatac cgttattaac atatgacaac tcaattaaac                          100

<210> SEQ ID NO 24
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 24
caagcagaag acggcatacg agattgcatt cagtgactgg agttcagacg tgtgctcttc     60
cgatctatac cgttattaac atatgacaac tcaattaaac                          100

<210> SEQ ID NO 25
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 25
caagcagaag acggcatacg agatgttttg ttgtgactgg agttcagacg tgtgctcttc     60
cgatctatac cgttattaac atatgacaac tcaattaaac                          100

<210> SEQ ID NO 26
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 26
caagcagaag acggcatacg agataagggg ttgtgactgg agttcagacg tgtgctcttc     60
cgatctatac cgttattaac atatgacaac tcaattaaac                          100

<210> SEQ ID NO 27
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99
```

-continued

<400> SEQUENCE: 27
caagcagaag acggcatacg agatatcaag ttgtgactgg agttcagacg tgtgctcttc    60
cgatctatac cgttattaac atatgacaac tcaattaaac                          100

<210> SEQ ID NO 28
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 28
caagcagaag acggcatacg agattaagtc ttgtgactgg agttcagacg tgtgctcttc    60
cgatctatac cgttattaac atatgacaac tcaattaaac                          100

<210> SEQ ID NO 29
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 29
caagcagaag acggcatacg agatactcgc ttgtgactgg agttcagacg tgtgctcttc    60
cgatctatac cgttattaac atatgacaac tcaattaaac                          100

<210> SEQ ID NO 30
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 30
caagcagaag acggcatacg agattggtcc ttgtgactgg agttcagacg tgtgctcttc    60
cgatctatac cgttattaac atatgacaac tcaattaaac                          100

<210> SEQ ID NO 31
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 31
caagcagaag acggcatacg agattcccta ttgtgactgg agttcagacg tgtgctcttc    60
cgatctatac cgttattaac atatgacaac tcaattaaac                          100

<210> SEQ ID NO 32
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 32
caagcagaag acggcatacg agattatgtt gggtgactgg agttcagacg tgtgctcttc    60

```
cgatctatac cgttattaac atatgacaac tcaattaaac                         100

<210> SEQ ID NO 33
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 33
caagcagaag acggcatacg agatacgcgt gggtgactgg agttcagacg tgtgctcttc    60
cgatctatac cgttattaac atatgacaac tcaattaaac                         100

<210> SEQ ID NO 34
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 34
caagcagaag acggcatacg agatgtggtt tcgtgactgg agttcagacg tgtgctcttc    60
cgatctatac cgttattaac atatgacaac tcaattaaac                         100

<210> SEQ ID NO 35
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 35
caagcagaag acggcatacg agattatgcc gagtgactgg agttcagacg tgtgctcttc    60
cgatctatac cgttattaac atatgacaac tcaattaaac                         100

<210> SEQ ID NO 36
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 36
caagcagaag acggcatacg agattcagag ccgtgactgg agttcagacg tgtgctcttc    60
cgatctgttt aattgagttg tcatatgtta ataacggtat                         100

<210> SEQ ID NO 37
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 37
caagcagaag acggcatacg agattgaagc tagtgactgg agttcagacg tgtgctcttc    60
cgatctgttt aattgagttg tcatatgtta ataacggtat                         100

<210> SEQ ID NO 38
```

```
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 38
caagcagaag acggcatacg agatcgtata tcgtgactgg agttcagacg tgtgctcttc    60
cgatctgttt aattgagttg tcatatgtta ataacggtat                         100

<210> SEQ ID NO 39
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 39
caagcagaag acggcatacg agatgtagca tcgtgactgg agttcagacg tgtgctcttc    60
cgatctgttt aattgagttg tcatatgtta ataacggtat                         100

<210> SEQ ID NO 40
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 40
caagcagaag acggcatacg agataactct acgtgactgg agttcagacg tgtgctcttc    60
cgatctgttt aattgagttg tcatatgtta ataacggtat                         100

<210> SEQ ID NO 41
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 41
caagcagaag acggcatacg agatgtgcgg acgtgactgg agttcagacg tgtgctcttc    60
cgatctgttt aattgagttg tcatatgtta ataacggtat                         100

<210> SEQ ID NO 42
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 42
caagcagaag acggcatacg agattcggag aagtgactgg agttcagacg tgtgctcttc    60
cgatctgttt aattgagttg tcatatgtta ataacggtat                         100

<210> SEQ ID NO 43
<211> LENGTH: 100
<212> TYPE: DNA
<213> ORGANISM: Artificial Sequence
<220> FEATURE:
```

<223> OTHER INFORMATION: SYNTHESIZED; and phosphorothioate at position
       99

<400> SEQUENCE: 43
caagcagaag acggcatacg agatcgatgg cagtgactgg agttcagacg tgtgctcttc    60
cgatctgttt aattgagttg tcatatgtta ataacggtat                        100

<210> SEQ ID NO 44
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 44
caagcagaag acggcatacg agatcggttt gtgtgactgg agttcagacg tgtgctcttc    60
cgatctgttt aattgagttg tcatatgtta ataacggtat                        100

<210> SEQ ID NO 45
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 45
caagcagaag acggcatacg agatcgccgt atgtgactgg agttcagacg tgtgctcttc    60
cgatctgttt aattgagttg tcatatgtta ataacggtat                        100

<210> SEQ ID NO 46
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 46
caagcagaag acggcatacg agatgttagg atgtgactgg agttcagacg tgtgctcttc    60
cgatctgttt aattgagttg tcatatgtta ataacggtat                        100

<210> SEQ ID NO 47
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 47
caagcagaag acggcatacg agataaagga atgtgactgg agttcagacg tgtgctcttc    60
cgatctgttt aattgagttg tcatatgtta ataacggtat                        100

<210> SEQ ID NO 48
<211> LENGTH: 100
<212> TYPE: DNA
<213> ORGANISM: Artificial Sequence
<220> FEATURE:
<223> OTHER INFORMATION: SYNTHESIZED; and phosphorothioate at position
      99

<400> SEQUENCE: 48

<210> SEQ ID NO 49
<211> LENGTH: 100
<212> TYPE: DNA
<213> ORGANISM: Artificial Sequence
<220> FEATURE:
<223> OTHER INFORMATION: SYNTHESIZED; and phosphorothioate at position 99

<400> SEQUENCE: 49
caagcagaag acggcatacg agatataaaa tggtgactgg agttcagacg tgtgctcttc    60
cgatctgttt aattgagttg tcatatgtta ataacggtat                         100

<210> SEQ ID NO 50
<211> LENGTH: 100
<212> TYPE: DNA
<213> ORGANISM: Artificial Sequence
<220> FEATURE:
<223> OTHER INFORMATION: SYNTHESIZED; and phosphorothioate at position 99

<400> SEQUENCE: 50
caagcagaag acggcatacg agattgcatg gggtgactgg agttcagacg tgtgctcttc    60
cgatctgttt aattgagttg tcatatgtta ataacggtat                         100

<210> SEQ ID NO 51
<211> LENGTH: 100
<212> TYPE: DNA
<213> ORGANISM: Artificial Sequence
<220> FEATURE:
<223> OTHER INFORMATION: SYNTHESIZED; and phosphorothioate at position 99

<400> SEQUENCE: 51
caagcagaag acggcatacg agattacgta cggtgactgg agttcagacg tgtgctcttc    60
cgatctgttt aattgagttg tcatatgtta ataacggtat                         100

<210> SEQ ID NO 52
<211> LENGTH: 20
<212> TYPE: DNA
<213> ORGANISM: Artificial Sequence
<220> FEATURE:
<223> OTHER INFORMATION: SYNTHESIZED; and phosphorothioate at position 19

<400> SEQUENCE: 52
aatgatacgg cgaccaccga                                                20

<210> SEQ ID NO 53
<211> LENGTH: 70
<212> TYPE: DNA
<213> ORGANISM: Artificial Sequence
<220> FEATURE:
<223> OTHER INFORMATION: SYNTHESIZED; and phosphorothioate at position 69

<400> SEQUENCE: 53
aatgatacgg cgaccaccga gatctacact tgagctcaca ctctttccct acacgacgct    60
cttccgatct                                                           70

```
<210> SEQ ID NO 54
<211> LENGTH: 65
<212> TYPE: DNA
<213> ORGANISM: Artificial Sequence
<220> FEATURE:
<223> OTHER INFORMATION: SYNTHESIZED

<400> SEQUENCE: 54
gatcggaaga gcacacgtct gaactccagt cactatagcc tatctcgtat gccgtcttct    60
gcttg                                                                65
```